US010723770B2

(12) United States Patent
Yonath et al.

(10) Patent No.: US 10,723,770 B2
(45) Date of Patent: Jul. 28, 2020

(54) **CRYSTAL STRUCTURE OF THE LARGE RIBOSOMAL SUBUNIT FROM *S. AUREUS***

(71) Applicant: Yeda Research and Development Co. Ltd., Rehovot (IL)

(72) Inventors: Ada Yonath, Rehovot (IL); Zohar Eyal, Rehovot (IL); Donna Matzov, Rehovot (IL); Haim Rozenberg, Rehovot (IL); Ella Zimmerman, Rehovot (IL); Anat Bashan, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 0 days.

(21) Appl. No.: 16/726,290

(22) Filed: Dec. 24, 2019

(65) Prior Publication Data

US 2020/0131232 A1    Apr. 30, 2020

Related U.S. Application Data

(62) Division of application No. 15/547,499, filed as application No. PCT/IL2016/050082 on Jan. 26, 2016, now Pat. No. 10,556,934.

(60) Provisional application No. 62/109,185, filed on Jan. 29, 2015, provisional application No. 62/280,231, filed on Jan. 19, 2016.

(51) Int. Cl.
| | |
|---|---|
| *C07K 14/31* | (2006.01) |
| *C07H 17/08* | (2006.01) |
| *C07D 263/20* | (2006.01) |
| *C07D 211/54* | (2006.01) |
| *G16B 15/00* | (2019.01) |
| *G16B 30/00* | (2019.01) |
| *G16C 20/50* | (2019.01) |
| *G16B 35/00* | (2019.01) |
| *G16C 20/60* | (2019.01) |

(52) U.S. Cl.
CPC ............ *C07K 14/31* (2013.01); *C07D 211/54* (2013.01); *C07D 263/20* (2013.01); *C07H 17/08* (2013.01); *G16B 15/00* (2019.02); *G16B 30/00* (2019.02); *G16C 20/50* (2019.02); *C07K 2299/00* (2013.01); *G16B 35/00* (2019.02); *G16C 20/60* (2019.02)

(58) Field of Classification Search
None
See application file for complete search history.

(56) References Cited

U.S. PATENT DOCUMENTS

2018/0009853 A1    1/2018  Yonath et al.

FOREIGN PATENT DOCUMENTS

WO    WO 2016/120868    8/2016

OTHER PUBLICATIONS

Communication Pursuant to Article 94(3) EPC dated May 7, 2018 From the European Patent Office Re. Application No. 16711899.1. (4 Pages).
Communication Pursuant to Article 94(3) EPC dated Jan. 17, 2019 From the European Patent Office Re. Application No. 16711899.1. (4 Pages).
International Preliminary Report on Patentability dated Aug. 10, 2017 From the International Bureau of WIPO Re. Application No. PCT/IL2016/050082. (10 Pages).
International Search Report and the Written Opinion dated May 23, 2016 From the International Searching Authority Re. Application No. PCT/IL2016/050082.
Official Action dated Jun. 21, 2019 From the US Patent and Trademark Office Re. U.S. Appl. No. 15/547,499. (24 pages).
Restriction Official Action dated Feb. 21, 2019 From the US Patent and Trademark Office Re. U.S. Appl. No. 15/547,499. (7 pages).
Belousoff et al. "Crystal Structure of the Synergistic Antibiotic Pair, Lankamycin and Lankacidin, in Complex With the Large ibosomal Subunit", Proc. Natl. Acad. Sci. USA, PNAS, 108(7): 2717-2722, Feb. 15, 2011.
Ben-Shem et al. "The Structure of the Eukaryotic Ribosome at 3.0 A Resolution", Science, 334: 1524-1529, Dec. 16, 2011.
Benvenuti et al. "Crystallization of Soluble Proteins in Vapor Diffusion for X-Ray Crystallography", Nature Protocols, 2(7): 1633-1651, Published Online Jun. 28, 2007.
Berisio et al. "Structural Insight Into the Antibiotic Action of Telithromycin Against Resistant Mutants", Journal of Bacteriology, 185(14): 4276-4279, Jul. 2003.
Bulkey et al. "Revisiting the Structures of Several Antibiotics Bound to the Bacterial Ribosome", Proc. Natl. Acad. Sci. USA, PNAS, 107(40): 17158-17163, Oct. 5, 2010.
Cudney "Protein Crystallization and Dumb Luck", The Rigaku Journal, 16(1): p. 1-7, 1999.
Davidovich "In a 'Regular' Format. Targeting Functional Centers of the Ribosome", Thesis for the Degree Doctor of Philosophy, Submitted to the Scientific Council of the Weizman Institute of Science, Rehovot, Israel, 128 P., Apr. 2010.
Davidovich et al. "Induced-Fit Tightens Pleuromutilins Binding to Ribosomes and Remote Interactions Enable Their Selectivity", Proc. Natl. Acad. Sci. USA, PNAS, 104(11): 4291-4296, Mar. 13, 2007.

(Continued)

*Primary Examiner* — Suzanne M Noakes

(57) ABSTRACT

A composition-of-matter comprising a crystallized form of a large ribosomal (50S) subunit of a pathogenic bacterium, and the atomic coordinates of the three-dimensional structure thereof are provided herein, as well as methods for crystallizing the same, and using the atomic coordinates of the same to design de novo ligands with high specificity thereto.

19 Claims, 18 Drawing Sheets
(18 of 18 Drawing Sheet(s) Filed in Color)
Specification includes a Sequence Listing.

(56) References Cited

OTHER PUBLICATIONS

Drenth "Principles of Protein X-Ray Crystallography", 2nd Edition, Springer-Verlag New York Inc., Chapter 1, p. 1-21, 1999.
Dunkle et al. "Structures of the *Escherichia coli* Ribosome With Antibiotics Bound Near the Peptidyl Transferase Center Explain Spectra of Drug Action", Proc. Natl. Acad. Sci. USA, PNAS, XP055272581, 107(40): 17152-17157, Oct. 5, 2010. p. 17156, r-h col., Last Para.
Eyal et al. "Structural Insights Into Species-Specific Features of the Ribosome From the Pathogen *Staphylococcus Aureus*", Proc. Natl. Acad. Sci. USA, PNAS, XP055272107, 112(43): E5805-E5814, Published Online Oct. 13, 2015.
Garreau de Loubresse et al. "Structural Basis for the Inhibition of the Eukaryotic Ribosome", Nature, 513: 517-533, Sep. 25, 2014.
Harms et al. "Alterations at the Peptidyl Transferase Centre of the Ribosome Induced by the Synergistic Action of the Streptogramins Dalfopristin and Quinupristin", BMC Biology, 2(4): 1-10, Apr. 1, 2004.
Ippolito et al. "Crystal Structure of the Oxazolidinone Antibiotic Linezolid Bound to the 50S Ribosomal Subunit", Journal of Medicinal Chemistry, 51: 3353-3356, May 22, 2008.
Klinge et al. "Atomic Structures of the Eukaryotic Ribosome", Trends in Biochemical Sciences, 37(5): 189-198, May 2012.
Kundrot "Which Strategy for a Protein CVrystallization Project?", CMLS Cellular and Molecular Life Sciences, 61: 525-536, 2004.
Leach et al. "The Site of Action of Oxazolidinone Antibiotics in Living Bacteria and in Human Mitochondria", Cell, 26: 393-402, May 11, 2007.
McLellan et al. "A Systematic Study of 50S Ribosomal Subunit Purification Enabling Robust Crystallization", Acta Crystallographica Section D: Biological Crystallography, XP0552725517, 65(12): 1270-1282, Dec. 1, 2009.
McPherson "Current Approaches to Macromolecular Crystallization", European Journal of Biochemistry 189: 1-23, 1990.
Moon et al. "A Synergistic Approach to Protein Crystallization: Combination of a Fixed-Arm Carrier With Surface Entropy Reduction", Protein Science, 19: 901-913, 2010.
Petrov et al. "Evolution of the Ribosome at Atomic Resolution", Proc. Natl. Acad. Sci. USA, PNAS, 111(28): 10251-10256, Jul. 15, 2014.
Schluenzen et al. "Inhibition of Peptide Bond Formation by Pleuromutilins: The Structure of the 50S Ribosomal Subunit From Deinococcus Radiodurans in Complex With Tiamulin", Molecular Microbiology, 54(5): 1287-1294, 2004.
Schluenzen et al. "Structural Basis for the Interaction of Antibiotics With the Peptidyl Transferase Centre in Eubacteria", Nature, 413: 814-821, Oct. 25, 2001.
Schuwirth et al. "Structures of the Bacterial Ribosome at 3.5 A Resolution", Science, 310(5749): 827-834, Nov. 4, 2005.
Selmer et al. "Structure of the 70S Ribosome Complexed With mRNA and tRNA", Science 313: 1935-1942, Sep. 29, 2006.
Tu et al. "Structures of MLS[B]K Antibiotics Bound to Mutated Large Ribosomal Subunits Provide a Structural Explanation to Resistance", Cell, 121: 257-270, Apr. 22, 2005.
Voorhees et al. "insights Into Substrate Stabilization From Snapshots of the Peptidyl Transferase Center of the Intact 70S Ribosome", Nature Structural & Molecular Biology, 16(5): 528-533, Published Online Apr. 12, 2009.
Wilson "On the Specificity of Antibiotics Targeting the Large Ribosomal Subunit", Annals of the New York Academy of Sciences, 1241: 1-16, 2011.
Wilson "Ribosome-Targeting Antibiotics and Mechanisms of Bacterial Resistance", Nature Reviews Microbiology, XP055222672, 12(1): 35-48, Published Online Dec. 16, 2013. p. 36, l-h col., p. 45, r-h col., Last Para.
Wilson et al. "Species-Specific Antibiotic-Ribosome Interactions: Implications for Drug Development", Biological Chemistry, 386: 1239-1252, Dec. 2005.
Wilson et al. "The Oxazolidinone Antibiotics Perturb the Ribosomal Peptidyl-Transferase Center and Effect tRNA Positioning", Proc. Natl. Acad. Sci. USA, PNAS, 105(36): 13339-13344, Sep. 9, 2008.
Yonath "Ribosomal Crystallography: Peptide Bond Formation, Chaperone Assistance and Antibiotics Activity", Molecules and Cells, 20(1): 1-16, 2005.

FIG. 1
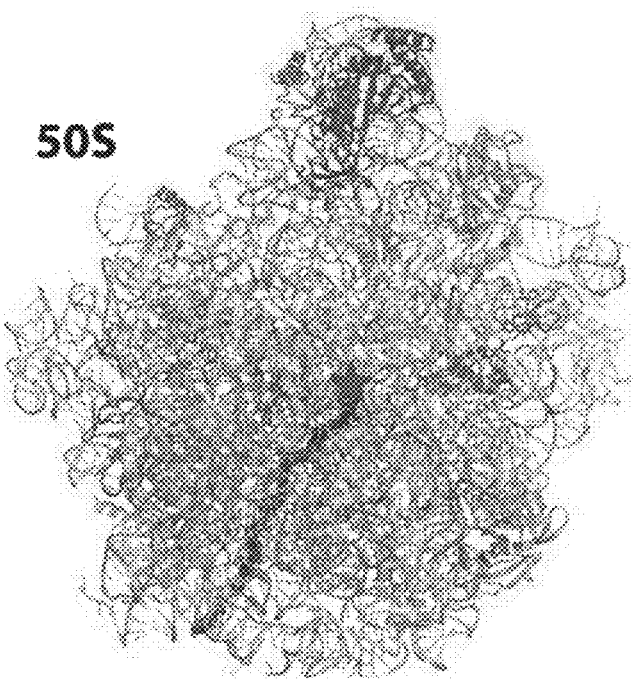
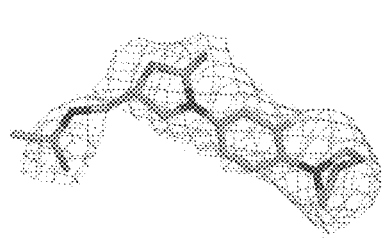
FIG. 2A
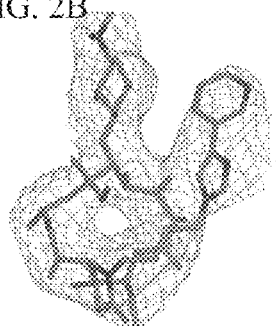
FIG. 2B
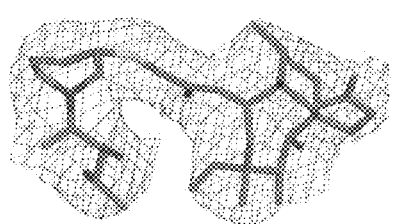
FIG. 2C
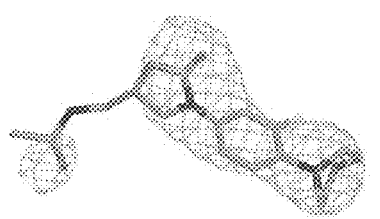
FIG. 2D
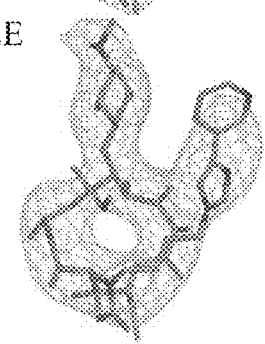
FIG. 2E
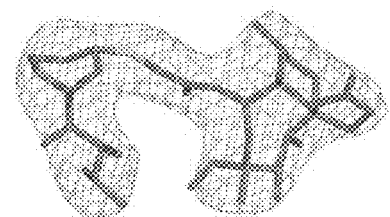
FIG. 2F
Linezolid      Telithromycin      BC-3205

CRYSTAL STRUCTURE OF THE LARGE RIBOSOMAL SUBUNIT FROM *S. AUREUS*

RELATED APPLICATIONS

This application is a divisional of U.S. patent application Ser. No. 15/547,499 filed on Jul. 30, 2017, which is a National Phase of PCT Patent Application No. PCT/IL2016/050082 having International Filing Date of Jan. 26, 2016, which claims the benefit of priority under 35 USC § 119(e) of U.S. Provisional Patent Application Ser. Nos. 62/109,185 filed on Jan. 29, 2015, and 62/280,231 filed on Jan. 19, 2016. The contents of the above applications are all incorporated by reference as if fully set forth herein in their entirety.

SEQUENCE LISTING STATEMENT

The ASCII file, entitled 80470SequenceListing.txt, created on Dec. 17, 2019, comprising 36,162 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to crystal structures and structure-based drug design and, more particularly, but not exclusively, to methods of designing species-specific antimicrobial agents based on crystal structures of pathogenic ribosomal subunits.

The clinical usage of the currently available antibiotics is becoming ever more limited due to the capability of pathogens to undergo mutations, the phenotype thereof minimizes or abolishes binding interaction of the antibiotics to the molecular target in the pathogen. The emergence of bacterial resistance to antibiotics threatens regression to the pre-antibiotic era as the treatments of infections with the available arsenal of clinically used antibiotics have suffered from the appearance of multidrug-resistant strains. Consequently, many hospital-acquired infections are currently caused by highly resistant bacteria such as methicillin-resistant *Staphylococcus aureus* (MRSA) and vancomycin-resistant *Staphylococcus aureus* (VRSA), Gram positive versatile and aggressive pathogens that are among the most worrisome pathogenic bacteria.

Among the existing antibiotics, many target the fundamental process of protein biosynthesis, mostly by interrupting bacteria's ribosomal activity. A large number of antibiotics target the universal cellular multi-components RNP (RNA-protein) particles translating the genetic code into proteins.

The increasing epidemiology of *Staphylococcus aureus* (SA) infections revealed that most of SA strains have 5-6 copies of the operon of the main rRNA (ribosomal RNA) component, namely the 23S rRNA. The fact that SA has 5-6 operon copies is most likely correlated with the finding that resistance that is caused by a single RNA mutation is accumulative.

It has been observed that in SA, the commonly occurring resistance to ribosomal-active antibiotics is acquired by a single-nucleotide mutation in the 23S large ribosomal subunit rRNA. SA resistant mutations are also associated with the region of rProtein (ribosomal protein) L3 that is located in proximity to the peptidyl transferase center (PTC) and rProteins L4 and L22 that reach the exit tunnel.

Infections caused by SA are typically treated by several antibiotics, including the ribosomal-active antibiotics linezolid, telithromycin and pleuromutilins such as BC-3205, the structures of which are presented hereinbelow, which bind to the large ribosomal subunit.

Linezolid is a synthetic drug which has been approved by FDA on April 2000 for treating Gram positive pathogen infections. It belongs to the class of oxazolidinones and was designed to bind at the PTC. Since linezolid is a synthetic drug, no pre-existing resistance mechanisms were known prior to its use, although resistance to other ribosomal-active antibiotics that target the same site has been identified. However, it was expected that emergence of resistance to this drug would occur rather slowly. Despite these expectations, *S. aureus* linezolid resistance, acquired by a specific 23S point mutation, referred to as G2576U (*E. coli* numbering is used throughout), was reported a year after its approval for treatment. Since linezolid is often used as the last line of defense against multidrug-resistant bacterial infections, a resistance to linezolid in clinical isolates was reported to be rather rare, and on 2010, it was reported to occur in less than 1% of SA isolates.

The observed G2576U resistance mutation is in accord with the crystal structures and with a model of ribosome-linezolid complexes [Wilson, D. N. et al., *P.N.A.S. USA*, 2008, 105(36), p. 13339-44; Ippolito, J. A. et al., *J Med Chem*, 2008, 51(12), p. 3353-6; and Leach, K. L. et al., *Molecular Cell*, 2007, 26(3), p. 393-402], which indicate that the drug binding site is composed of 23S rRNA nucleotides that form the inner shell of the PTC, thus perturbing the correct positioning of tRNAs on the ribosome. Interestingly, the G2576U resistance mutation was found to be associated with linezolid resistance in the multi-drug resistant bacteria *Enterococcus faecium* and *Enterococcus faecalis* and in *S. pneumonia*, as well as the tuberculosis diagnostic tool *Mycobacterium smegmatis*.

Telithromycin is a ketolide antibacterial agent/drug (antibiotic) that is structurally related to macrolides, and which has been developed specifically to provide optimal therapy for the treatment of respiratory tract infections (RTI) caused by either typical or atypical respiratory pathogens. Ketolides possess two innovative structural modifications, a 3-keto group and a large N-substituted C11, C12-carbamate side chain. Telithromycin has an additional long alkyl-aryl arm. Telithromycin have showed potent in vitro activity against *S. pneumoniae*, including strains resistant to macrolide-lincosamide-streptogramin B ketolide ($MLS_BK$) and sub-inhibitory concentrations of telithromycin have been found to inhibit MRSA in vitro.

Crystal structures showed that telithromycin binds to the large ribosomal subunit at the macrolide binding pocket in the ribosome's exit tunnel [Berisio, R. et al., *J Bacteriol.*, 2003, 185(14), p. 4276-9; Tu, D et al., *Cell*, 2005, 121(2), p. 257-70; Dunkle, J. A. et al., *Proc Natl Acad Sci USA*, 2010, 107(40), p. 17152-17157; and Bulkley, D. et al., *Proc Natl Acad Sci USA*, 2010, 107(40), p. 17158-63], and that its flexible alkyl-aryl arm is pointing in different directions in different species.

Pleuromutilin and its derivatives are antibacterial agents (antibiotics) that inhibit protein synthesis in bacteria by binding to the peptidyl transferase component (PTC) of the 50S subunit of ribosomes. Pleuromutilin is a natural product of the fungi *Pleurotus mutilus* (also known as *Clitopilus scyphoides*), which has been used as a base for the synthesis of several semi-synthetic antibacterial agents, designed for clinical utilization by targeting eubacterial ribosomes. Members of this class of antibiotics, collectively referred to herein and in the art as Pleuromutilins, which includes retapamulin, valnemulin and tiamulin and some investigational drugs such as azamulin and BC-3781, all exhibit a tricyclic mutilin core, a C21 keto group, essential for antimicrobial activity, and various substituents at the C14, most of which are extensions of diverse chemical nature. Some of these semi-synthetic antibacterial agents are already in clinical use and exhibit elevated activity over a broad spectrum of pathogens.

Retapamulin belongs to the group of C14-sulfanyl-acetate derivatives of Pleuromutilin, and was approved for use as a topical antibiotic on 2007. Retapamulin was shown to possess potent activity against Gram positive pathogens, and a low propensity to develop resistance. Thus, all strains of *Staphylococcus aureus* and *Streptococcus pyogenes* were susceptible to retapamulin at a minimal inhibition concentration (MIC) of 0.5 gram/ml. Other C14-sulfanyl-acetate derivatives of Pleuromutilin, valnemulin and tiamulin, were approved for veterinary clinical use.

Recent advances in pleuromutilin's chemistry yielded several new compounds as potential antibacterial agents. Among them are BC-3205, which is a semi-synthetic pleuromutilin derivative that was developed for oral treatment of skin and skin structure infections (SSSI) and community-acquired pneumonia (CAP), as well as BC-3781 and BC-7013, all of which by Nabriva Therapeutics AG, Vienna, Austria. BC-3205 acts against SA with a MIC of 0.06 μg/ml, is 16-32-fold more potent than linezolid against SA and is therefore considered as highly potent antibacterial agent.

The available crystal structures of complexes of the large ribosomal subunit from a non-pathogenic model bacterium, D50S, with various pleuromutilin compounds, namely tiamulin, retapamulin, SB-264128 and SB-571519, revealed that these compounds are bound to the large ribosomal subunit at the PTC. In all cases the cores of these compounds are placed in a similar fashion at the A-site, and the C14 extensions of these compounds are pointing towards the P-site, thus, directly inhibiting peptide bond formation. As the PTC is almost fully conserved, the pleuromutilin's efficient inhibitory modes are attained by exploiting the ribosomal intrinsic functional flexibility for induced-fit and remote conformational rearrangements that result in tightening up the binding pockets [Schlünzen, F. et al., *Molecular microbiology,* 2004, 54, p. 1287-1294; and Davidovich, C. et al., *Proceedings of the National Academy of Sciences,* 104, p. 4291-4296].

Species specificity in relevance to emergence of resistance to antibiotics in bacteria has been observed; however, so far all available structural information on ribosomal-antibiotics interactions has been obtained from ribosomal particles and subunits of non-pathogenic bacteria, which only emphasized the common traits. Previous studies which compared structures of ribosomes from different kingdoms of life [Petrov, A.S. et al., *P.N.A.S. USA,* 2014, 111(28), p. 10251-10256] have prompted suggestions concerning pathways in ribosome evolution.

Previous structural studies on antibiotics' modes of binding and bioactivity were based only on the available ribosomal crystal structures, which were of eubacteria suitable to mimic pathogens under clinical relevant conditions. These include D50S of *Deinococcus radiodurans* [Schluenzen, F. et al., *Nature,* 2001, 413, p. 814-21], T70S of *Thermus thermophilus* [Voorhees, R. M. et al., *Nat Struct Mol Biol.,* 2009, 16(5), p. 528-33] and E70S from the non-pathogenic strain of *Escherichia coli* [Schuwirth, B. S. et al., *Science,* 2005, 310(5749), p. 827-834]. Results of these studies provided useful insights for common traits of the mode of action of antibiotics, such as binding at ribosomal functional sites, e.g. the PTC or the protein exit tunnel; illuminated structural bases for the distinction between patients (eukaryotes) and pathogens (eubacteria) despite the high conservation of the ribosomal functional sites; and shed light on antibiotics synergism and the general principles of resistance and cross resistance.

Based on the similarity in their sequences, the structures of ribosomes from pathogens are expected to resemble ribosomes from other eubacteria; however, species specificity in clinically relevant properties, particularly in the modes of acquiring antibiotic resistance, has been identified [Wilson, D. N., *Ann. N. E Acad. Sci.,* 2011, 1241, p. 1-16], and it has been shown that small structural differences between bacterial species could affect the drug binding [Yonath, A., *Mol Cells,* 2005, 20, p. 1-16].

Additional background art includes U.S. Pat. Nos. 6,638,908, 6,845,328, 6,925,394, 6,939,848, 6,947,844, 6,947,845, 6,952,650, 7,079,956, 7,133,783, 7,504,486, 7,606,670, 7,666,849 and 8,470,990; U.S. Patent Application Publication Nos. 20020072861, 20020086308, 20020106660, 20030027315, 20030099955, 20030153002, 20030171327, 20030232779, 20040034207, 20040265984, 20050036997, 20050154538, 20050233349, 20050234227, 20050272681, 20060136146, 20080057494, 20090081697, 20100131258, 20100204253, 20100312525, 20120316106 and 20140066623; and International Patent Application Publication No. WO 2011/080739, WO 2000/0693912 and WO 2003/026562.

SUMMARY OF THE INVENTION

The possession of the 3D-structure in atomic resolution of one of the most pivotal biomolecular targets, such as the ribosome of a pathogenic bacterium, opens the path to the design of highly specific and effective de novo ligands which can used as drugs that inhibit protein synthesis of a pathogenic bacterium, such as *Staphylococcus aureus*, and therefore can be used to treat medical conditions associated therewith.

According to an aspect of some embodiments of the present invention there is provided a composition-of-matter which includes a crystallized large ribosomal subunit of a pathogenic bacterium, wherein the pathogenic bacterium is:

a pathogenic Gram positive bacterium; and/or a pathogenic bacterium exhibiting a degree of 23S rRNA sequence identity of at least 80% compared to rRNA of *Staphylococcus aureus*; and/or a pathogenic bacterium exhibiting a degree of 23S rRNA sequence identity of less than 99.9% compared to rRNA of *Escherichia coli,* and the crystallized large ribosomal subunit effectively diffracts X-rays for calculating an electron density map and determination of atomic coordinates to a resolution of at least 4 Å.

According to some embodiments of the invention, the Gram positive pathogenic bacterium is a Gram positive cocci bacterium.

According to some embodiments of the invention, the Gram positive cocci bacterium is a *Staphylococcus* bacterium.

According to some embodiments of the invention, the *Staphylococcus* bacterium is *Staphylococcus aureus*.

According to some embodiments of the invention, *Staphylococcus aureus* is capable of developing a resistance to an antibacterial agent.

According to some embodiments of the invention, the *Staphylococcus aureus* is selected from the group consisting of a methicillin-resistant *Staphylococcus aureus* (MRSA), an oxacillin-resistant *Staphylococcus aureus* (ORSA), a vancomycin-resistant *Staphylococcus aureus* (VRSA) and a vancomycin intermediate *Staphylococcus aureus* (VISA).

According to some of the respective embodiments of the invention, the crystallized large ribosomal subunit is characterized by a crystal space group of P6522 and a unit cell dimensions of a=279.8±10 Å, b=279.8±10 Å, c=872.8±10 Å, $\alpha$=90, $\beta$=90 and $\gamma$=120.

According to some of the respective embodiments of the invention, the crystallized large ribosomal subunit is characterized by the atomic coordinates deposited at the Protein Data Bank under accession number PDB ID: 4WCE.

According to some of any of the embodiments of the invention, a ligand is bound to the large ribosomal subunit to thereby form a crystallized complex of the subunit and the ligand.

According to some of the respective embodiments of the invention, the ligand is an antibacterial agent. According to some embodiments of the invention, the ligand is linezolid.

According to some of the respective embodiments of the invention, the crystallized complex is characterized by a crystal space group of P6522 and a unit cell dimensions of a=279.9±10 Å, b=279.9±10 Å, c=870.6±10 Å, $\alpha$=90, $\beta$=90 and $\gamma$=120.

According to some of the respective embodiments of the invention, the crystallized complex is characterized by the atomic coordinates deposited at the Protein Data Bank under accession number PDB ID: 4WFA.

According to some embodiments of the invention, the ligand is BC-3205.

According to some of the respective embodiments of the invention, the crystallized complex is characterized by a crystal space group of P6522 and a unit cell dimensions of a=280.9±10 Å, b=280.9±10 Å, c=875.6±10 Å, $\alpha$=90, $\beta$=90 and $\gamma$=120.

According to some of the respective embodiments of the invention, the crystallized complex is characterized by the atomic coordinates deposited at the Protein Data Bank under accession number PDB ID: 4WFB.

According to some embodiments of the invention, the ligand is telithromycin.

According to some of the respective embodiments of the invention, the crystallized complex is characterized by a crystal space group of P6522 and a unit cell dimensions of a=282.7±10 Å, b=282.7±10 Å, c=877.1±10 Å, $\alpha$=90, $\beta$=90 and $\gamma$=120.

According to some of the respective embodiments of the invention, the crystallized complex is characterized by the atomic coordinates deposited at the Protein Data Bank under accession number PDB ID: 4WF9.

According to some embodiments of the invention, the ligand is lefamulin.

According to some of the respective embodiments of the invention, the crystallized complex is characterized by a crystal space group of P6522 and a unit cell dimensions of a=282.1±10 Å, b=282.1±10 Å, c=875.3±10 Å, $\alpha$=90, $\beta$=90 and $\gamma$=120.

According to some of the respective embodiments of the invention, the crystallized complex is characterized by the atomic coordinates deposited at the Protein Data Bank under accession number PDB ID: 5HL7.

According to some embodiments of the invention, the ligand is lincomycin.

According to some of the respective embodiments of the invention, the crystallized complex is characterized by a crystal space group of P6522 and a unit cell dimensions of a=280.8±10 Å, b=280.8±10 Å, c=873.5±10 Å, $\alpha$=90, $\beta$=90 and $\gamma$=120.

According to some of the respective embodiments of the invention, the crystallized complex is characterized by the atomic coordinates deposited at the Protein Data Bank under accession number PDB ID: 5HKV.

According to an aspect of some embodiments of the present invention there is provided a computer system which includes:

(a) a data-storage device having stored therein positioning data indicative of atomic coordinates determined from an electron density map having a resolution of at least 4 Å calculated from X-rays diffraction data obtained using at least one of any of the compositions-of-matter described herein;

(b) a processing unit in electrical communication with the data-storage device and operating; and (c) a program for calculating a three-dimensional model representative of the large ribosomal subunit from the positioning data.

According to some embodiments of the invention, the computer system further includes a device for providing a visual representation of the model.

According to some of the respective embodiments of the invention, the positioning data comprise at least a portion of the atomic coordinates deposited at the Protein Data Bank under accession numbers that include PDB IDs: 4WCE, 4WFA, 4WFB, 4WF9, 5HL7 and 5HKV.

According to some of any of the respective embodiments of the invention, the atomic coordinates define at least a portion of a ligand bound to the large ribosomal subunit.

According to some of any embodiments of the invention, the ligand is selected from the group consisting of linezolid, BC-3205, telithromycin, lefamulin and lincomycin.

According to some of any of the respective embodiments of the invention, the positioning data comprise at least a portion of the atomic coordinates deposited at the Protein Data Bank under accession number selected from the group consisting of PDB IDs: 4WFA (linezolid), 4WFB (BC-3205) and 4WF9 (telithromycin), 5HL7 (lefamulin) and 5HKV (lincomycin).

According to some of any of the respective embodiments of the invention, the atomic coordinates are produced by molecular replacement using at least a portion of the atomic coordinates of another large ribosomal subunit.

According to some embodiments of the invention, the atomic coordinates of the other large ribosomal subunit used for molecular replacement are deposited at the Protein Data Bank under accession number PDB ID: 2ZJR.

According to some of any of the respective embodiments of the invention, the atomic coordinates comprise atomic coordinates of at least one ribosomal RNA (rRNA).

According to some of any of the respective embodiments of the invention, the atomic coordinates comprise atomic coordinates of at least one ribosomal protein (rProtein).

According to some of any of the respective embodiments of the invention, the atomic coordinates comprise at least a portion of at least one binding site in the large ribosomal subunit.

According to some of any of the respective embodiments of the invention, the binding site is selected from the group consisting of an inter-subunit interface, a peptidyl transferase site, a GTPase center, an mRNA binding site, an A-site, a P-site, an E-site, a polypeptide exit tunnel, a translation initiation factor (IF1) binding site, a translation initiation factor (IF2) binding site, a translation initiation factor (IF3) binding site, an elongation factor G (EF-G) binding site, elongation factor Tu (EF-Tu) binding site, hibernation factor HPF binding site, hibernation factor RMF binding site, hibernation factor YfiA binding site, a GTP binding site and a ricin binding site.

According to some of any of the respective embodiments of the invention, the atomic coordinates further comprise at least a portion of at least one of the following, mRNA, tRNA, activated tRNA and a polypeptide under translation.

According to some embodiments of the invention, the computer system further includes a computer-aided drug design program or computer-aided drug design software suite for calculating and designing a structure of a putative ligand for binding to one of the binding sites.

According to some of any of the respective embodiments of the invention, the computer system further includes atomic coordinates of a putative ligand for binding to the binding site in the large ribosomal subunit of the pathogenic bacterium, the computer-aided drug design is a structure-based drug design, and the putative ligand is designed based on a structure of the binding site in the large ribosomal subunit provided herein.

According to some embodiments of the invention, the computer system further includes the data-storage device further stores:

(i) sequence data indicative of at least a portion of the amino acids and at least a portion of the ribonucleic acids of the large ribosomal subunit;

(ii) positioning data indicative of atomic coordinates of at least a portion of a large ribosomal subunit of at least one different organism; and (iii) sequence data indicative of at least a portion of the amino acids and at least a portion of the ribonucleic acids of the large ribosomal subunit of the at least one different organism.

According to some embodiments of the invention, the computer system further includes:

(d) a sequence alignment program for calculating a residue correlation data of the amino acids and the ribonucleic acids of at least two large ribosomal subunits of at least two different organisms provided that at least one of the at least two different organisms is the pathogenic bacterium; and (e) a structure alignment program for superimposing the atomic coordinates of the at least two large ribosomal subunits based on the residue correlation data.

According to some of any of the respective embodiments of the invention, the different organism is selected from the group consisting of *Thermus thermophilus, Escherichia coli, Haloarcula marismortui, Deinococcus radiodurans* and *Saccharomyces cerevisiae, Tetrahymena thermophila*.

According to some of any of the respective embodiments of the invention, the atomic coordinates of the *D. radiodurans* comprise at least a portion of the atomic coordinates deposited at the Protein Data Bank under accession number selected from the group consisting of PDB IDs: 2ZJR, 3DLL, 2OGM, 2OGN, 2OGO, 1XNP, 1SM1, 1P9X, 1JZX, 1JZY and 4U67.

According to some of any of the respective embodiments of the invention, the atomic coordinates of the *E. coli* comprise at least a portion of the atomic coordinates deposited at the Protein Data Bank under accession number selected from the group consisting of PDB IDs: 2AW4, 3R8S, 3OAT, 3OFZ and 3OFR.

According to some of any of the respective embodiments of the invention, the atomic coordinates of the *T. thermophilus* comprise at least a portion of the atomic coordinates deposited at the Protein Data Bank under accession number selected from the group consisting of PDB IDs: 2WDL, 2WDK, 3OI3 and 3OHD.

According to some of any of the respective embodiments of the invention, the atomic coordinates of the *H. marismortui* comprise at least a portion of the atomic coordinates deposited at the Protein Data Bank under accession number selected from the group consisting of PDB ID: 1S72, 3CC2 3CPW, 1YJN and 1YIJ.

According to some of any of the respective embodiments of the invention, the atomic coordinates of the *T. thermophila* comprise at least a portion of the atomic coordinates deposited at the Protein Data Bank under accession number selected from the group consisting of PDB ID: 4A17, 4A18, 4A19, 4A1A, 4A1B, 4A1C, 4A1D and 4A1E.

According to some of any of the respective embodiments of the invention, the atomic coordinates of the *S. cerevisiae* comprise at least a portion of the atomic coordinates deposited at the Protein Data Bank under accession number selected from the group consisting of PDB ID: 3U5B, 3U5C, 3U5D, 3U5E, 3U5F, 3U5G, 3U5H and 3U5I.

According to some of any of the respective embodiments of the invention, the different organism is a host of the pathogenic bacterium, thereby allowing calculating positioning data indicative of atomic coordinates of the large ribosomal subunit of the host organism based on the residue correlation data.

According to some of any of the respective embodiments of the invention, the host organism is a mammal and the pathogenic bacterium is a pathogen of the mammal.

According to some of any of the respective embodiments of the invention, the mammal is a human.

According to some of any of the respective embodiments of the invention, the data-storage device further includes at least a portion of the atomic coordinates of a ribosomal subunit of a human.

According to some of any of the respective embodiments of the invention, the atomic coordinates of a ribosomal subunit of a human are afforded by a method selected from the group consisting of X-ray crystallography, NMR, molecular modeling, single-particle cryogenic electron microscopy and X-ray free-electron laser.

According to some of any of the respective embodiments of the invention, the computer system further includes atomic coordinates of a species-selective putative ligand for binding to the binding site in the large ribosomal subunit of the pathogenic bacterium, the computer-aided drug design is a structure-based drug design, and the putative ligand is designed based on a structure of the binding site in the large ribosomal subunit provided herein.

According to an aspect of some embodiments of the present invention there is provided a computer readable medium which includes retrievable positioning data indicative of atomic coordinates determined from an electron density map having a resolution of at least 4 Å calculated from X-rays diffraction data obtained using the composition-of-matter according to any of the respective embodiments of the present invention.

According to some embodiments of the invention, the atomic coordinates deposited at the Protein Data Bank under accession number selected from the group consisting of PDB IDs: 4WCE, 4WFA, 4WFB, 4WF9, 5HL7 and 5HKV.

According to some embodiments of the invention, the computer readable medium further includes atomic coordinates of at least a portion of a large ribosomal subunit of *D. radiodurans* deposited at the Protein Data Bank under accession number selected from the group consisting of PDB IDs: 2ZJR, 3DLL, 2OGM, 2OGN, 2OGO, 1XNP, 1SM1, 1P9X, 1JZX, 1JZY and 4U67.

According to some embodiments of the invention, the computer readable medium further includes atomic coordinates of at least a portion of a large ribosomal subunit of *E. coli* deposited at the Protein Data Bank under accession number selected from the group consisting of PDB IDs: 2AW4, 3R8S, 3OAT, 3OFZ and 3OFR.

According to some embodiments of the invention, the computer readable medium further includes atomic coordinates of at least a portion of a large ribosomal subunit of *T. thermophilus* deposited at the Protein Data Bank under accession number selected from the group consisting of PDB IDs: 2WDL, 2WDK, 3OI3 and 3OHD.

According to some embodiments of the invention, the computer readable medium further includes atomic coordinates of at least a portion of a large ribosomal subunit of *H. marismortui* deposited at the Protein Data Bank under accession number selected from the group consisting of PDB IDs: 1S72, 3CC2 3CPW, 1YJN and 1YIJ.

According to some embodiments of the invention, the computer readable medium further includes atomic coordinates of at least a portion of a large ribosomal subunit of *T. thermophila* deposited at the Protein Data Bank under accession number selected from the group consisting of PDB IDs: 4A17, 4A18, 4A19, 4A1A, 4A1B, 4A1C, 4A1D and 4A1E.

According to some embodiments of the invention, the computer readable medium further includes atomic coordinates of at least a portion of a large ribosomal subunit of *S. cerevisiae* deposited at the Protein Data Bank under accession number selected from the group consisting of PDB IDs: 3U5B, 3U5C, 3U5D, 3U5E, 3U5F, 3U5G, 3U5H and 3U5I.

According to some embodiments of the invention, the computer readable medium further includes atomic coordinates of at least a portion of a large ribosomal subunit of a human afforded by a method selected from the group consisting of molecular modeling, single-particle cryogenic electron microscopy and X-ray free-electron laser.

According to some of any of the respective embodiments of the invention, the computer readable medium further includes sequence data indicative of at least a portion of the amino acids and at least a portion of the ribonucleic acids of the large ribosomal subunit.

According to some of any of the respective embodiments of the invention, the computer readable medium further includes sequence data indicative of at least a portion of the amino acids and at least a portion of the ribonucleic acids of a large ribosomal subunit of a host organism.

According to some of any of the respective embodiments of the invention, the computer readable medium further includes positioning data indicative of atomic coordinates of the large ribosomal subunit of the host organism.

According to some of the respective embodiments of the invention, the host organism is a mammal and the pathogenic bacterium is a pathogen of the mammal.

According to some of the respective embodiments of the invention, the mammal is a human.

According to an aspect of some embodiments of the present invention there is provided a method for designing a putative ligand having an affinity to a binding site of a large ribosomal subunit of a pathogenic bacterium, the method is effected by:

(a) obtaining positioning data indicative of atomic coordinates of at least one binding site determined from an electron density map having a resolution of at least 4 Å calculated from X-rays diffraction data obtained using at least one of the composition-of-matter according to any of the respective embodiments of the present invention;

(b) calculating a molecular surface of the binding site; and (c) computationally constructing a chemically feasible ligand having a molecular surface that match the molecular surface of the binding site.

According to some embodiments of the invention, the method further includes, prior to step (b), determining the binding site in the large ribosomal subunit using the positioning data (atomic coordinates) of at least a portion of a ligand bound to the large ribosomal subunit, wherein the binding site being in association with the ligand (a target-bound ligand).

According to some embodiments of the invention, the method further includes, prior to step (c): computationally constructing a library of structures of chemically feasible ligands having a molecular surface that matches the molecular surface of the binding site.

According to some embodiments of the invention, the method further includes:

(d) computationally determining a matching score for each of the ligands; and (e) based on the matching score selecting at least one putative ligand having the desired affinity to the binding site of the large ribosomal subunit of a pathogenic bacterium.

According to some embodiments of the invention, the method further includes, prior to step (d), adding to the library a plurality of structures of chemically feasible variants of pre-existing ligands.

According to some embodiments of the invention, the method further includes, prior to step (c), calculating a molecular surface of at least a portion of the binding site of a large ribosomal subunit of a different organism.

According to some of any of the respective embodiments of the invention, the different organism used in the method for designing a putative ligand, is selected from the group consisting of a host of the pathogenic bacterium and a benign microorganism.

According to some embodiments of the invention, step (c) of the method further includes computationally constructing a chemically feasible ligand having a molecular surface that matches the molecular surface of the binding site of the large ribosomal subunit of a pathogenic bacterium, and mismatches at least one feature in the molecular surface of the binding site in the of a large ribosomal subunit of the different organism.

According to some of the respective embodiments of the invention, the active site considered in the method is selected from the group consisting of a inter-subunit interface, a peptidyl transferase site, a GTPase center, an mRNA binding site, an A-site, a P-site, an E-site, a polypeptide exit tunnel, a translation initiation factor (IF1) binding site, a translation initiation factor (IF2) binding site, a translation initiation factor (IF3) binding site, an elongation factor G (EF-G) binding site, elongation factor Tu (EF-Tu) binding site, hibernation factor HPF binding site, hibernation factor RMF binding site, hibernation factor YfiA binding site, a GTP binding site and a ricin binding site.

According to some of any of the respective embodiments of the invention, the ligand has a molecular weight of less than 1,500 g/mol.

According to some of any of the respective embodiments of the invention, the method further includes, subsequent to step (c), preparing (e.g., synthesizing) the ligand.

According to some of any of the respective embodiments of the invention, the method further includes contacting the ligand with the large ribosomal subunit of the pathogenic bacterium.

In some embodiments of the invention, contacting the ligand with the large ribosomal subunit is effected in an activity assay which also produces a binding score.

According to an aspect of some embodiments of the present invention there is provided a ligand having an affinity to a molecular surface of at least a portion of a binding site of a large ribosomal subunit of a pathogenic bacterium designed by the method for designing a putative ligand, according to any of the respective embodiments of the present invention.

According to some embodiments of the invention, the ligand is a protein synthesis inhibitor.

According to some embodiments of the invention, the ligand is a protein synthesis inhibitor that includes:

a first binding moiety having a molecular surface that mimics or duplicates a molecular surface of a first pre-existing ligand that binds to a first binding site in a large ribosomal subunit; and at least one second binding moiety having a molecular surface that mimics or duplicates a surface of a second pre-existing ligand that binds with a second binding site in the ribosomal subunit, wherein:

the first pre-existing ligand is different than the second pre-existing ligand;

the first binding site is different than the second binding site;

the first binding moiety is attached to the second binding moiety via a linking moiety so as to permit both the first moiety and the second moiety to bind simultaneously each with its respective binding site thereby disrupting protein synthesis in a ribosomal subunit.

According to some of the respective embodiments of the invention, the protein synthesis inhibitor has a molecular weight of less than about 1,500 g/mol.

According to some of the respective embodiments of the invention, the affinity constant of the ligand with respect to the ribosomal subunit is greater than each of the affinity constants of the first pre-existing ligand and the second pre-existing ligand.

According to some of the respective embodiments of the invention, the pre-existing ligand is an antibacterial agent.

According to some of the respective embodiments of the invention, each of the first pre-existing ligand and the second pre-existing ligand is selected from the group consisting of linezolid, BC-3205, telithromycin, lefamulin and lincomycin.

According to an aspect of some embodiments of the present invention there is provided a ligand which includes:

a first binding moiety having a molecular surface that mimics or duplicates a molecular surface of a first pre-existing ligand that binds to a first binding site in a large ribosomal subunit; and a second binding moiety having a molecular surface that mimics or duplicates a surface of a second pre-existing ligand that binds with a second binding site in the ribosomal subunit, wherein:

the first pre-existing ligand is not the second pre-existing ligand;

the first binding site is not the second binding site;

the first binding moiety is attached to the second binding moiety via a linking moiety so as to permit both the first moiety and the second moiety to bind simultaneously each with its respective binding site thereby disrupting protein synthesis in a ribosomal subunit, wherein a positioning data of the first binding moiety relative to a positioning data of the second binding moiety, is determined according to atomic coordinates indicative of a positioning data of the first binding moiety and the second binding moiety obtained from an electron density map having a resolution of at least 4 Å calculated from X-rays diffraction data obtained using at least one of the composition-of-matter according to any of the respective embodiments of the present invention.

According to some of the respective embodiments of the invention, the protein synthesis inhibitor has a molecular weight of less than about 1,500 g/mol.

According to some of the respective embodiments of the invention, the affinity constant of the ligand with respect to the ribosomal subunit is greater than each of an affinity constant of the first pre-existing ligand and the second pre-existing ligand.

According to some of the respective embodiments of the invention, the pre-existing ligand is an antibacterial agent.

According to some of the respective embodiments of the invention, each of the first pre-existing ligand and the second pre-existing ligand is selected from the group consisting of linezolid, BC-3205, telithromycin, lefamulin and lincomycin.

According to some of the respective embodiments of the invention, the ribosomal subunit is a large ribosomal subunit of a pathogenic Gram positive bacterium.

According to some of the respective embodiments of the invention, the ligand is a pathogenic Gram positive bacterium-specific protein synthesis inhibitor.

According to some of the respective embodiments of the invention, the pathogenic Gram positive bacterium is *Staphylococcus aureus*.

According to an aspect of some embodiments of the present invention there is provided a pharmaceutical composition which includes, as an active ingredient, the ligand according to any of the respective embodiments of the invention, and a pharmaceutically acceptable carrier.

According to some embodiments of the invention, the pharmaceutical composition is packaged in a packaging material and identified in print, in or on the packaging material, for use in the treatment of an infection associated with a pathogenic bacterium, wherein the pathogenic bacterium is Gram positive and/or exhibiting a degree of 23S rRNA sequence identity of at least 80% compared to rRNA of *Staphylococcus aureus* and a degree of 23S rRNA sequence identity of less than 99.9% compared to rRNA of *Escherichia coli*.

According to an aspect of some embodiments of the present invention there is provided a method of treating an infection associated with a pathogenic bacterium, the method is effected by administering to a subject in need thereof, e.g., a human, a therapeutically effective amount of a ligand according to any of the respective embodiments of the present invention, wherein the pathogenic bacterium is Gram positive and/or exhibiting a degree of 23S rRNA sequence identity of at least 80% compared to rRNA of *Staphylococcus aureus* and a degree of 23S rRNA sequence identity of less than 99.9% compared to rRNA of *Escherichia coli*.

According to an aspect of some embodiments of the present invention there is provided a method of obtaining the composition-of-matter according to any of the respective embodiments of the present invention, the method is effected by:

(a) subjecting a crystallization solution that includes a concentrated purified preparation of the large ribosomal subunit of the pathogenic bacterium to vapor diffusion conditions against a reservoir solution for a first time period;

(e) transferring at least one macro crystal to a stabilization solution, to thereby obtain a crystal of the large ribosomal subunit of the pathogenic bacterium capable of diffracting X-ray to resolution of at least 4 Å.

According to some embodiments of the present invention, the method of obtaining the composition-of-matter further includes, prior to step (e):

(b) extracting a plurality of seeding crystals from the crystallization solution;

(c) transferring at least one of the seeding crystals into the crystallization solution; and (d) subjecting the crystallization solution that includes the seeding crystals to vapor diffusion conditions against the reservoir solution for a second time period.

According to some embodiments of the present invention, the concentrated purified preparation is prepared by concentrating a fraction of a zonal ultracentrifugation using a sucrose gradient.

According to some of any of the respective embodiments of the present invention, the concentrated purified preparation is characterized by an optical absorbance at 260 nm (A260) of 600-1000 per ml.

According to some of any of the respective embodiments of the present invention, vapor diffusion conditions include a drop of the crystallization solution applied substantially at the center and bottom of an air-tight lid that closes a top opening of a container which includes the reservoir solution.

According to some of any of the respective embodiments of the present invention, the crystallization solution comprises the concentrated purified preparation at a concentration of 0.9-1.6 mg/ml, 0.1-0.2 percent by weight 2-methyl-2,4-pentanediol, 0.3-0.4 percent by weight ethanol, 4-6 mM spermidine, 0.4-0.6 mM $MnCl_2$, 20 mM Hepes buffer set to pH range of 6.8-7.8, 10 mM $MgCl_2$, 60 mM $NH_4Cl$ and 15 mM KCl.

According to some of any of the respective embodiments of the present invention, the reservoir solution comprises 4-6 percent by weight 2-methyl-2,4-pentanediol, 8-12 percent by weight ethanol, 110 mM Hepes buffer set to pH range of 6.8-7.8, 10 mM $MgCl_2$, 60 mM $NH_4Cl$ and 15 mM KCl.

According to some of any of the respective embodiments of the present invention, the stabilization solution comprises 10-25 percent by weight 2-methyl-2,4-pentanediol, 10-20 percent by weight ethanol, 110 mM Hepes buffer set to pH range of 6.8-7.8, 10 mM $MgCl_2$, 60 mM $NH_4Cl$ and 15 mM KCl.

According to some embodiments of the present invention, step (c) of the method of obtaining the composition-of-matter, if present, further includes, prior to the transferring, washing the seeding crystals in a solution that includes 7-8 percent by weight 2-methyl-2,4-pentanediol, 7-8 percent by weight ethanol, 110 mM Hepes buffer set to pH range of 6.8-7.8, 10 mM $MgCl_2$, 60 mM $NH_4Cl$ and 15 mM KCl buffer and 0.5 mM $MnCl_2$.

According to some embodiments of the present invention, the method of obtaining the composition-of-matter further includes, prior to step (a), heating the concentrated purified preparation of the large ribosomal subunit for 20-40 minutes at 37° C.

According to some embodiments of the present invention, the first time period ranges from 10 days to 20 days.

According to some embodiments of the present invention, the second time period, if present, ranges from 2 weeks to 4 weeks.

According to some embodiments of the present invention, each of any one of steps (a)-(e) of the method of obtaining the composition-of-matter, if present, is effected at a temperature that ranges from 18° C. to 22° C.

According to some embodiments of the present invention, the method of obtaining the composition-of-matter further comprises:

(f) transferring at least one macro crystal from the stabilization solution to a soaking solution that includes a ligand dissolved in the stabilization solution; and (g) maintaining the crystal in the soaking solution for a third time period that ranges from 1 day to 10 days.

According to some embodiments of the present invention, the third time period ranges from 2 hours to 24 hours prior to exposing the crystal having the ligand soaked therein to X-ray.

According to some embodiments of the present invention, the concentration of the ligand in the soaking solution ranges from 1 μg/ml to 30 μg/ml.

According to some of any of the respective embodiments of the present invention, the ligand is an antibacterial agent.

According to some of any of the respective embodiments of the present invention, the antibacterial agent is selected from the group consisting of linezolid, BC-3205 and telithromycin.

According to an aspect of some embodiments of the present invention there is provided a crystal of a large ribosomal subunit of a pathogenic bacterium produced by the method according to any of the respective embodiments of the invention.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, computer systems or otherwise any hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform or system for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 3A:
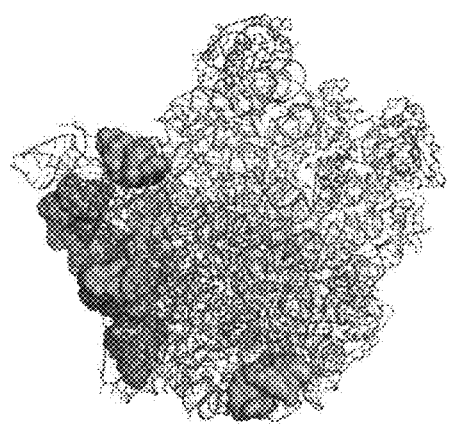
Figure 3A:
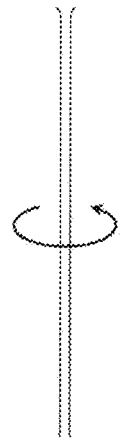
Figure 3B:
Figure 4A:
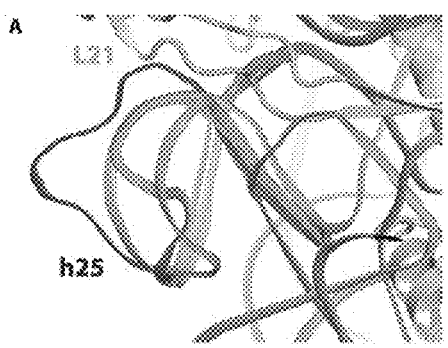
Figure 4B:
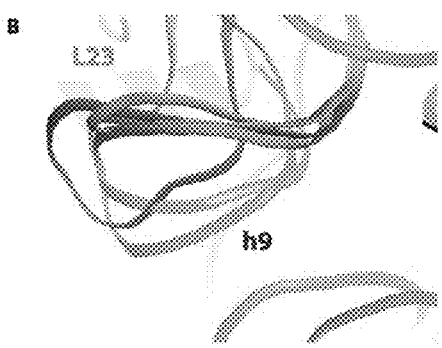
Figure 4C:
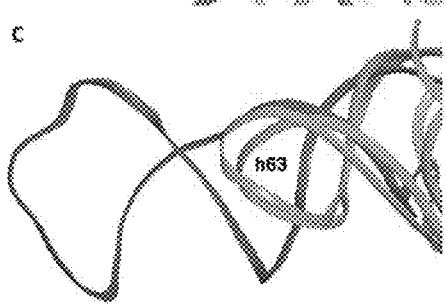
Figure 4D:
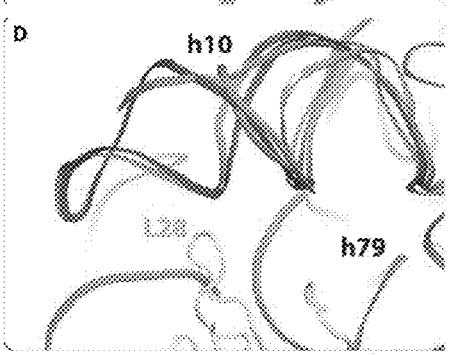
Figure 4E:
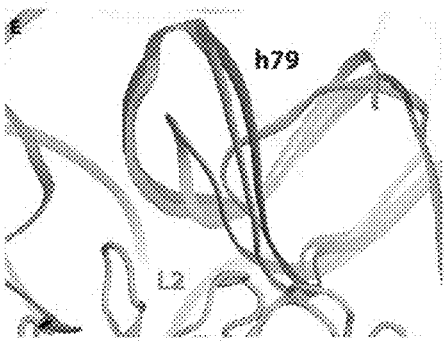
Figure 4F:
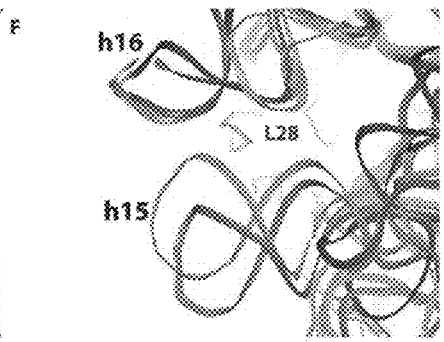
Figure 4G:
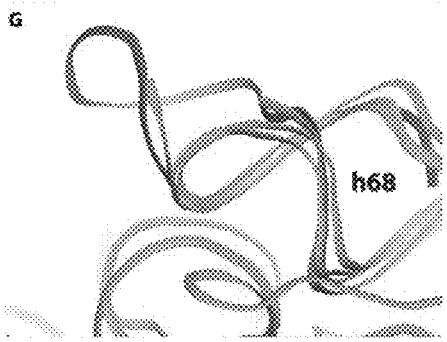
Figure 4H:
Figure 5A:
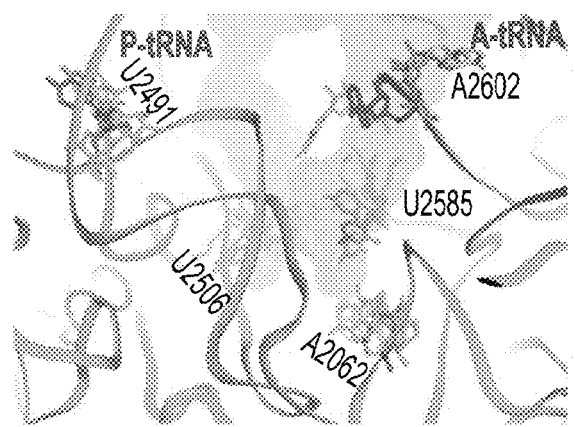
Figure 5B:
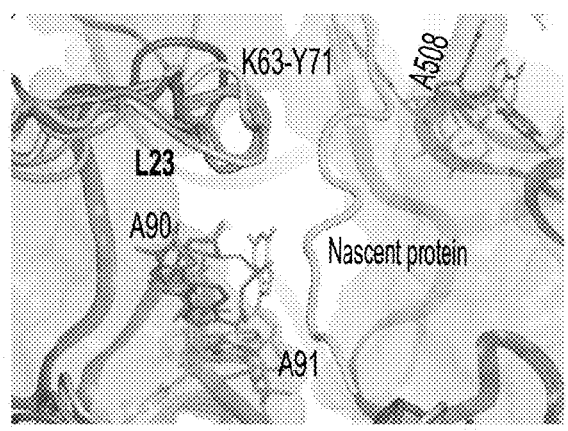
Figure 6A:
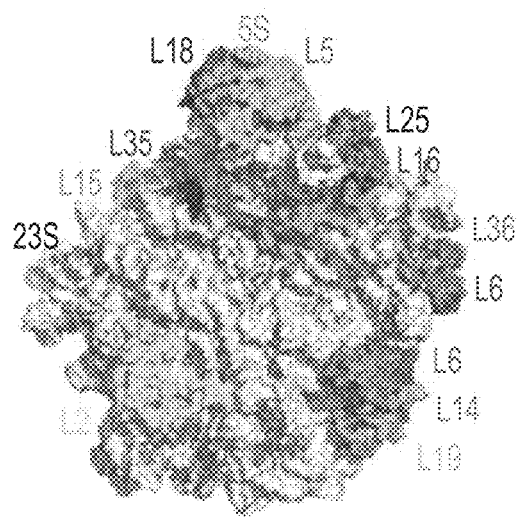
Figure 6B:
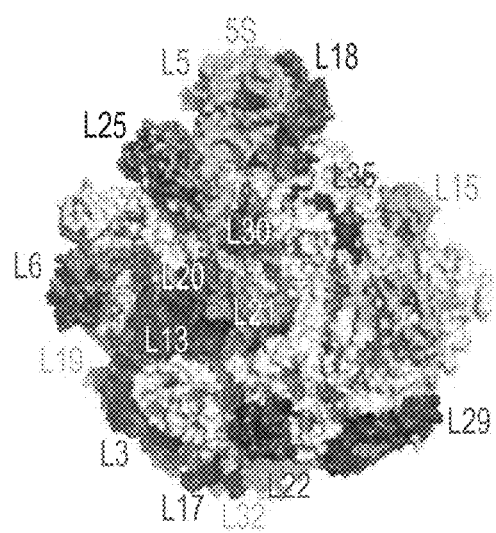
Figure 6C:
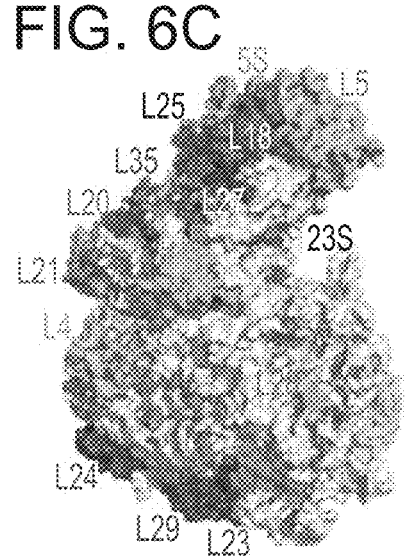
Figure 6D:
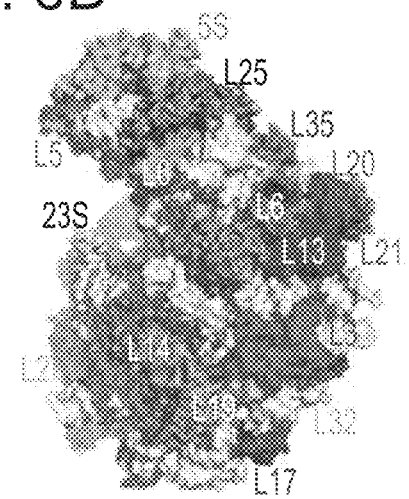
Figure 7A:
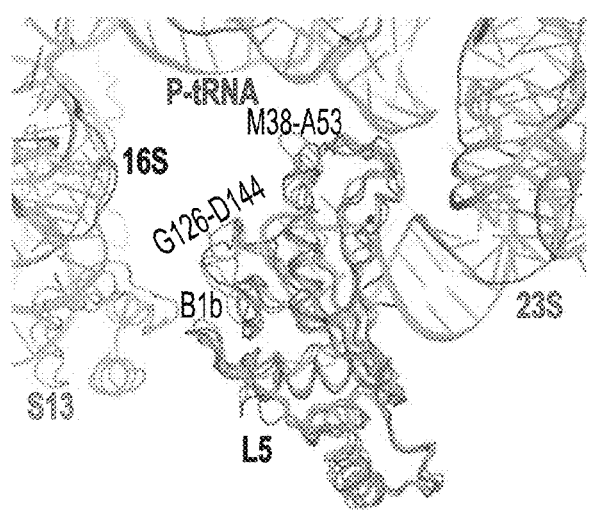
Figure 7B:
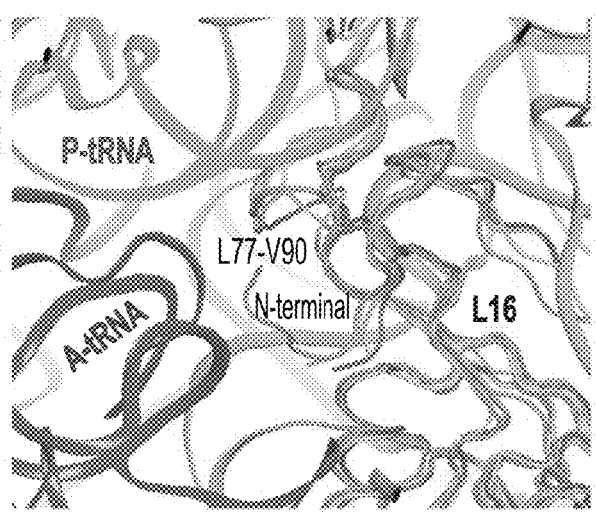
Figure 8A:
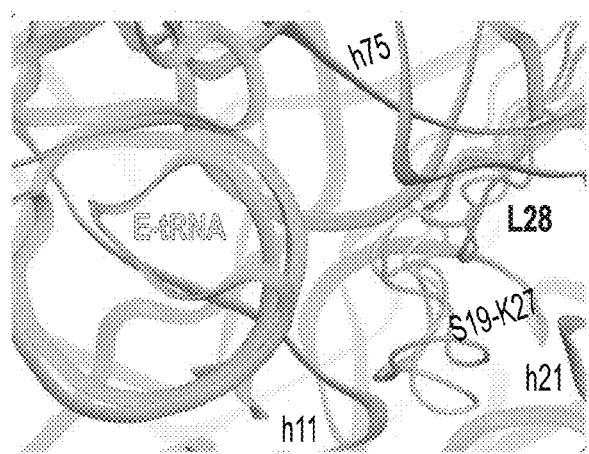
Figure 8B:
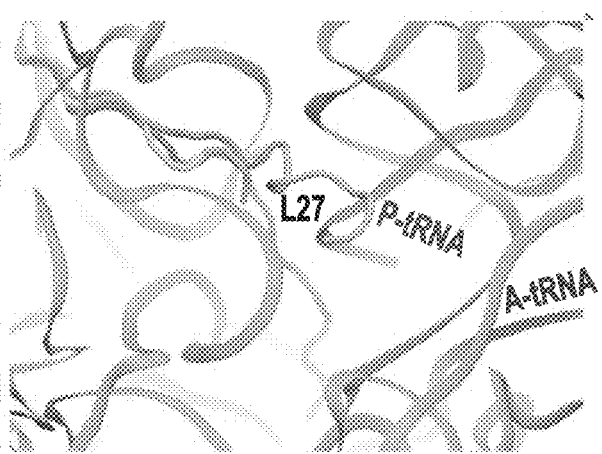
Figure 10A:
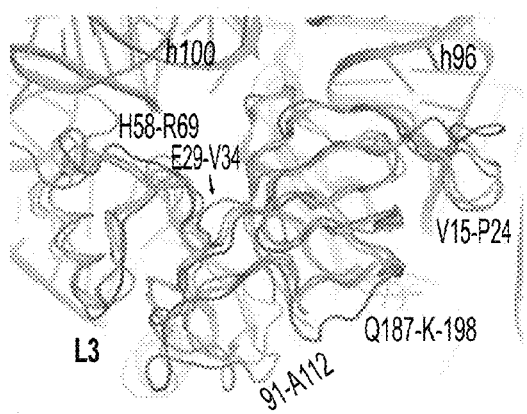
Figure 10B:
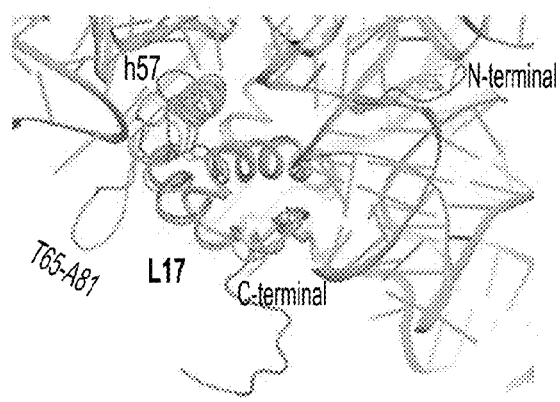
Figure 10C:
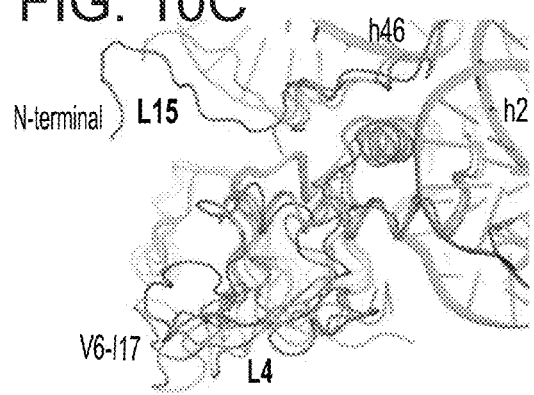
Figure 10D:
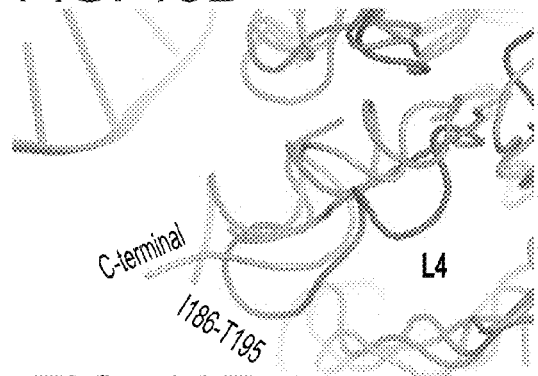
Figure 10E:
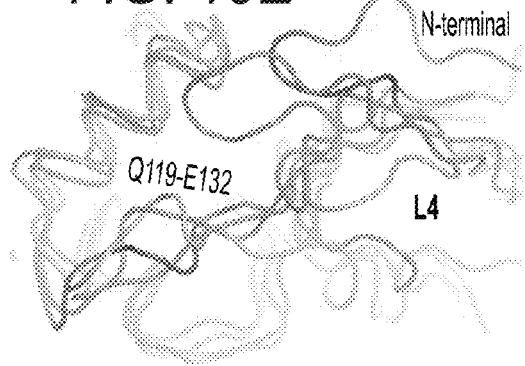
Figure 10F:
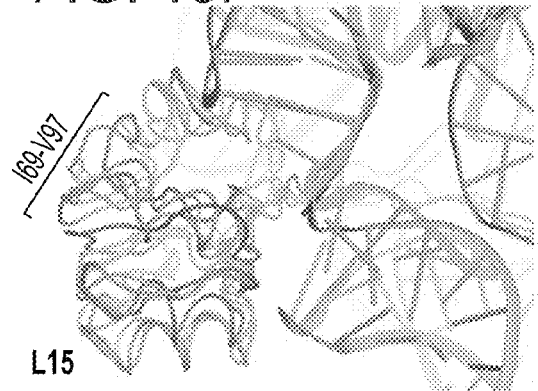
Figure 10G:
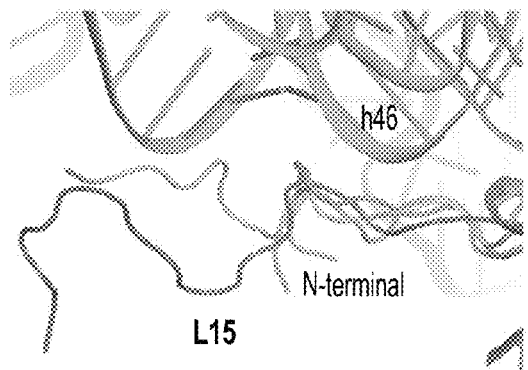
Figure 10H:
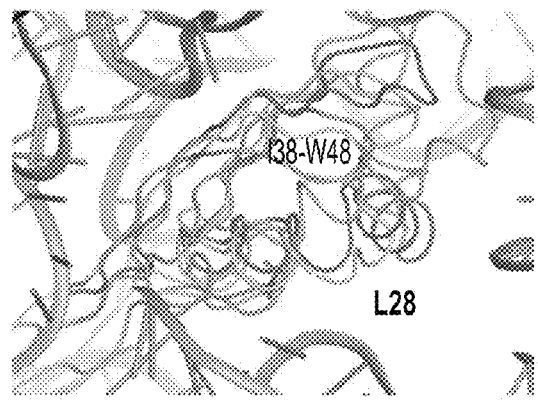
Figure 11A:
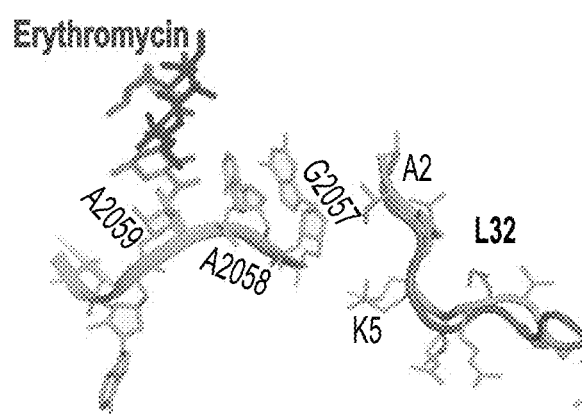
Figure 11B:
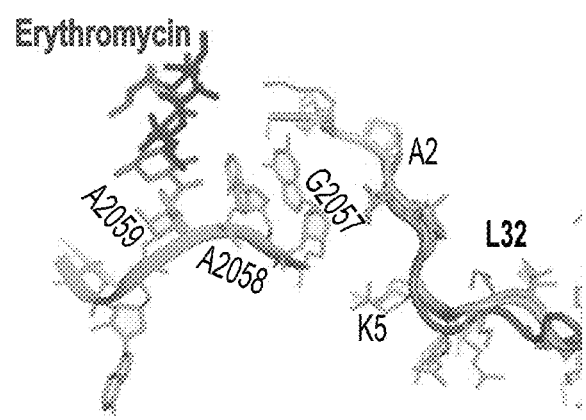
Figure 12A:
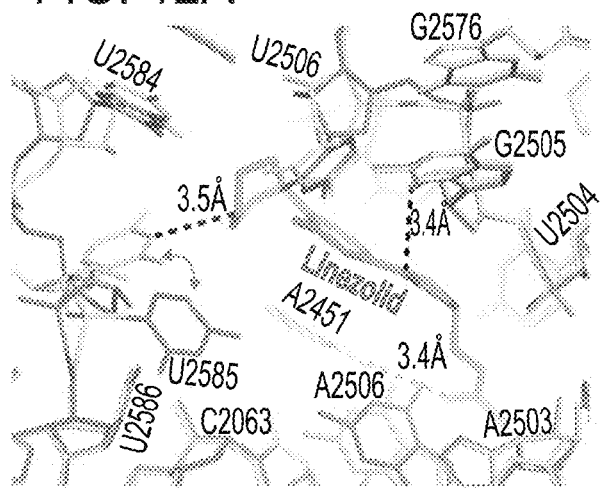
Figure 12B:
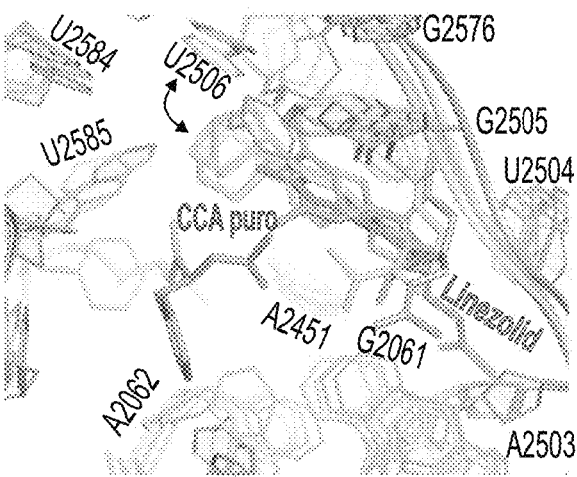
Figure 12C:
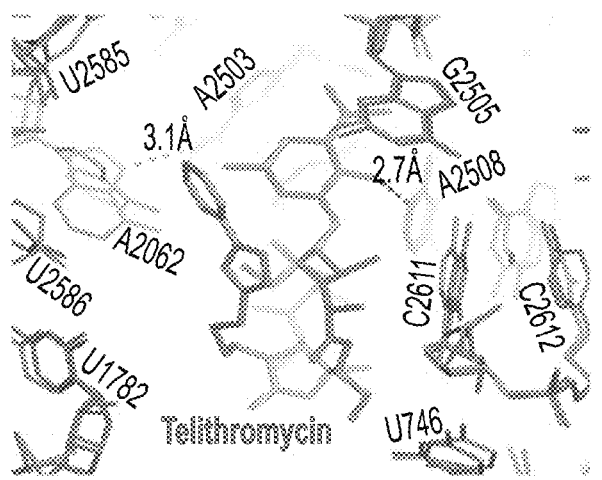
Figure 12D:
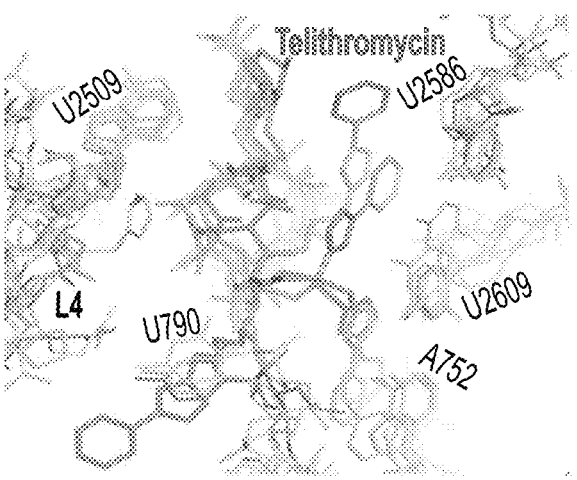
Figure 12E:
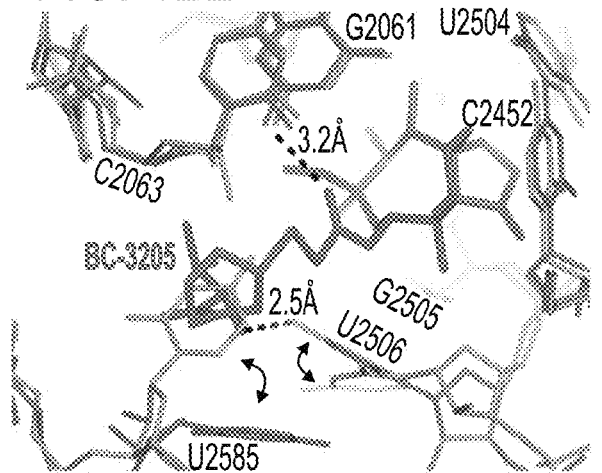
Figure 12F:
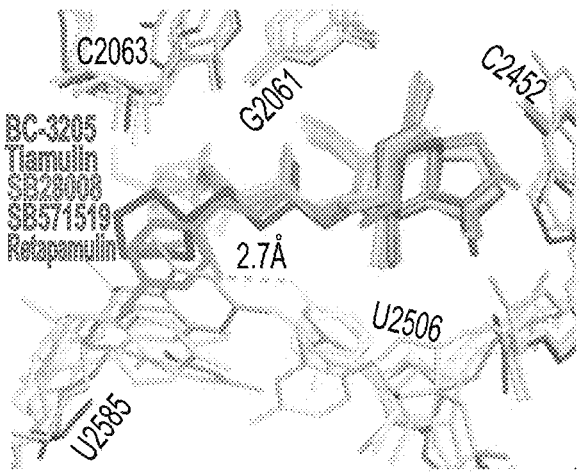
Figure 13A:
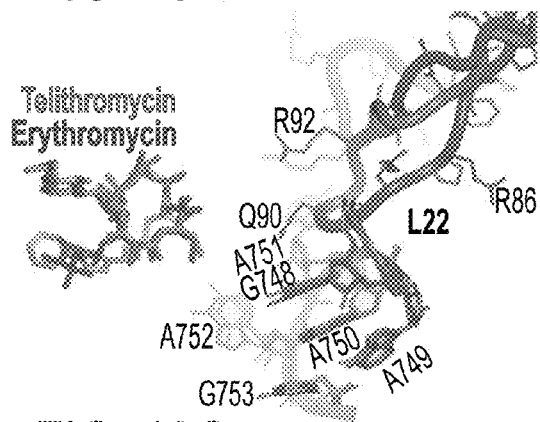
Figure 13B:
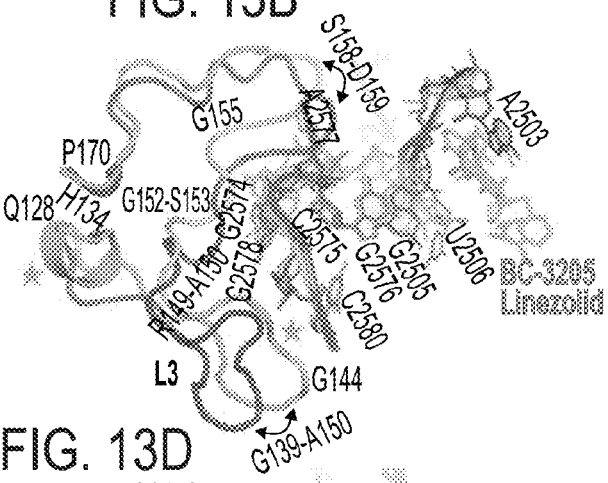
Figure 13C:
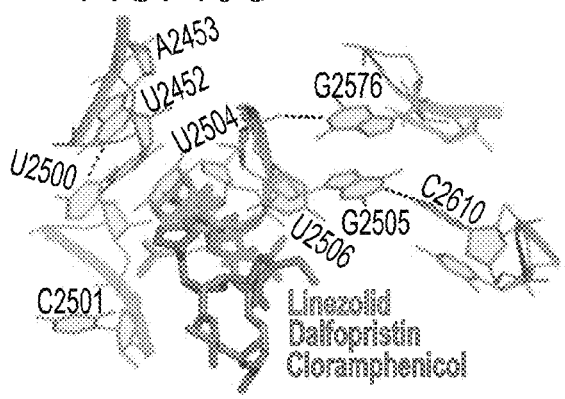
Figure 13D:
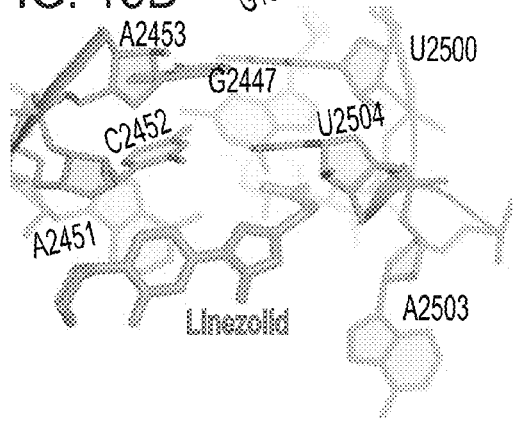
Figure 13E:
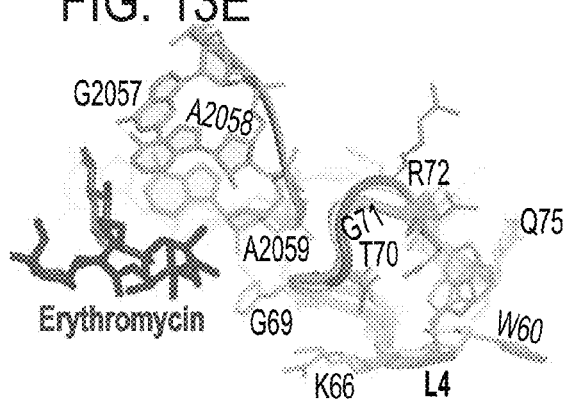
Figure 13F:
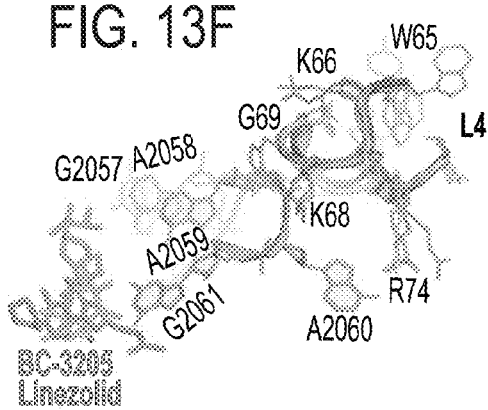
Figure 14A:
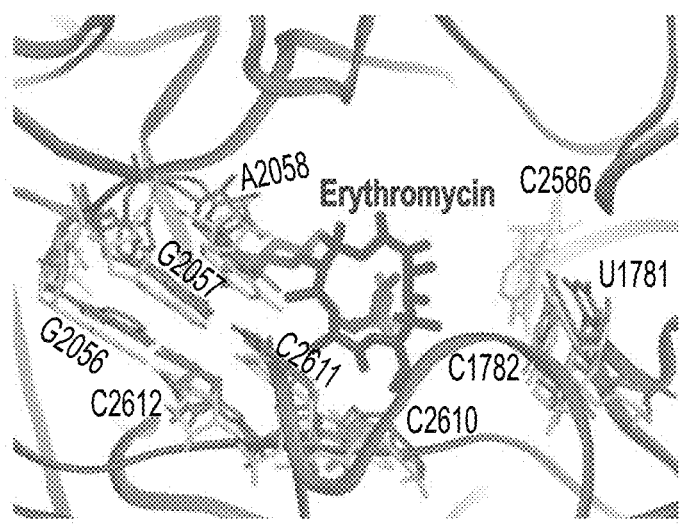
Figure 14B:
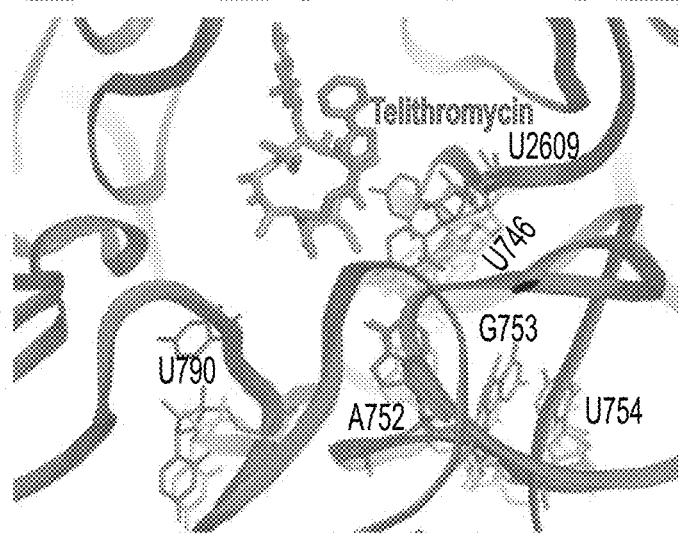
Figure 14C:
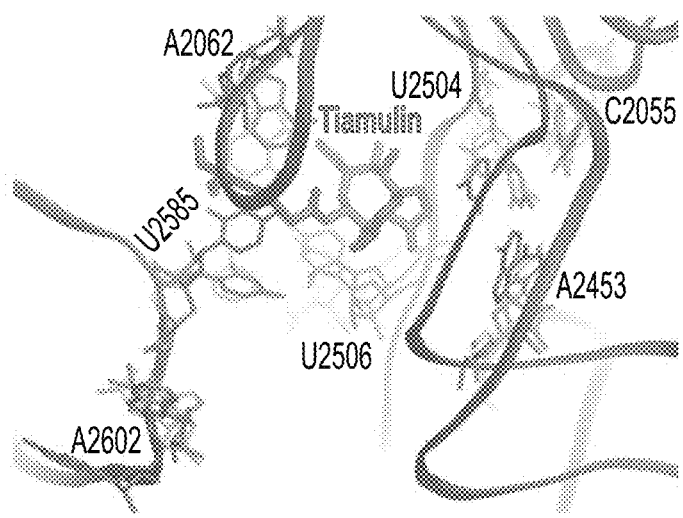
Figure 15:
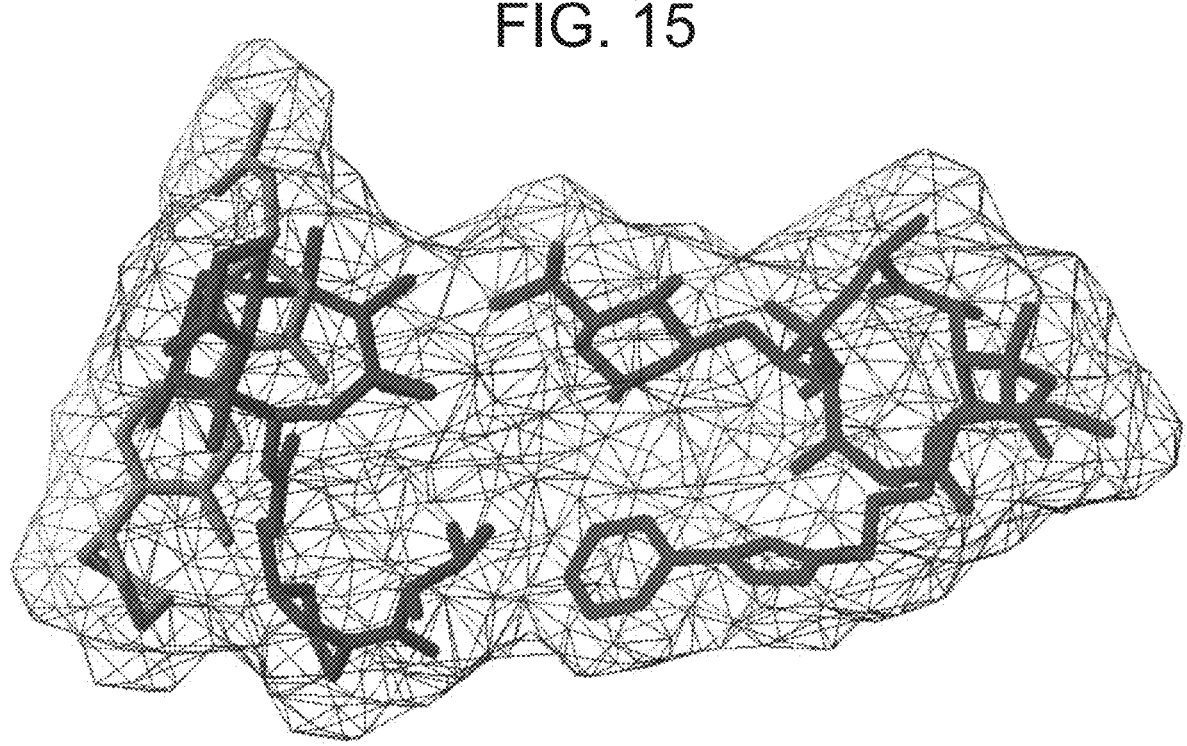
Figure 16:
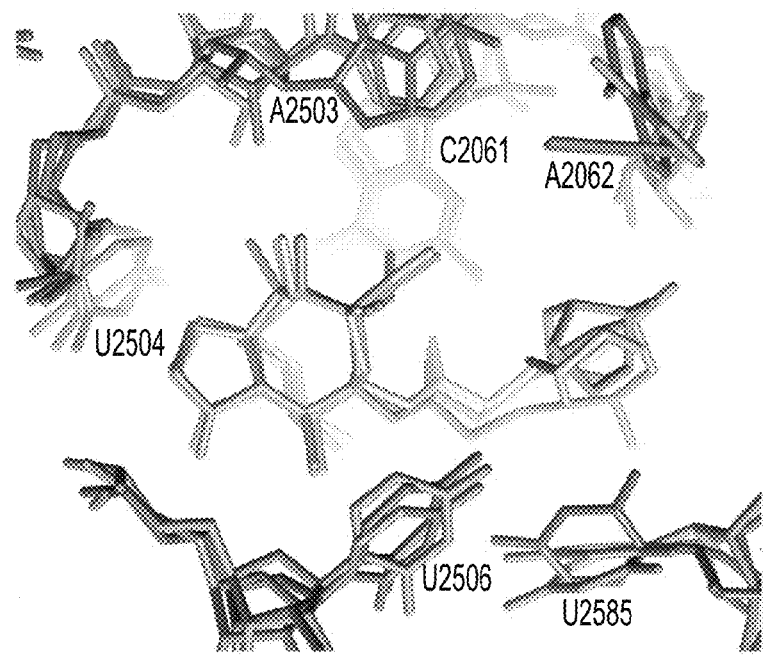
Figure 17:
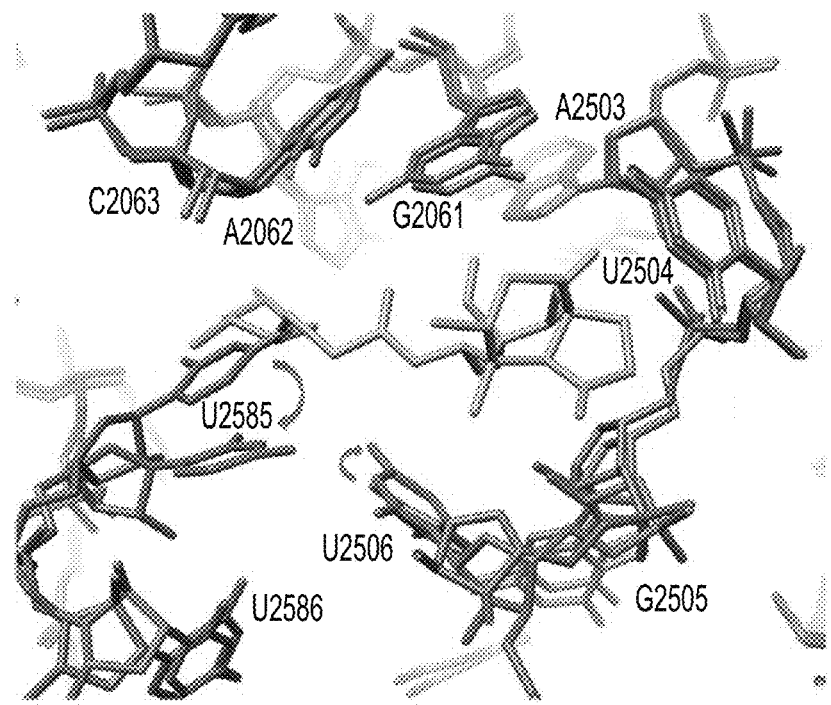
Figure 18:
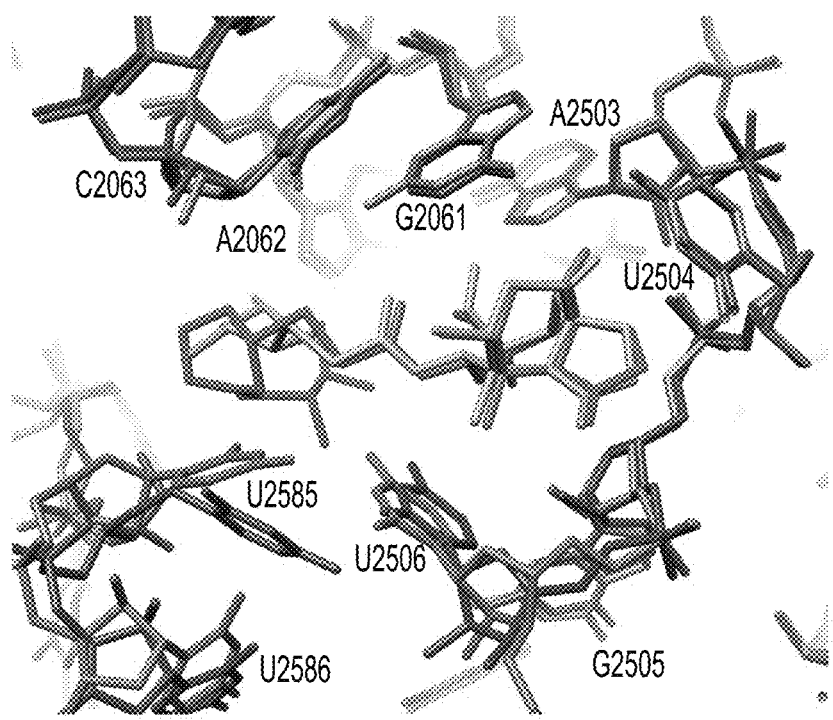
Figure 19:
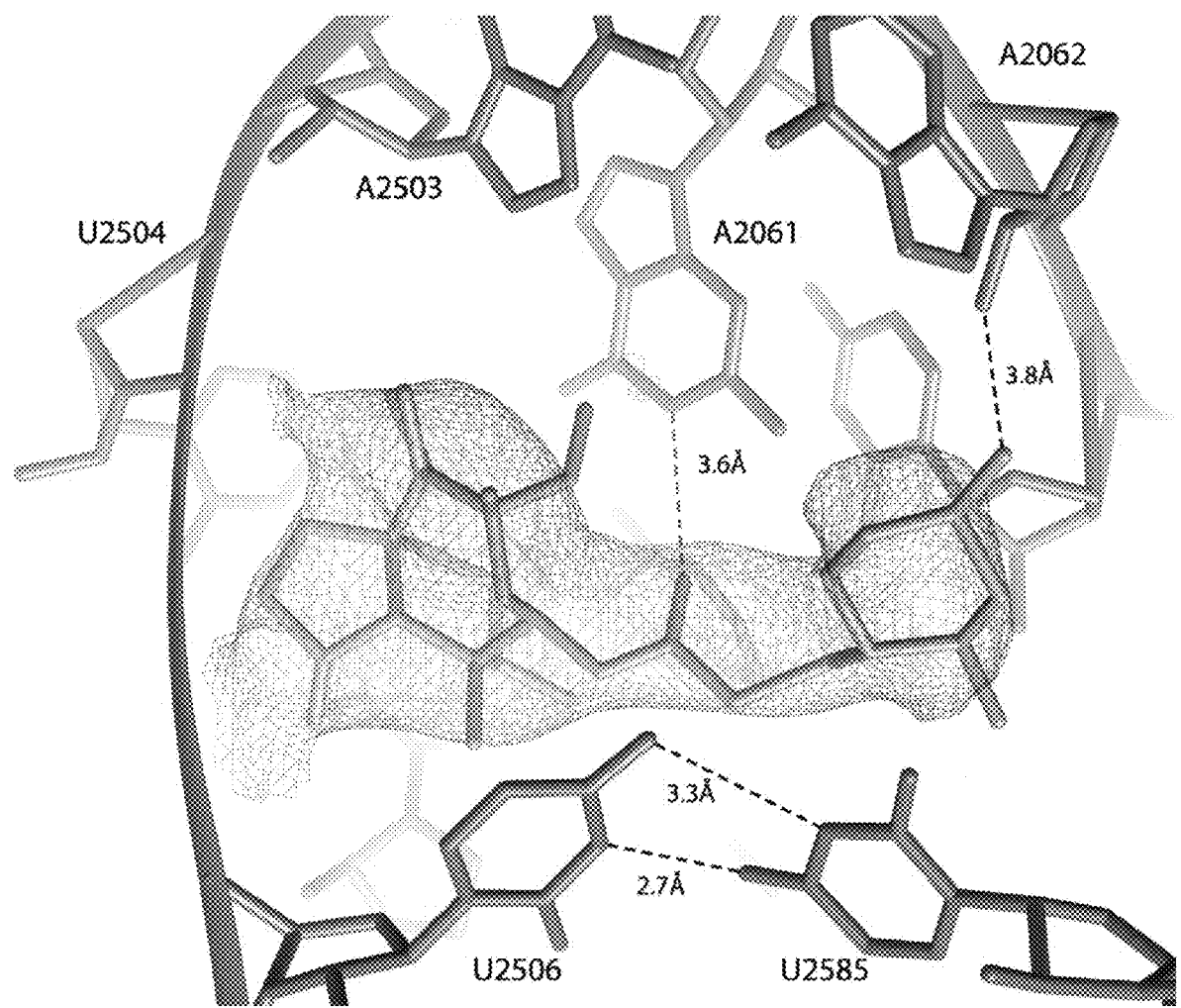
Figure 20A:
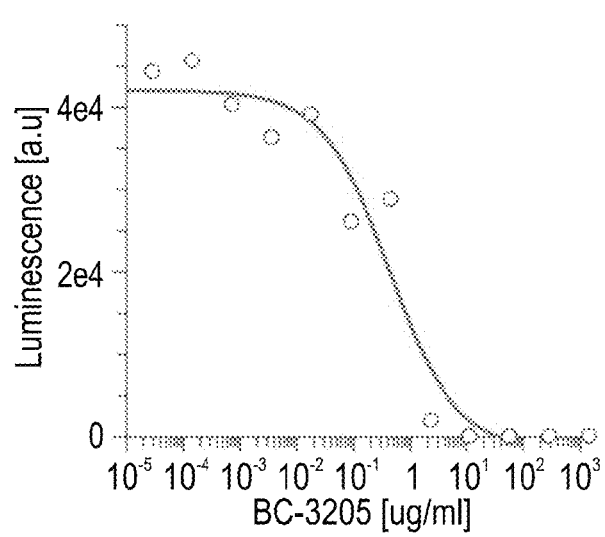
Figure 20B:
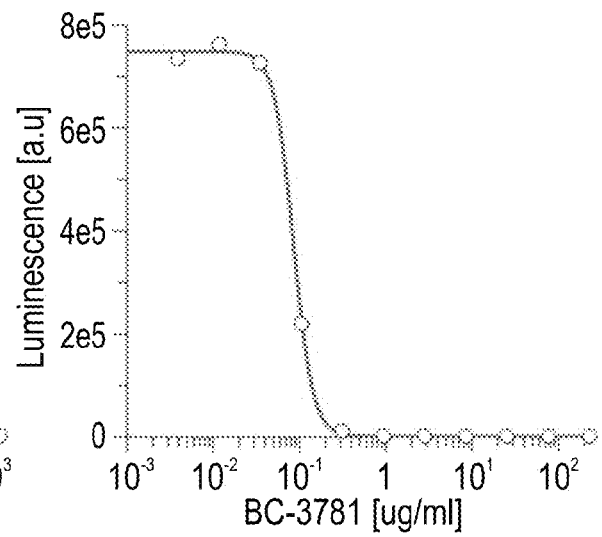
Figure 21:
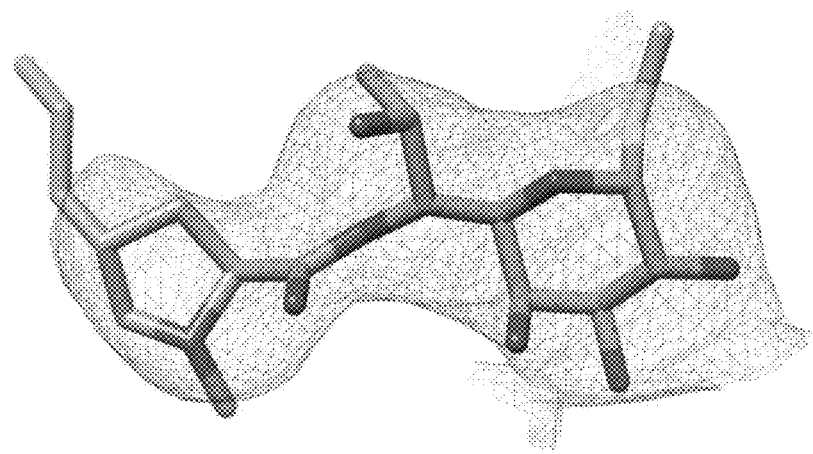
Figure 22:
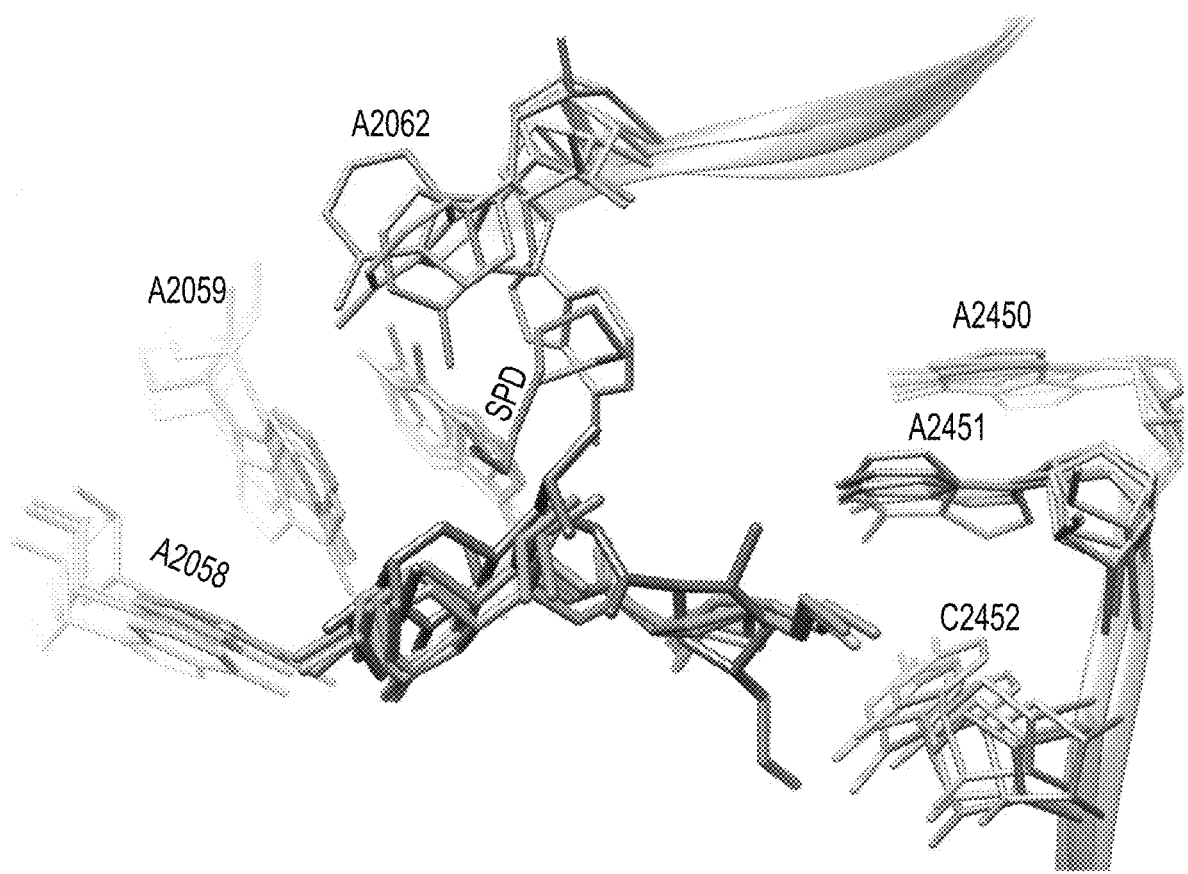
Figure 23A:
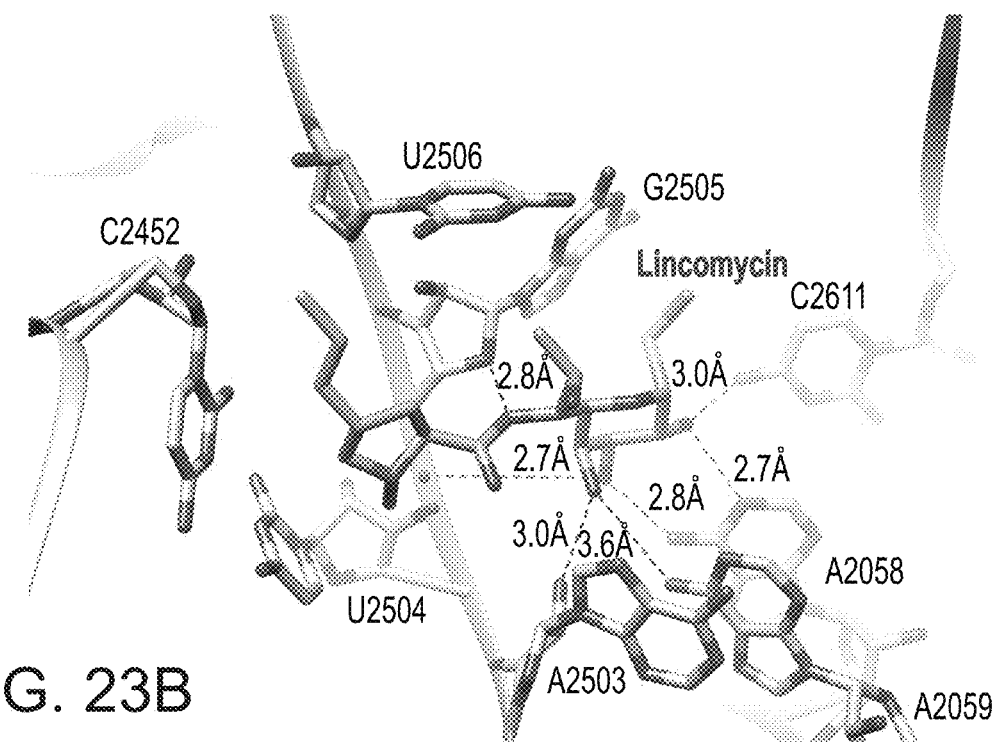
Figure 23B:
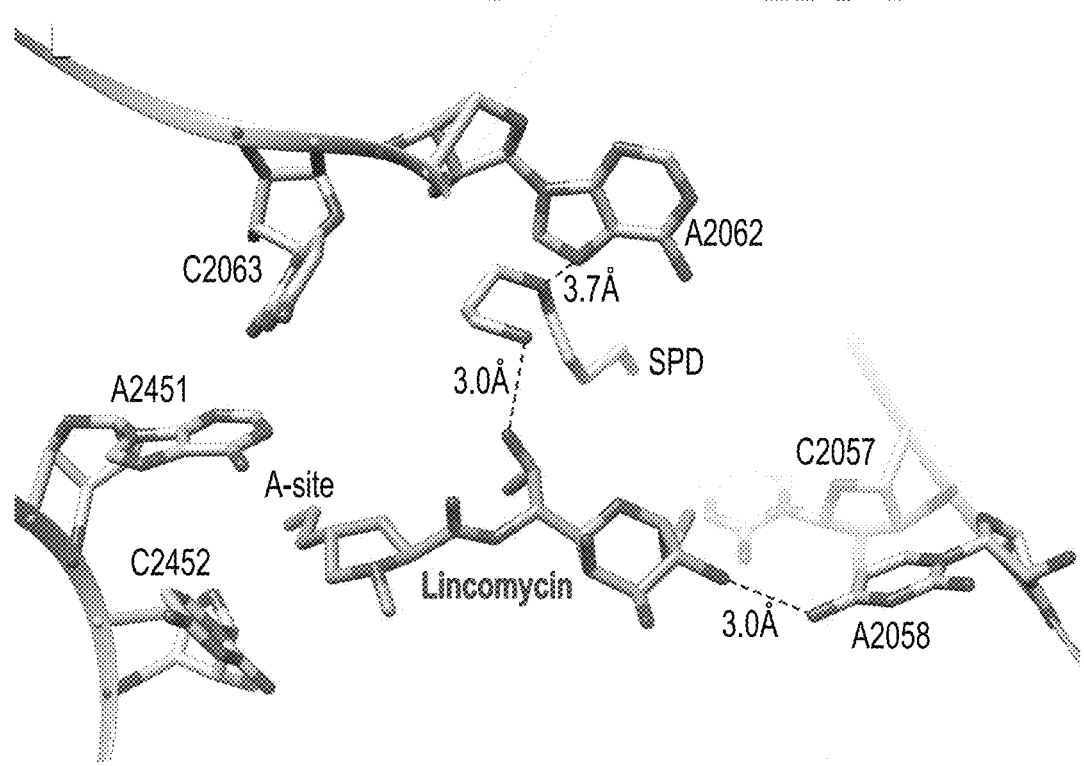
Figure 24:
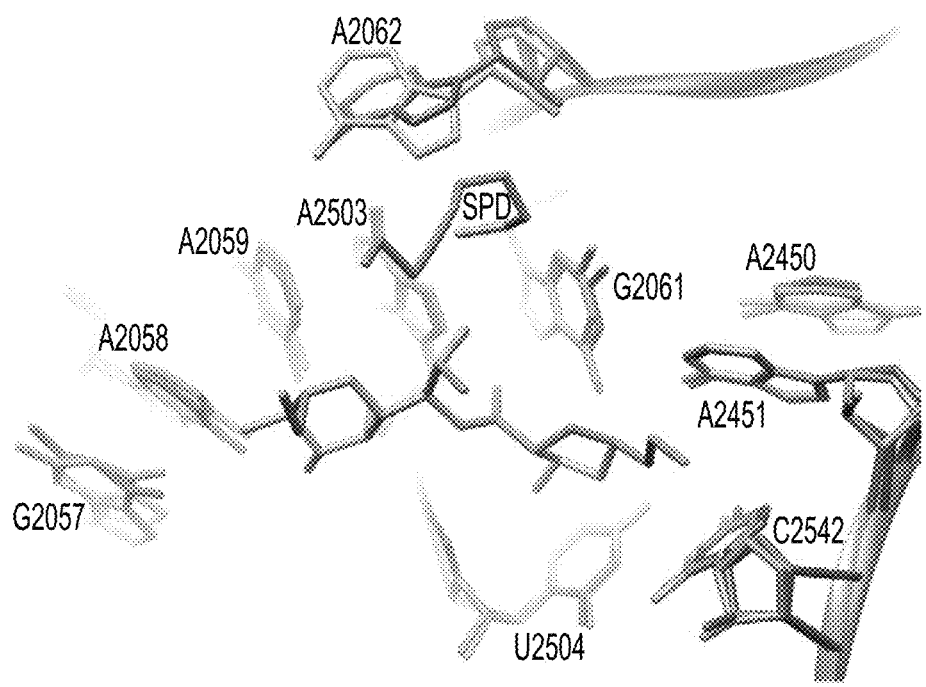

FIG. 1 presents a graphic illustration of the crystal structure of the large ribosomal subunit of SA (SA50S), according to some embodiments of the present invention, wherein the rRNA is colored in grey, the rProteins are colored in various colors, the PTC is marked by a red star and the approximate path of the internal exit tunnel is marked by a band colored in dark blue;

FIGS. 2A-2F present the weighted $2F_o$-$F_c$ electron density maps of linezolid (FIG. 2A), telithromycin (FIG. 2B) and BC-3205 (FIG. 2C), contoured at 1.0 σ, and the weighted $F_o$-$F_c$ electron density maps of linezolid (FIG. 2D), telithromycin (FIG. 2E) and BC-3205 (FIG. 2F), contoured at 3.0 σ;

FIGS. 3A-3B present a graphic illustration of the structure of SA50S, showing relative locations of the rRNA regions with fold variability on the SA50S subunit, wherein SA50S 23S rRNA is shown in teal, and the variable regions are shown in orange, whereby (FIG. 3A) and (FIG. 3B) are rotated 90° with respect to each other;

FIGS. 4A-4H present graphic illustrations of superimposed structure models of S. aureus (colored in teal), D. radiodurans (colored in grey), E. coli (colored in purple) and T. thermophilus (colored in orange), showing the structural variability in the rRNA backbone, wherein in FIG. 4A the h25 region is emphasized, in FIG. 4B the h9 region is emphasized, in FIG. 4C the h63 region is emphasized, in FIG. 4D the h10 region is emphasized, in FIG. 4E the h79 region is emphasized, in FIG. 4F the h15 and h16 regions are emphasized, in FIG. 4G the h68 region is emphasized, and in FIG. 4H the h28 region is emphasized;

FIGS. 5A-5B present graphic illustrations of the flexible nucleotides at the PTC and at the exit tunnel (FIG. 5A), showing U2506, U2585, A2062, A2602 and U2491, where the P-site tRNA (shown as a green surface) and the A-site tRNA (shown as a blue surface) would bind, whereas S. aureus 23S RNA backbone and nucleotides are colored in teal, and D. radiodurans, T. thermophilus and E. coli nucleotides are shown in grey, orange and purple, respectively, and further showing the flexible nucleotides towards the tunnel opening (FIG. 5B), wherein A90, A91 and A508 are located in the ribosomal exit tunnel, detected with different conformations in all four structures, and a possible path of the backbone of a modeled nascent poly-alanine chain is represented by a thick yellow string;

FIGS. 6A-6D present graphic illustrations of the surface of the SA50S indicating the locations of the globular regions of the rProteins, whereas rRNA is shown in grey and the various rProteins are shown in different colors, showing a view from the SA50S intersubunit surface (FIG. 6A), a view from the SA50S outer surface (FIG. 6B), and views of a +90 degrees and −90 degrees vertical rotation of the intersubunit surface (FIG. 6C and FIG. 6D, respectively);

FIGS. 7A-7B present graphic illustrations of the subunit interface, showing some of the structural differences in the rProteins found between SA50S, T70S, E70S and D50S, while focusing on L5 (FIG. 7A) and L16 (FIG. 7B);

FIGS. 8A-8B present graphic illustrations emphasizing the structural differences between SA50S, T70S, E70S and D50S in the rProteins that interact with substrates, while focusing on L28 (FIG. 8A) and L27 (FIG. 8B);

FIGS. 9A-9G present graphic illustrations emphasizing the structural differences between SA50S, T70S, E70S and D50S in the rProteins at the rims of the erythromycin binding site (FIG. 9A), the exit tunnel opening focusing on L23, L24, and L29 (FIG. 9B), L24 in all 4 structures (FIG. 9C), the central protuberance (FIG. 9D); the L25, G11-L26, I49-T69, F79-186 loops, and the L16 C-terminal (FIG. 9E), the L25 and L16 C-terminal (FIG. 9F), and the L27 R79-K85 loop and C-terminal fold (FIG. 9G), whereas the possible path of the backbone of a modeled nascent protein chain is indicated in lime/yellow in some of the illustrations;

FIGS. 10A-10H present graphic illustrations emphasizing the structural differences between S. aureus (colored in teal), D. radiodurans (colored in grey), T. thermophilus (colored in orange) and E. coli (colored in purple) in some rProteins at the subunit surface, focusing on the L3 A57-L67 loop (FIG. 10A), the L17 T65-A81 loop (FIG. 10B), the V6-117 surface loop of n L4 and N-terminal of L15 (FIG. 10C), the C and N-terminals of L4 (FIGS. 10D-E), the L15 loops I69-T89 and T89-V97 (FIG. 10F), the L15 N-terminal (FIG. 10G), and the L28 globular domain (FIG. 10H);

FIGS. 11A-11B present graphic illustrations emphasizing the structural differences in the N-terminal of protein L32 that resides in the second shell around the erythromycin binding pocket, as seen in SA50S and E70S (FIG. 11A) and in T70S and D50S (FIG. 11B);

FIGS. 12A-12F present graphic illustrations of SA50S in complex with linezolid, referred to herein as SA50Slin (FIG. 12A and FIG. 12B), SA50S in complex with telithromycin, referred to herein as SA50Steli (FIG. 12C and FIG. 12D) and SA50S in complex with BC-3205, referred to herein as SA50S-BC3205 (FIG. 12E and FIG. 12F);

FIGS. 13A-13F present graphic illustrations of structures of native SA50S rRNA and rProteins (colored in teal), D50S (colored in grey), E70S (colored in purple) and T70S (colored in orange) superimposed for comparative analysis and study of the resistance and cross resistance mechanisms in SA, showing rRNA nucleotides of SA in regions where they can be well aligned with the corresponding nucleotides in all other structures used for the comparisons, focusing on L11 (FIG. 13A), L3 (FIG. 13B), the rRNA binding pocket (FIGS. 13C-D), and L4 (FIGS. 13E-F);

FIGS. 14A-14C present graphic illustrations of regions in the superimposed structures of S. cerevisiae 60S (PDB ID: 3U5D) (colored in yellow), T. thermophilia 60S (PDB ID: 4A18) (colored in red) and SA50S (colored in teal), showing the sequence and structural variability among eukaryotes and prokaryotes rRNA antibiotics binding pockets and vicinity when erythromycin (FIG. 14A), telithromycin (FIG. 14B) and tiamulin (FIG. 14C) are bound;

FIG. 15 presents an illustration of linezolid (green stick model), BC-3205 (blue stick model) and telithromycin (red stick model), as these three ligands are positioned in the crystal structure of the corresponding complex with SA50S, wherein each complex structures is superimposed on the native SA50S crystal structure, and further presents the molecular surface of the combined ligand structures illustrated as a wire mesh encasing the three ligands, wherein the coloring of mesh corresponds to the color of the ligand which contributes to the molecular surface at the corresponding region thereof;

FIG. 16 presents a graphic illustration of an overlay of lefamulin in the pleouromutilin binding site, as elucidated from the complex structures SA50Slef (orange), D50S-retapamulin (cyan; PDB ID: 2OGO) and D50S-SB280080 (lemon; PDB ID: 2OGN);

FIG. 17 presents a graphic illustration of an overlay of the PTC in native SA50S (teal) and in SA50Slef complex (orange), revealing the movements of nucleotide U2585 in the bound vs. native structure;

FIG. 18 presents a graphic illustration of an overlay of the PTC in complex structure SA50SBC-3205 (magenta) and in complex structure SA50Slef (orange);

FIG. 19 presents a graphic illustration of the ribosomal binding pocket of lefamulin, as seen in the complex crystal structure SA50Slef, showing that the ligand is held within the PTC by a net of hydrogen bonds with the 23S rRNA, wherein the U-U interactions between U2585 and U2506 stabilizes the lefamulin binding pocket (the electron density of lefamulin is weighted $2F_o-F_c$ contoured at 1.0 σ);

FIGS. 20A-20B present the results of in vitro transcription-translation cell-free inhibition assays of bacterial protein synthesis, wherein the inhibitory effect on protein expression in *S. aureus* system of BC-3205 is presented in FIG. 20A and of lefamulin is presented in FIG. 20B. The activity of the reporter protein (luciferase) in the presence of various concentrations of BC-3205 and lefamulin is shown as arbitrary unit of luminescence [a.u.]. The $IC_{50}$ values calculated by the plotted data showed better inhibition of lefamulin than BC-3205 on protein synthesis;

FIG. 21 presents a graphic illustration of the electron density map (weighted 2Fo-Fc contoured at 1.0 σ) attributed to a molecule of lincomycin as seen in the crystal structure of the antibiotic agent in complex with SA50S;

FIG. 22 presents a graphic illustration showing a structural superposition of the two lincosamides in their common binding site, wherein the structure of the bound lincomycin is derived from SA50Slinc (presented in pink) and structure of the bound clindamycin is derived independently from PDB ID: 1JZX disclosing *D. radiodurans*-lincomycin complex (D50S-CLY, presented in grey), PDB ID: 1YJN disclosing *H. marismortui*-lincomycin complex (H50S-CLY, presented in sky-blue), and PDB ID: 3OFZ disclosing *E. coli*-lincomycin complex (E70-CLY, presented in green);

FIGS. 23A-23B present a graphical illustration of the binding pocket of lincomycin in SA50S, wherein FIG. 23A shows lincomycin (presented in pink) interacts with the PTC A-site by numerous hydrogen bonds (dashed line) with the 23S rRNA (presented in grey), and FIG. 23B is a 90 degrees horizontal rotated view of FIG. 23A; and FIG. 24 present a graphical illustration of a structural superposition of the PTC in native SA50S (presented in teal) and in SA50S-lincomycin complex (presented in pink), showing a difference in the position of nucleotide A2062 in the SA50Slinc towards the spermidine (SPD) compared to the native structure.

DESCRIPTION OF SPECIFIC EMBODIMENTS OF THE INVENTION

The present invention, in some embodiments thereof, relates to a structure-based drug design and, more particularly, but not exclusively, to methods for designing species-specific antimicrobial agents based on crystal structures of pathogenic ribosomal subunits.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Despite the high sequence similarity of eubacterial rRNA, species specificity has been observed under clinically relevant conditions in genuine pathogen, particularly in the modes of acquiring antibiotic resistance. While conceiving the present invention, it has been recognized by the present inventors that designing target specific drugs, and in particular drugs that target exogenous pathogenic microorganism in a host which is symbiotic with other non-pathogenic microorganism, would require identifying and elucidating notable differences of strategic vulnerabilities between pathogenic and non-pathogenic microorganisms at the molecular level. Considering that even small structural differences can affect drug binding modes, it has been recognized that designing such highly specific antibacterial agents which act on the protein synthesis mechanism of the pathogenic bacterium can be afforded by acquiring experimental crystal structures of at least some subunits of the pathogen's ribosome.

Bacteria are grouped into two categories, Gram positive bacteria and Gram negative bacteria, based on their cell wall structure and various characteristics stemming therefrom. Among the various differences, those that involve interaction with a host organism and those that involve interaction with antibiotics bear a particular interest from pharmacologic and therapeutic aspects.

Generally, Gram positive bacteria exhibit a smooth 20-30 nm thick cell wall and no outer membrane; while Gram negative bacteria exhibit a wavy 8-12 nm thin cell wall and an outer membrane. In general terms of human host interactions, Gram positive bacteria is more aerobic and found typically on the skin and in the respiratory tract, including mouth, throat and lungs, while Gram negative bacteria is more anaerobic and is typically found in the GI tract.

In terms of virulence and pathogenicity, both types of bacteria may be involved in infectious conditions and diseases, with some distinguishing characteristics which are not related to the infected site, organ or sub-system. For example, Gram positive bacteria produce primarily exotoxins that the bacterial cell secretes during its life cycle, while Gram negative bacteria produce primarily endotoxins that affect the host upon bacterial cell breakdown.

From the pharmaceutical point of view, the above differences are expressed in different sensitivity of each of the bacterial types to different antibiotics under different conditions, including different mechanisms of antibiotic activity and different mechanism for developing resistance to antibiotics. For example, cephalosporins of the "first generation", such as cefadroxil, cefazolin, cefalotin, cefalothin and cefalexin, glycopeptides such as teicoplanin, vancomycin, telavancin, dalbavancin and oritavancin, and lipopeptides such as daptomycin, are more potent against Gram positive bacteria including MRSA; while cephalosporins of the "second generation" such as cefaclor, cefamandole, cefoxitin, cefprozil and cefuroxime, cephalosporins of the "third generation" such as cefixime cefdinir, cefditoren, cefoperazone, cefotaxime, cefpodoxime, ceftazidime, ceftibuten, ceftizoxime and ceftriaxone, aminoglycosides such as amikacin, gentamicin, kanamycin, neomycin, netilmicin, tobramycin, paromomycin, streptomycin and spectinomycin, polypeptides such as bacitracin, colistin and polymyxin B, and monobactams such as aztreonam are more potent towards Gram positive bacteria.

Out of the pathogenic Gram positive bacteria family, the Gram positive cocci constitute a sub-family of bacteria which is typically pathogenic in humans. It is estimated that members of this family are the cause of at least a third of all the bacterial infections observed in humans. A sub-family of Gram positive cocci includes Staphylococci bacteria, which are among the most common bacteria causing human disease; out of which *Staphylococcus aureus* (SA) is one of the most common pathogenic bacterium. Pathogenic staphylococci are ubiquitous, and are carried, usually transiently, in the anterior nares of about 30% of healthy adults and on the skin of about 20%. Rates are higher in hospital patients and personnel. Staphylococci species such as *S. epidermidis* are increasingly associated with hospital-acquired infections; *S. saprophyticus* causes urinary infections. *S. lugdunensis* causes invasive disease with virulence similar to that of *S. aureus*.

Most staphylococcal diseases are caused by direct tissue invasion, and include skin infections, pneumonia, endocarditis, osteomyelitis and septic arthritis. *Staphylococcus aureus* is considered as one of the most pathogenic bacteria in humans, causing skin infections, pneumonia, endocarditis and osteomyelitis. Infections by this pathogen commonly lead to abscess formation. Some strains elaborate toxins that cause gastroenteritis, scalded skin syndrome, and toxic shock syndrome. Diagnosis is by Gram stain and culture. Treatment is usually with penicillinase-resistant β-lactams, but because antibiotic resistance is common, vancomycin or other newer antibiotics may be required. Some strains are partially or totally resistant to all but the newest antibiotics, which include linezolid, quinupristin/dalfopristin, daptomycin, telavancin, dalbavancin, tigecycline, and ceftaroline.

The present inventors have uncovered the conditions required to produce, isolate and crystallize the large ribosomal subunit (50S) from a life-threatening pathogenic bacterium, *Staphylococcus aureus* (SA), and thereby have successfully crystallized this bacterial ribosomal unit. The large ribosomal subunit (50S) of *Staphylococcus aureus* (SA) is the first bacterial large ribosomal subunit of a real pathogenic bacterium which has been crystallized to date.

The present inventors have further determined the crystal structure of the large ribosomal subunit (50S) of *Staphylococcus aureus* (SA), herein throughout referred to interchangeably as the SA50S subunit, and further determined the crystal structures of complexes thereof with several antibacterial agents. The obtained crystal structures were compared amongst themselves and with structures of ribosomal particles from other species, and the insights gained from these comparative structural analyses have been used to provide unique knowledge-based tools for understanding species specificity, for improving the clinical performance of known antibiotics and for designing novel antibiotics which would interact with known and newly-identified peripheral binding sites on the target's ribosome. Furthermore, by studying the intricate interaction between an antibacterial agent and its molecular target, gaining insights on the molecular structural factors that govern immergence of resistance in a pathogen was enabled.

The SA50S subunit is composed of 2 rRNA chains and 26 rProteins chains. Table 1 below provides their types, names, chain ID and SEQ ID NOs. The actual sequences of these molecules are listed in the Sequence Listing that accompanies this application.

TABLE 1

| Type | Name | Chain ID | SEQ ID NO.: |
|---|---|---|---|
| rRNA | 23S | X | 1 |
| rRNA | 5S | Y | 2 |
| rProtein | L2 | A | 3 |
| rProtein | L3 | B | 4 |
| rProtein | L4 | C | 5 |
| rProtein | L5 | D | 6 |
| rProtein | L6 | E | 7 |
| rProtein | L13 | G | 8 |
| rProtein | L14 | H | 9 |
| rProtein | L15 | I | 10 |
| rProtein | L16 | J | 11 |
| rProtein | L17 | K | 12 |
| rProtein | L18 | L | 13 |
| rProtein | L19 | M | 14 |
| rProtein | L20 | N | 15 |
| rProtein | L21 | O | 16 |
| rProtein | L22 | P | 17 |
| rProtein | L23 | Q | 18 |
| rProtein | L24 | R | 19 |
| rProtein | L25 | S | 20 |
| rProtein | L27 | T | 21 |
| rProtein | L28 | U | 22 |
| rProtein | L29 | V | 23 |
| rProtein | L30 | W | 24 |
| rProtein | L32 | Z | 25 |
| rProtein | L34 | 2 | 26 |
| rProtein | L35 | 3 | 27 |
| rProtein | L36 | 4 | 28 |

Provided herein is the first crystal structure of a ribosomal particle from a genuine pathogen, alongside the crystal structures of its complexes with linezolid, telithromycin and lincomycin, and two exemplary pleuromutilin, BC-3205 and lefamulin.

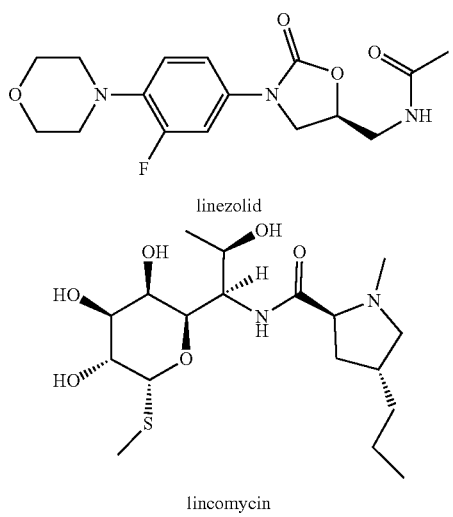

linezolid lincomycin

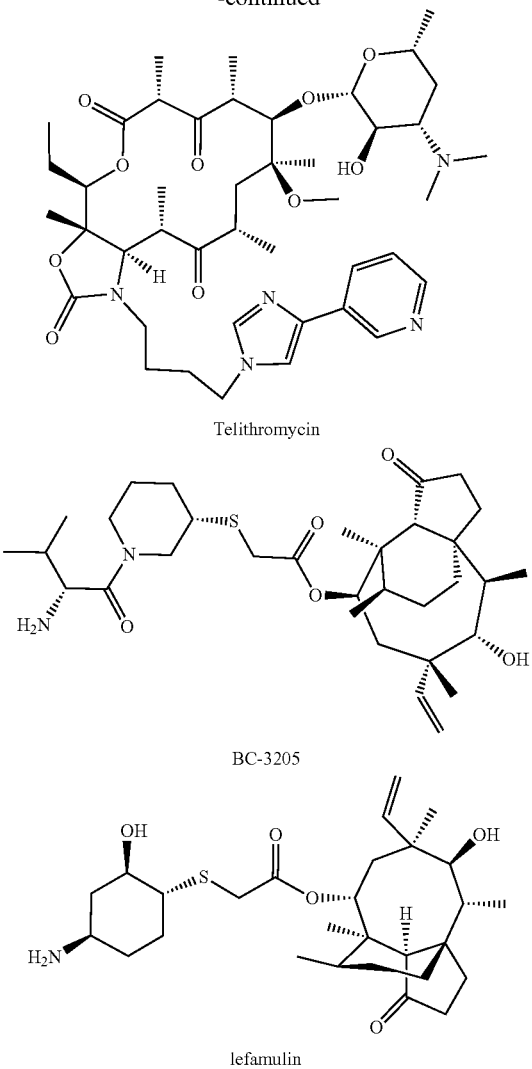

Telithromycin

BC-3205 lefamulin

As used herein, the terms "antibiotic(s)", "AB", "antibiotic drug(s)" and "antibacterial agent(s)" are used interchangeably to refer to a naturally occurring, synthetic or semi-synthetic substance which is directed or effective against bacteria.

Further provided herein are some of the specific traits and principles which govern the selectivity and resistance of this genuine pathogen, elucidated by analyzing these structures and comparing them with the known structures of the corresponding non-pathogenic eubacteria and their complexes with linezolid, telithromycin and pleuromutilins. Further provided herein are comparisons between specific ribosomal nucleotides and proteins that belong to the antibiotic binding pockets in the pathogen's ribosomal subunit and its eukaryotic equivalent. The studies presented herein have been utilized in the structural definition of components within the ribosome that can be selectivity utilized for the design of novel and/or improved antibacterial agents to target the SA's ribosome.

While further reducing the present invention to practice, the inventors have used sequence and structure alignments of *S. aureus* large ribosomal subunit rRNA with its counterparts from other eubacteria, which indicated high degree of conservation. Nonetheless, structural characterization of this ribosomal particle and of its complexes with two clinically used antibiotics and one potential new antibiotic, revealed significant differences which have been contemplated as knowledge for the design of novel and improved antibacterial agents. Analysis of the structures of the unbound and the drug-bound ribosomes versus ribosomes from non-pathogenic eubacteria, revealed specific structural motifs that may indicate possible features involved in species-specific acquirement of resistance and drug binding. These newly obtained insights provide unique structural tools for the definition of the structural features acquiring species specificity, including the distinction between pathogenic bacteria and the useful bacterial species within the human body.

The present inventors have also identified structural motifs, within the particle's core and on its periphery, which do not belong to the known antibiotic binding sites, but may be candidates for the design of selective drugs against SA. A non-limiting example is the void in the vicinity of erythromycin binding site (see, FIGS. 11A-B) that may be exploited for improving existing macrolide antibacterial agents and novel binding sites that may be used for the design of new antibacterial agents, thus enriching the pool of potential antibacterial agents with minimized and/or controlled resistance to pathogenic bacteria. In this respect, the superiority of the new lead compound, BC-3205, over known pleuromutilins, that is indicated by its strong binding to SA ribosome and low MICs, was clearly corroborated by the structural elements of its binding mode.

A Composition-of-Matter:

A ribosome, as this term is used herein and in the field of biology and other life sciences, is a complex sub-cellular entity which is the main part of natural protein biosynthesis. The term "ribosomal subunit", as used herein, describes one of the two subunits of a ribosome—the small subunit which generally binds the mRNA, and the large subunit which generally binds the tRNA. Each of the small and large ribosomal subunits is made from a plurality of RNA molecules, referred to as rRNA, and proteins, referred to as rProteins. The Svedberg unit is typically used to describe the various ribosomal subunits, whereas the unit is used to denote the rate of sedimentation of the subunit during centrifugation rather than its size. For example, prokaryote cells have 70S ribosomes, each consisting of a small (30S) and a large (50S) subunit, and eukaryotes have 80S ribosomes, each consisting of a small (40S) and large (60S) subunit.

According to an aspect of some embodiments of the present invention, there is provided a composition-of-matter which comprises a crystallized form of at least one ribosomal subunit of a pathogenic bacterium.

According to some embodiments of this aspect of the present invention, the composition-of-matter provided herein includes a crystallized form of a large ribosomal subunit of a pathogenic bacterium which is other than *Escherichia coli*.

According to some embodiments of this aspect of the present invention, the pathogenic bacterium is a pathogenic Gram positive bacterium, and/or a pathogenic bacterium exhibiting a degree of 23S rRNA sequence identity of at least 80% compared to the 23S rRNA of *Staphylococcus aureus*.

As used herein, the term "pathogen", including all its inflections, such as "pathogenic", describes an infectious microorganism, such as a bacterium, a fungus or protozoan, which causes disease in its host. According to some embodiments, the pathogen is an infectious bacterium, and more specifically a bacterium that forms an adverse parasitic association with one or more other organisms, referred to herein as a "host". According to some embodiments, the term "pathogenic bacterium" refers to a member of the domain of bacteria, which causes a disease or disorder in a mammalian host, such as a human.

In some embodiments of the present invention, the pathogenic bacterium belongs to the Kingdom of Eubacteria; in some of the embodiments, the pathogenic bacterium belongs to the Phylum of Firmicutes; in some of the embodiments, the pathogenic bacterium belongs to the Class of Bacilli; in some of the embodiments, the pathogenic bacterium belongs to the Order of Bacillales; in some of the embodiments, the pathogenic bacterium belongs to the Family of Staphylococcaceae; in some of the embodiments, the pathogenic bacterium belongs to the Genus of *Staphylococcus*; and in some of the embodiments, the pathogenic bacterium belongs to the Species of *Staphylococcus aureus* (*S. aureus*, referred to herein as "SA").

According to some embodiments, the composition-of-matter described herein includes a crystallized form of a 50S subunit of a pathogenic Gram positive bacterium.

According to some of any of the embodiments of the present invention, the pathogenic bacterium is a Gram positive bacterium. Exemplary of pathogenic Gram positive bacteria genii include *Staphylococcus, Streptococcus, Clostridium, Corynebacterium, Enterococcus* and *Listeria*.

In some of any of the embodiments of the present invention, the Gram positive bacterium is a Gram positive cocci bacterium; in some of the embodiments, the Gram positive cocci bacterium is a *Staphylococcus* bacterium; and in some of the embodiments, *Staphylococcus* bacterium is *Staphylococcus aureus*. In some of the embodiments of the present invention, the composition-of-matter provided herein comprises the large ribosomal subunit of *Staphylococcus aureus* (referred to herein as "SA50S") in a crystallized form, or a crystal of SA50S.

As known in the art, antibacterial agents, also referred to herein and in the art as antibiotics, and in some cases also as antimicrobial agents, are used to treat hosts which have been infected with a pathogenic bacterium. Hence, it is noted herein that the pathogenicity of a pathogenic bacterium may also be associated with the capacity to develop a resistance to one or more antibacterial agents, namely that a population of pathogenic bacteria in a host, which is treated with an antibacterial agent, may survive the treatment by either acquiring the ability to survive an exposure to the antibacterial agent in the host, or elsewhere prior to the infection event. As known in the art, antibiotic resistance may develop in pathogenic bacteria by mutations in the bacterial genetic code, which are expressed, for example, in the rRNA and ribosomal proteins thereof.

According to some embodiments of the present invention, the ribosomal subunit forming a part of the composition-of-matter provided herein is of a pathogenic bacterium which is capable of developing a resistance to an antibacterial agent (also referred to herein as "antibiotic resistant pathogenic bacteria").

In some of any of the embodiments of the present invention, the antibiotic resistant pathogenic bacterium is an antibiotic resistant pathogenic Gram positive bacterium.

In some of any of the embodiments of the present invention, the antibiotic resistant pathogenic bacterium is an antibiotic resistant pathogenic bacterium exhibiting a degree of 23S rRNA sequence identity of at least 80% compared to rRNA of *Staphylococcus aureus*.

In some of any of the embodiments of the present invention, the antibiotic resistant pathogenic bacterium is an antibiotic resistant pathogenic bacterium exhibiting a degree of 23S rRNA sequence identity of less than 99.9% compared to rRNA of *Escherichia coli*.

Non-limiting examples of antibiotic resistant pathogenic Gram positive bacteria include *Streptococcus, Staphylococcus, Enterococcus, Clostridium, Mycobacterium, Corynebacterium, Coccobacillus* and *Bacillus*.

According to some embodiments of the present invention, the pathogenic Gram positive bacterium which is capable of developing a resistance to an antibacterial agent is *Staphylococcus aureus*, and more specifically the pathogenic bacterium is *Staphylococcus aureus* such as, but not limited to, a methicillin-resistant *Staphylococcus aureus* (MRSA), an oxacillin-resistant *Staphylococcus aureus* (ORSA), a vancomycin-resistant *Staphylococcus aureus* (VRSA) and a vancomycin intermediate *Staphylococcus aureus* (VISA).

According to some embodiments, the composition-of-matter provided herein comprises a crystallized form of a 50S subunit of an antibiotic resistant pathogenic bacterium exhibiting degree of 23S rRNA sequence identity of at least 80% compared to the 23S rRNA of an antibiotic resistant *Staphylococcus aureus*.

Without limitation, it is noted that closely related species, in terms of bacterial phylogeny, are expected to exhibit high degree of ribosome structure similarity, while phylogenetic relations of bacteria is typically assessed by the degree of rRNA sequence identity. In other words, ribosomal structure similarity is expected to be high within a genus and within evolutionary closely related bacterial genii. Without being bound by any particular theory, it is assumed that the higher the overall rRNA sequence identity—the higher is the structural similarly of the compared large ribosomal subunits.

The 23S rRNA is about 3000 nucleotide long component (chain) forming a part of the large ribosomal subunit (50S) in bacteria. The ribosomal peptidyl transferase activity resides in domain V of this rRNA, and this domain is the most common binding site for antibiotics that inhibit translation (i.e., large subunit ligands). For example, a well-known member of this antibiotic class, chloramphenicol, acts by inhibiting peptide bond formation, with recent 3D-structural studies showing two different binding sites depending on the species of ribosome. Linezolid and quinupristin-dalfopristin also bind to the 23S rRNA, and cross-resistance has been demonstrated between these antibiotics.

Some phylogenetic analysis conventions in the field are based on comparing bacterial rRNA sequence of one or more ribosomal subunits, such as the 23S ribosomal RNA which forms a part of the large 50S subunit, another long and conserved ribosomal RNA chain, or the entire bacterial rRNA. Table 2 below presents some comparative data pertaining to some non-limiting examples of bacterial species, including the degree of rRNA identity with respect to that of *Staphylococcus aureus* 23S rRNA, denotation of X-ray structure availability in terms of the structure's resolution, the availability of complex structures with ribosomal ligands, Pathogenicity in mammals and the family affiliation.

TABLE 2

| Exemplary Species (23S accession number) | 23S rRNA % identity w/r/t S. aureus | Resolution of available structure | Availability of complex structure(s) with ligand | Pathogenicity in mammals | Gram staining/Family |
|---|---|---|---|---|---|
| Staphylococcus aureus (NC_007795) | 100 | 3.5 Å | YES | Pathogenic | + |
| Escherichia coli (J01695) | 76 | 3.46 Å | YES | Partly pathogenic | − |
| Thermus thermophilus (AP008226) | 81 | 3.5 Å | YES | Non-pathogenic | − |
| Deinococcus radiodurans (AE000513 AE001864-AE002092) | 74 | 2.91 Å | YES | Non-pathogenic | evolutionary Gram negative but stains as Gram positive |
| Streptococcus pneumoniae strain R6 (AE007317 AE008385-AE008568) | 85 | — | — | Pathogenic | + |
| Bacillus subtilis strain AG1839 (CP008698) | 90 | — | — | Pathogenic | + |
| Clostridium difficile (AM180355) | 81 | — | — | Pathogenic | + |
| Salmonella bongori strain NCTC 12419 (FR877557.1) | 75 | — | — | Pathogenic | − |

The term "degree of 23S rRNA sequence identity", as used herein, refers to the degree of identity of the 23S rRNA sequence between that of *Staphylococcus aureus* and that of various pathogenic bacteria contemplated within the scope of the present invention. The use of the phylogenetic relations based on the 23S rRNA also means that all species which can be compared phylogenetically based on the presence of a 23S ribosomal subunit, are contemplated as part of the scope of the invention according to the definition of the term "degree of 23S rRNA sequence identity".

Unless stated otherwise, the term "degree of 23S rRNA sequence identity" refers to the difference in 23S rRNA sequence identity between a 23S rRNA sequence of a species of interest and the corresponding 23S rRNA sequence of *Staphylococcus aureus*.

In one particular instance the term "degree of 23S rRNA sequence identity" is used to signify that a ribosomal subunit is not of a particular species, such as for example *Escherichia coli*, by stating that the degree of 23S rRNA sequence identity of a given species is less than 99.9% compared to the corresponding 23S rRNA sequence of, for example, *Escherichia coli*.

According to some embodiments of the present invention, the degree of 23S rRNA sequence identity of various pathogenic bacteria contemplated within the scope of the present invention is higher than 77%, higher than 78%, higher than 79%, higher than 80%, higher than 81%, higher than 82%, higher than 83%, higher than 84%, higher than 85%, higher than 86%, higher than 87%, higher than 88%, higher than 89%, higher than 90%, higher than 91%, higher than 92%, higher than 93%, higher than 94%, higher than 95%, higher than 96%, higher than 97%, higher than 98%, or higher than 99%.

According to some embodiments of the present invention, any bacterial species which is considered "different than *Staphylococcus aureus*", or "other than *Staphylococcus aureus*", is identified by degree of 23S rRNA sequence identity which is less than 99.9%, less than 98%, less than 97%, less than 96%, less than 95%, less than 94%, less than 93%, less than 92%, less than 91%, less than 90%, less than 89%, less than 88%, less than 87%, less than 86%, less than 85%, less than 84%, less than 83%, less than 82%, less than 81%, or less than 80%, compared to the 23S rRNA sequence of SA. It is noted herein that the 3D structure of a ribosome or any subunit thereof may still be highly similar in two different species, and according to the non-limiting theory of sequence-structure-activity relationship, a prediction of their degree of structural similarity can be correlated to their degree of 23S rRNA sequence identity.

According to some embodiments of the present invention, the degree of 23S rRNA sequence identity of various pathogenic bacteria contemplated within the scope of the present invention is less than 99.9%, less than 99%, less than 98%, less than 97%, less than 96%, less than 95%, less than 94%, less than 93%, less than 92%, less than 91%, less than 90%, less than 89%, less than 88%, less than 87%, less than 86%, less than 85%, less than 84%, less than 83%, less than 82%, less than 81%, or less than 80%, compared to the 23S rRNA sequence of *Escherichia coli*.

As can be seen in Table 2, the degree of 23S rRNA sequence identity of, for example, *Escherichia coli* compared to *Staphylococcus aureus*, is 76%, namely lower than 77%.

Similarly, without limitation, it is noted that closely related species, in terms of bacterial phylogeny/genealogy, are expected to exhibit high degree of ribosomal protein sequence similarity/homology. In other words, ribosomal structure similarity is expected to be high within a genus and within evolutionary closely related bacterial genii. Without being bound by any particular theory, it is assumed that the higher the overall ribosomal protein sequence similarity/homology—the higher is the structural similarly/homology of the compared large ribosomal subunits.

According to some embodiments of the present invention, the degree of large subunit ribosomal protein sequence similarity/homology of various pathogenic bacteria contemplated within the scope of the present invention, for any one of the large subunit ribosomal proteins is higher than 70%, higher than 71%, higher than 72%, higher than 73%, higher than 74%, higher than 75%, higher than 76%, higher than 77%, higher than 78%, 79%, higher than 80%, higher than 81%, higher than 82%, higher than 83%, higher than 84%, higher than 85%, higher than 86%, higher than 87%, higher than 88%, higher than 89%, higher than 90%, higher than 91%, higher than 92%, higher than 93%, higher than 94%, higher than 95%, higher than 96%, higher than 97%, higher than 98%, or higher than 99%.

According to some embodiments, the composition-of-matter provided herein includes a crystallized form of a 50S subunit of *Staphylococcus aureus* (abbreviated as "SA50S").

For the sake of simplicity and brevity, the description below refers to the exemplary large ribosomal subunit of the pathogenic bacterium *Staphylococcus aureus* (SA50S), however, it is to be understood that large ribosomal subunits of other pathogenic bacteria, as defined herein, are also contemplated in some of any of the embodiments of the present invention, and that the use of the term "SA50S" herein should be regarded as an exemplary representative of a large ribosomal subunit of any pathogenic bacterium in any one of the embodiments and any combination thereof.

A composition-of-matter, according to any one of the embodiments described herein, comprises a three-dimensional physical crystal having a crystal lattice, and characterized by a crystallographic unit cell dimensions (cell constants) and symmetry, and an asymmetric unit. The unit cell is typically characterized by a crystallographic space group, as this term is known in the art. As these terms are known in the art, applying the symmetry operations on the asymmetric unit (following the operations of the space group) and applying translations of the unit cell along its edges by its unit cell dimensions, would reconstruct the macroscopic structure of the crystal lattice. In the context of the present embodiments, the crystal lattice comprises at least a plurality of ribosomal subunits; hence the composition-of-matter, according to some embodiments of the present invention, comprises at least a crystal of a ribosomal subunit; and in embodiments of the present invention, the composition-of-matter comprises at least a crystal of the large ribosomal subunit of a pathogenic bacterium, as described herein in any one of the respective embodiments of the present invention.

According to some of any of the embodiments described herein, the composition-of-matter may further comprise a medium or a solution which is referred to as "mother liquor" and includes a plurality of unbound molecular entities, such as, without limitation, solvent molecules, ions, solutes, buffers, protein solubility modifiers, freezing point modifiers and other additives.

According to some embodiments of the present invention, the crystal in the composition-of-matter may further include other molecular entities which are arranged in the same lattice as the ribosomal subunit, or be present in the media channels and passages between the crystallized ribosomal subunits and not necessarily arranged in a lattice, and which can be in chemical or physical association with the ribosomal subunit, or not.

When a ribosomal-bound molecular entity is exogenous to the ribosome, namely, it is not an rRNA strand and not a ribosomal protein chain, not a covalently-bound moiety resulting from port-translational cellular modifications and not an integral part of the ribosomal subunit, it is said that the ribosomal subunit and the molecular entity form a complex, and typically the molecular entity is referred to as "a ligand of the ribosomal subunit", and referred to herein as a "ligand" in short. A ribosomal ligand can form a complex with a ribosomal subunit and is expected to affect (i.e., enhance or inhibit) the activity of the ribosome.

Thus, in some of any of the embodiments of the present invention, the ribosomal subunit of the composition-of-matter may be associated with one or more ligands via chemical and/or physical interactions. By "associated with" it is meant that the ligand is in chemical or physical association with the ribosomal subunit in the composition-of-matter or a portion thereof; whereas "associated with" is meant to encompass terms such as "bound to", "complexed with" and the likes. When associated via chemical interactions, the association may be effected, for example, by one or more covalent bonds and/or by one or more non-covalent interactions. Examples of non-covalent interactions include hydrogen bonds, electrostatic interactions, donor-acceptor interactions, Van der Waals interactions, metal-coordination interactions and hydrophobic/aromatic interactions. These interactions lead to the chemical association of the ligand to the ribosomal subunit in the composition-of-matter. When associated via physical interactions, the association may be effected, for example, via absorption, entrapment, and the like.

In some of any of the embodiments of the present invention, a non-covalent or physical association of a ligand molecule with the ribosomal subunit is characterized by a dissociation constant of less than $10^{-5}$ M. In some of the embodiments, the dissociation constant is less than $10^{-6}$ M. In some of the embodiments, the dissociation constant is less than $10^{-7}$ M. In some of the embodiments, the dissociation constant is less than $10^{-8}$ M. In some of the embodiments, the dissociation constant is less than $10^{-9}$ M. In some of the embodiments, the dissociation constant is less than $10^{-10}$ M.

In some of any of the embodiments, a ribosomal subunit is associated with a ligand molecule via hydrophobic interactions, for example, a water-insoluble ligand molecule adheres to a hydrophobic region, e.g. a hydrophobic core or hydrophobic moieties, of a ribosomal subunit.

In some of the embodiments of the present invention, a ligand is covalently bound to the ribosomal subunit.

It is further assumed, without limitation, that the ligand, e.g. the antibacterial agent, binds to the ribosomal subunit in its crystallized form substantially in the same binding site on the ribosomal subunit and substantially by the same mode of binding (orientation, affinity and the likes) as in its solubilized (un-crystallized) form and substantially the same as it would bind to the ribosomal subunit in the living cell. Exemplary ligands include small molecules (less than 1 kD molecular weight), non-ribosomal peptides and polypeptides, carbohydrate, non-ribosomal nucleic acids and combination thereof. Ligands can play a role of co-factors, active-site inhibitors, activators and general ribosomal activity modulators.

In some of any of the respective embodiments of the present invention described herein, a ligand is an exogenous molecular entity that is capable of penetrating into the bacterial cell and forming a complex with the ribosome while the cell is still functional (live), thereby affecting the cell functions, primarily the cellular protein synthesis activity. In the context of some embodiments of the present invention, when the ligand inhibits the ribosomal activity, such as protein synthesis, it is referred to as an antibiotic or antibacterial agent.

The aforementioned complex can form before the crystal is formed, or be introduced into a pre-formed crystal of the ribosomal subunit, and form the complex while substantially preserving the crystal lattice and other properties of the pre-formed crystal such as unit cell dimensions and overall molecular arrangement and fold. It is noted that any molecular entity which is bound to the crystallized ribosomal subunit, forms a part of a crystallized complex, which is to say that it is found in the crystal lattice of the ribosomal subunit. It is noted that the unit cell dimensions may vary from crystal to crystal stemming from the same batch of crystals depending on environmental factors and the mother liquor condition and composition. Such variations in cell dimensions may be in the order of up to 1-4% in cell edge length. For example, when a unit cell dimension is about 300 Å it can vary from sample to sample (crystal to crystal) by about ±10 Å.

In some of any of the respective embodiments of the present invention described herein, the identification of a ligand with respect to its target of binding is made based on size differences, namely the larger entity is regarded as the target, and the smaller entity is the ligand. It is further noted that the term "ligand", as used herein, typically refers to molecular entities that bind in relatively small numbers (number of identical ligands per one major binding target molecular entity) to a specific site on the target and affect its biologic activity.

According to some of any of the embodiments of the present invention, the molar ratio of the ribosomal subunit in the lattice of the composition-of-matter to the bound ligand ranges from 1:1 to 1:2, or from 1:1 to 1:4, or from 1:1 to 1:6. According to some embodiments, solvent (e.g., water, ethanol, etc.) molecules, salt ions and other solutes which may bind to many sites in and/or on the ribosomal subunit, are not regarded as ligands since the ratio of ribosomal subunit to such molecular entities is typically larger than 1:6.

As demonstrated in the Examples section that follows, the present inventors have successfully prepared a sample of a substantially purified large ribosomal subunit obtained from the pathogenic bacterium *Staphylococcus aureus*, and further crystallized this large ribosomal subunit following a crystallization procedure, which is described in details hereinbelow.

According to some of any of the embodiments of the present invention, the crystallized large ribosomal subunit obtained from *Staphylococcus aureus* is characterized by the crystal space group P6522, and further characterized by a unit cell dimensions of a=279.756±10 Å, b=279.756±10 Å, c=872.725±10 Å, α=90, β=90 and γ=120.

It is noted that large ribosomal subunits obtained from other pathogenic bacteria, and also large ribosomal subunit obtained from *Staphylococcus aureus* and subjected to different crystallization procedures, may form crystals having a different crystal lattice, difference space group symmetry and different unit cell dimensions, and therefore the aforementioned crystal space group and unit cell dimensions should not be seen as limiting the scope of the invention, but rather as an embodiment thereof.

As discussed hereinabove, the crystallized entity in the composition-of-matter provided herein may be the ribosomal subunit per se or a complex of the ribosomal subunit and a ligand thereof.

According to some of any of the embodiments of the present invention, the composition-of-matter comprises a crystallized complex of a ribosomal subunit and an antibacterial agent. Without being bound to any particular theory, it is assumed that the mechanism by which the antibiotic agent exerts its antibiotic activity is by binding to the ribosomal subunit, thereby interfering with the biosynthesis of bacterial proteins.

According to some of any of the embodiments of the present invention, the composition-of-matter comprises a ligand which belongs to a family of ribosomal-active antibacterial agents, such as, but not limited to, the oxazolidinones family, the pleuromutilins family, and the macrolide family.

According to some embodiments of the present invention, exemplary antibacterial agents which form a crystallized complex in the composition-of-matter provided herein, include, without limitation, linezolid (an oxazolidinone), BC-3205 (a pleuromutilin) and telithromycin (a macrolide or a ketolide).

As presented in the Examples section that follows, the crystallized complex of the large ribosomal subunit of *Staphylococcus aureus* with linezolid is characterized by a crystal space group of P6522 and a unit cell dimensions of a=279.922±10 Å, b=279.922±10 Å, c=870.586±10 Å, α=90, β=90 and γ=120; the crystallized complex of the large ribosomal subunit of *Staphylococcus aureus* with BC-3205 is characterized by a crystal space group of P6522 and a unit cell dimensions of a=280.918±10 Å, b=280.918±10 Å, c=875.585±10 Å, α=90, β=90 and γ=120; and the crystallized complex of the large ribosomal subunit of *Staphylococcus aureus* with telithromycin is characterized by a crystal space group of P6522 and a unit cell dimensions of a=282.66±10 Å, b=282.66±10 Å, c=877.075±10 Å, a=90, β=90 and γ=120.

According to some of any of the embodiments of the present invention, any of the crystallized large ribosomal subunit of *Staphylococcus aureus* provided herein, either native (no ligand associated therewith) or complexed (associated) with an antibacterial agent, is characterized by a crystal lattice order which is sufficient to diffract collimated and focused electromagnetic radiation effectively so as to allow this diffracted radiation to be detected, measured and analyzed. Thus, any of the crystallized large ribosomal subunit of *Staphylococcus aureus* provided herein effectively diffracts X-rays for determination of atomic coordinates to a resolution of at least 10 Å, 8 Å, 6 Å, 5 Å, 4.5 Å, 4 Å, 3.5 Å or at least 3 Å.

Crystallization of a Large Ribosomal Subunit of a Pathogenic Bacterium:

According to an aspect of some embodiments of the present invention, the composition-of-matter described herein is afforded by crystallization of a purified sample of a ribosomal subunit, such as the large ribosomal subunit, of a pathogenic bacterium, and/or a pathogenic Gram positive bacterium, and/or a pathogenic bacterium exhibiting degree of 23S rRNA sequence identity of at least 80% compared to the 23S rRNA of *Staphylococcus aureus*. In some of any of the respective embodiments of the present invention, the composition-of-matter described herein is afforded by crystallization of a purified sample of the large ribosomal subunit of *Staphylococcus aureus*, also referred to herein as the SA50S ribosomal subunit.

According to some embodiments of the present invention, the sample is obtained by harvesting and purifying ribosomes from a lysate of a culture of the pathogenic bacterium under study. Purification and concentration of the ribosomal subunits is typically effected by centrifugation and/or chromatographic techniques and/or dialysis, all of which under conditions that preserve the structure of the ribosomal subunits as assessed, for example, by their ability to exert ribosomal activity.

The crystallization of the purified and concentrated ribosomal subunit is carried out by any method known in the art. An exemplary protein crystallization technique known as "hanging drop vapor diffusion crystallization" involves a downwards facing drop composed of a mixture of the protein/ribosome sample and a variety of reagents which is placed inside a vapor equilibration enclosure comprising a reservoir of reagents solution. Another exemplary protein crystallization technique is known as "sitting drop vapor diffusion crystallization" and involves an upwards facing drop composed of a mixture of the protein/ribosome sample and a variety of reagents which is placed inside a vapor equilibration enclosure comprising a reservoir of reagents solution. Another exemplary protein crystallization technique is known as "crystallization under oil" and involves a drop of sample combined with the crystallization reagent of choice which is pipetted under a layer of oil (also known as "microbatch crystallization"), whereas the oils can also be used as a barrier between the reservoir and the drop in traditional hanging or sitting drop crystallization experiments with vapor diffusion rate control. Another exemplary protein crystallization technique is known as "dialysis crystallization", which is not a vapor diffusion technique, and involves a sample separated from a precipitant solution by a semi-permeable membrane that allows small molecules such as ions, additives, buffers and salts to pass but prevent biological macromolecules from crossing the membrane.

According to some embodiments of the present invention, a sample of purified and concentrated SA50S ribosomal subunit is subjected to crystallization by a vapor diffusion technique, or vapor diffusion conditions, in which a solvent is gradually depleted by vaporization from a crystallization solution comprising the purified and concentrated SA50S sample and a precipitant (a substance that causes precipitation when added to a solution). During the vapor diffusion process the concentration of the precipitant in the crystallization solution gradually increases, thereby gradually lowering the solubility of the SA50S in the crystallization solution, such that the crystallization solution becomes saturated with respect to the SA50S. During the vapor diffusion process the SA50S gradually de-solubilizes (comes out of solution) to precipitate in an orderly fashion and deposit in a three-dimensional lattice to form a crystal thereof. Thus, according to some embodiments, the method of obtaining a crystal of SA50S is effected by subjecting an aqueous solution of SA50S to vapor diffusion conditions.

The phrase "vapor diffusion conditions", as used herein, refers to chemical, physical, mechanical and/or environmental conditions that favor crystal growth. In some of the embodiments of the present invention, slow, gradual, uninterrupted and controlled increase of the concentration of the entity to be crystallized allows the entity to form a lattice rather than amorphous sediment. In some of the embodiments, vapor diffusion conditions are such that the crystallization solution and the reservoir solution are kept in a relatively small (1-10 ml) container that can be essentially sealed-off the ambient environment.

In some of the embodiments of the present invention, the volume of the crystallization solution is significantly smaller than the volume of the reservoir solution (so as to, e.g., drive the equilibration process more efficiently).

In some of the embodiments of the present invention, the volume of the crystallization solution ranges from about 1 microliter (µl) to about 100 microliters (µl), and the volume of the reservoir solution ranges from about 0.1 microliter (ml) to about 10 milliliters (ml).

In some of the embodiments of the present invention, the crystallization solution is filtered prior to the crystallization process, so as, for example, to remove microscopic particles and/or minimize the formation of small crystals and/or minimize the formation of amorphous sediments.

In some of the embodiments of the present invention, the vapor diffusion conditions further include stabilized, constant and controlled temperature and humidity in a vibration-free environment.

In some of the embodiments of the present invention, the vapor diffusion conditions include sealing the crystallization solution in a compartment that also includes a reservoir of another solution, referred to herein as a "reservoir solution".

According to some embodiments of the present invention, the mechanical arrangement of the crystallization solution and the reservoir solution takes the format of a hanging drop arrangement or a sitting drop arrangement. In some of the embodiments, the vapor diffusion conditions take the format of a hanging drop in which a drop of the crystallization solution is applied substantially at the center and bottom of an air-tight lid (typically a transparent and circular cover slip) that closes a top opening of a container holding the reservoir solution. According to some embodiments, the volume of the crystallization solution (the volume of the hanging drop) is about 2-8 µl and the volume of the reservoir solution is about 0.8-1.2 ml.

According to some of any of the embodiments of the method described in this context of the present invention, the aqueous solution of SA50S which is subjected to vapor diffusion conditions is referred to herein as a "crystallization solution". In some of the embodiments, the SA50S in the crystallization solution is concentrated to a range of, for example, from 0.8 mg/ml to 2 mg/ml, or from 1 mg/ml to 1.6 mg/ml, including any subranges and intermediate values between these ranges. In some of the embodiments, the solution of SA50S is concentrated by means commonly used in the art, such as, for example, centrifugation, filtration, dialysis and the likes.

According to some of any of the embodiments of the method described in this context of the present invention, the crystallization solution may further include one or more additives which stabilize the SA50S particle in terms of viability of its proteins and RNA constituents. In some of the embodiments, the additives include buffers, salts, oxidation retardants and the likes, which are used to set or control properties such as ionic strength, pH, chemical composition and the likes. These additives also promote structural stability and viability of various functional groups present in or on the SA50S.

Exemplary crystallization solution additives include, without limitation, non-specific and non-ribosomal antimicrobial agents such as sodium azide, reducing agents that preserve sensitive or labile chemical bonds such as tris(2-carboxyethyl)phosphine (TCEP), dithiothreitol (DTT) or 2-mercaptoethanol, which preserves disulfide bonds, ribosomal stabilizers such as spermidine, ionic agents such as MnCl$_2$, MgCl$_2$, NH$_4$Cl and KCl, pH buffering agents such as Hepes buffer, alcohols and polyols such as ethanol and 2-methyl-2,4-pentanediol.

Other additives that can be used in the crystallization solution according to some embodiments of the present invention include, without limitation, multivalent salts such as barium chloride dihydrate, cadmium chloride hydrate, calcium chloride dihydrate, chromium(III) chloride hexahydrate, cobalt(II) chloride hexahydrate, copper(II) chloride dihydrate, iron(III) chloride hexahydrate, magnesium chloride hexahydrate, manganese(II) chloride tetrahydrate, nickel(II) chloride hexahydrate, praseodymium(III) acetate hydrate, strontium chloride hexahydrate, yttrium(III) chloride hexahydrate, zinc chloride; salts such as ammonium sulfate, cesium chloride, lithium chloride, potassium chloride, potassium sodium tartrate tetrahydrate, sodium chloride, sodium citrate tribasic dihydrate, sodium fluoride, sodium iodide, sodium malonate and sodium thiocyanate; dissociating agent such as phenol, dimethyl sulfoxide and sodium bromide; a linker such as 6-aminohexanoic acid, 1,5-diaminopentane dihydrochloride, 1,6-diaminohexane, 1,8-diaminooctane, glycine, glycyl-glycyl-glycine, taurine and betaine hydrochloride; a polyamine such as spermidine, spermine tetrahydrochloride, hexammine cobalt(iii) chloride and sarcosine; a chaotrope such as trimethylamine hydrochloride, guanidine hydrochloride and urea; a co-factor such as β-nicotinamide adenine dinucleotide hydrate and adenosine-5'-triphosphate disodium salt hydrate; a Reducing Agent such as TCEP hydrochloride, GSH (L-Glutathione reduced) and GSSG (L-Glutathione oxidized); a polymer such as polyvinylpyrrolidone K15, dextran sulfate sodium salt, pentaerythritol ethoxylate (3/4 EO/OH) and polyethylene glycol (PEG); a carbohydrate such as D-(+)-glucose monohydrate, sucrose, xylitol, D-sorbitol, myo-Inositol, D-(+)-trehalose dehydrate and D-(+)-galactose; a polyol such as thylene glycol and glycerol; and other volatile and non-volatile organic additives such as benzamidine hydrochloride, n-dodecyl-N,N-dimethylamine-N-oxide, n-octyl-β-D-gluco side, n-dodecyl-β-D-maltoside, trimethylamine N-oxide dihydrate, 1,6-hexanediol, (+/−)-2-methyl-2,4-pentanediol, polyethylene glycol 400, jeffamine M-600, 2,5-hexanediol, (±)-1,3-butanediol, polypropylene glycol P 400, 1,4-dioxane, ethanol, 2-propanol, methanol, 1,2-butanediol, tert-butanol, 1,3-propanediol, acetonitrile, formamide, 1-propanol, ethyl acetate, acetone, dichloromethane, 1-butanol, 2,2,2-trifluoroethanol and 1,1,1,3,3,3-hexafluoro-2-propanol.

The use of additives in the crystallization solution is well known to a person of ordinary skills in the art of protein crystallization. Alternatively, one can follow guidelines provided in, for example, "*Sparse matrix sampling: a screening method for crystallization of proteins*" [Jancarik, J. and Kim, S.-H., *J. Appl. Cryst.*, 1991, 24(4), p. 409-411], or in "*Improved Success of Sparse Matrix Protein Crystallization Screening with Heterogeneous Nucleating Agents*" [Thakur, A. S. et al, *PLoS One*, 2007, 31, 2(10)].

Exemplary components that can be added to the crystallization solution of SA50S include, without limitation, spermidine (e.g., at a concentration ranging from 2 mM to 10 mM, or from 4 mM to 6 mM or of 5 mM), MnCl$_2$ (e.g., at a concentration ranging, e.g., from 0.1 mM to 1 mM, or from 0.4 mM to 0.6 mM or of 0.5 mM), 20 mM Hepes buffer (e.g., at a concentration ranging from 5 mM to 150 mM, or of 10 mM, 20 mM, 50 mM, 80 mM or 110 mM) set to pH range of from 6.8 to 7.8, MgCl$_2$ (e.g., at a concentration ranging from 1 mM to 20 mM, or of 5 mM, 10 mM or 15 mM), NH$_4$Cl (e.g., at a concentration ranging from 20 mM to 80 mM, or of 30 mM, 40 mM, 50 mM or 60 mM) and/or KCl (e.g., at a concentration ranging from 5 mM to 30 mM, or of 5 mM, 10 mM, 15 mM or 20 mM).

According to exemplary, non-limiting, embodiments, the crystallization solution comprises a concentrated purified preparation of SA50S at a concentration ranging from 0.9 mg/ml to 1.6 mg/ml, 2-methyl-2,4-pentanediol (MPD) at a concentration ranging from 0.1 weight percent to 0.2 weight percent, ethanol at a concentration ranging from 0.3 weight percent to 0.4 weight percent, spermidine at a concentration ranging from 4 mM to 6 mM, MnCl$_2$ at a concentration ranging from 0.4 mM to 0.6 mM, 20 mM Hepes buffer set to pH range of 6.8-7.8, 10 mM MgCl$_2$, 60 mM NH$_4$Cl and 15 mM KCl.

According to some of any of the embodiments of the method described in this context of the present invention, the vapor diffusion conditions include a crystallization solution, as described in any one of the respective embodiments, and/or a reservoir solution, as described in any one of the respective embodiments, having one or more solubilized yet non-volatile component(s), referred to herein as precipitant(s). In some of any of the respective embodiments, the participant(s) is/are found at a higher concentration in the reservoir solution compared to the crystallization solution, such that the gradient of concentration of the precipitant(s) drives a volatile solvent to diffuse via vapor phase from the crystallization solution to the reservoir solution. In some of these embodiments, the concentration of the precipitant in the reservoir solution is higher by at least 1%, 5%, 10%, 20%, 30%, 50%, 100% or 200% or higher, compared to the concentration of the precipitant in the crystallization solution.

Exemplary precipitants usable in the context of the present embodiments include, but are not limited to, a salt, an alcohol, a polyol, a glycol, glycerol, a polyglycol, a polyethylene glycol (PEG) and any mixture thereof. According to some embodiments, the precipitant comprises ammonium sulfate, ethanol and 2-methyl-2,4-pentanediol (MPD), and according to some embodiments, the precipitant comprises ethanol and MPD.

According to some embodiments, the concentration of MPD in the crystallization solution ranges from 0.1 weight percent to 0.3 weight percent, or from 0.15 weight percent to 0.2 weight percent. According to some embodiments, the concentration of ethanol in the crystallization solution ranges from 0.2 weight percent to 0.5 weight percent, or from 0.3 weight percent to 0.4 weight percent. In some of any of the respective embodiments, the crystallization solution includes 0.166% MPD and 0.333% EtOH.

According to some of any of the embodiments of the method described in this context of the present invention, the reservoir solution comprises from 5 weight percent to 15 weight percent MPD, or from 8 to 12 weight percent MPD, and from 3 weight percent to 7 weight percent ethanol, or from 4 weight percent to 6 weight percent ethanol. In some of any of the respective embodiments, the reservoir solution includes 5 weight percent ethanol and 10 weight percent MPD.

Both the crystallization and reservoir solutions further include from 10 mM to 120 mM Hepes buffer set to pH range of 6.8-7.8, from 5 mM to 15 mM MgCl$_2$, from 50 mM to 70 mM NH$_4$Cl and from 10 mM to 20 mM KCl.

According to some of any of the embodiments of the method described in this context of the present invention, under vapor diffusion conditions, the concentration of the precipitant(s) in the crystallization solution increases, thereby driving the ribosomal subunit to gradually precipitate and crystallize over a sufficient period of time, referred to herein as a "first time period".

According to some of any of the embodiments of the method described in this context of the present invention, the first time period ranges from 0.5 day (12 hours) to 60 days, or from 1 day to 10 days, from 2 days to 20 days, from 3 days to 30 days, or from 5 days to 50 days. In some of the respective embodiments, the first time period ranges from 10 days to 20 days.

Once the crystallization solution comes to equilibrium with respect to the reservoir solution, and crystals are formed therein, the crystallization solution is referred to as "mother liquor".

According to some of any of the embodiments of the method described in this context of the present invention, the reservoir solution includes some or all of the components of the crystallization solution. In some of these embodiments, the reservoir solution differs from the crystallization solution by one or more of the concentration of a precipitant, as described herein, and the presence of the entity that is crystallized (the large ribosomal unit). In some of the respective embodiments, the reservoir solution does not contain the entity to be crystallized.

An exemplary crystallization solution which affords SA50S crystals comprises concentrated purified preparation (SA50S) at a concentration that ranges from 0.9 mg/ml to 1.6 mg/ml, from 0.1 weight percent to 0.2 weight percent 2-methyl-2,4-pentanediol, from 0.3 weight percent to 0.4 weight percent ethanol, from 4 mM to 6 mM spermidine, from 0.4 mM to 0.6 mM $MnCl_2$, 20 mM Hepes buffer set to pH range of 6.8-7.8, 10 mM $MgCl_2$, 60 mM $NH_4Cl$ and 15 mM KCl.

According to some of any of the embodiments described for the method of this aspect of the present invention, the method further comprises extracting a plurality of SA50S crystals at the end of the first time period, and subjecting these crystals to conditions that allow these crystals to grow further in size. These crystals, which are extracted in order to allow them to further grow, are referred to as "seeding crystals". It is noted that for structure elucidation using X-ray diffraction data, a large crystal is advantageous as the intensity of the diffracted X-ray is proportional to the size of the crystal.

According to some embodiments of the present invention, the seeding crystals are transferred into a fresh crystallization solution, prepared as described hereinabove. The fresh crystallization solution, referred to herein as a "re-crystallization solution", can be the same as the initial crystallization solution or different in terms of its contents or the concentration of one or more of its components. For example, the content of the ribosomal subunit can be higher or lower than its concentration in the initial crystallization solution.

According to some embodiments of the present invention, the seeding crystals are washed before being transferred to the re-crystallization solution. In the context of embodiments of the present invention, washing the crystals refers to contacting the seeding crystals with a solution which is similar to the mother liquor or the reservoir solution but does not contain the entity to be crystallized (e.g., a ribosomal subunit). Without being bound to a particular theory, it is assumed that washing the seeding crystals in the abovementioned washing solution involves re-solubilizing some of the particles on the faces of the seeding crystals, thereby exposing fresh and ordered parts of the crystal lattice. The freshly exposed lattice will serve for growth of the crystal in an orderly fashion by essentially extending the pre-formed lattice of the seeds.

According to some of any of the embodiments of the method described in this context of the present invention, the washing solution comprises from 7 weight percent to 8 weight percent MPD, and from 7 weight percent to 8 weight percent ethanol. The washing solution may further include some of the components present in the crystallization solution, such as, for example, 110 mM Hepes buffer set to pH range of 6.8-7.8, 10 mM $MgCl_2$, 60 mM $NH_4Cl$ and 15 mM KCl buffer and 0.5 mM $MnCl_2$.

According to some of any of the embodiments described for the method of this aspect of the present invention, the method further comprises subjecting the re-crystallization solution which includes one or more seeding crystals, to vapor diffusion conditions for a second time period. In some of the respective embodiments described herein, the second time period typically ranges from 1 day to 60 days, or from 1 day to 10 days, from 2 days to 20 days, from 3 days to 30 days, or from 5 days to 50 days, or from 10 days to 50 days, including any subranges and intermediate values therebetween. In some of the respective embodiments, the second time period ranges from 10 days to 40 days or from 2 weeks to 4 weeks.

Seeding crystals of SA50S are placed, after the optional washing step, in a re-crystallization solution which is allowed to equilibrate against a reservoir solution in essentially the same vapor diffusion conditions described herein.

According to some embodiments, the SA50S crystals, namely the seeding crystals and/or the seeded and enlarged SA50S crystals (macro crystal), are further transferred to a stabilization solution after the first or second time periods in order to maintain the crystals soaked at optimal conditions and ready for exposure to X-ray radiation. Typically, the stabilization solution contains a higher precipitant concentration which keeps the SA50S (the crystallized particles) from re-solubilizing.

According to some of any of the embodiments of the method described in this context of the present invention, the precipitant in the stabilization solution comprises from 10 weight percent to 20 weight percent MPD and from 10 weight percent to 20 weight percent ethanol. In some of the respective embodiments, the stabilization solution comprises from 10 weight percent to 25 weight percent MPD, from 10 weight percent to 20 weight percent ethanol, and further includes other components of the crystallization solution, such as, for example, 110 mM Hepes buffer set to pH range of 6.8-7.8, 10 mM $MgCl_2$, 60 mM $NH_4Cl$ and 15 mM KCl.

According to some embodiments of the present invention, the crystal is flash-cooled (flash-frozen) to cryogenic temperatures and the X-ray diffraction data collection is carried out under cryogenic conditions. In such embodiments, the SA50S crystals are typically soaked in a stabilization solution that further contains a cryoprotectant.

The term "cryoprotectant", as used herein, refers to a substance that is added to an aqueous solution containing a sample, such as a biological sample, in order to protect the sample from rapid formation of extended ice crystals therein, otherwise referred to as freezing damage. Hence, the term "cryoprotectant solution" is used herein to refer to a stabilization solution which includes a cryoprotectant.

According to some of any of the embodiments of the method described in this context of the present invention, the cryoprotectant is an alcohol, a polyalcohol, a saccharide (a carbohydrate), a polysaccharide, a polyol, a glycol, a polyglycol, a polyethylene glycol (PEG) and any mixture thereof. Exemplary cryoprotectants include, without limitation, DMSO, ethylene glycol, glycerol, MPD, propylene glycol and sucrose. In some of the respective embodiments, the cryoprotectant includes ethanol and MPD.

According to some of any of the embodiments of the method described in this context of the present invention, prior to the cryogenic flash-freezing, the crystals of the ribosomal subunit, e.g., SA50S, are soaked in a cryoprotectant solution. According to some embodiments, the precipitants are similar to the cryoprotectants, and in some of the respective embodiments the stabilization solution can serve as a cryoprotectant solution. In some of the respective embodiments, the concentration of the precipitants/cryoprotectants is adjusted so as to afford cryogenic protection to the ribosomal subunit crystals, typically by using higher concentration of the precipitants in the cryoprotectant solution.

According to some embodiments, the precipitant in the cryoprotectant solution comprises from 10 weight percent to 25 weight percent MPD and from 10 weight percent to 20 weight percent ethanol, and further includes other components of the crystallization solution, such as, for example, 110 mM Hepes buffer set to pH range of 6.8-7.8, 10 mM $MgCl_2$, 60 mM $NH_4Cl$, 15 mM KCl and 0.4-0.6 mM $MnCl_2$.

According to some embodiments of the present invention, the ribosomal subunit, e.g., SA50S, is further associated with (complexed with) a ligand that diffuses into the crystal and is associated essentially with the crystallized ribosomal subunits. According to some embodiments, the ligand is added to the stabilization solution, whereas the stabilization solution that comprises a ligand is referred to herein as a "soaking solution".

According to some of any of the embodiments of the method described in this context of the present invention, the macro crystals are soaked in the soaking solution in order to introduce a ligand to the ribosomal subunit in the crystals. In some of the respective embodiments, the ligand is as defined in any of the respective embodiments described herein. In some of the respective embodiments, the ligand is an antibacterial agent that binds to a binding site in the crystallized ribosomal subunit. In some of the respective embodiments, the concentration of the ligand in the soaking solution ranges from 1 µg/ml to 30 µg/ml.

An exemplary crystallization method of the SA50S ribosomal subunit is described in the Examples section that follows. The crystallization method exemplified below has been used to obtain a composition-of-matter comprising crystals of the large ribosomal subunit of *Staphylococcus aureus* which were used to obtain X-ray diffraction data to resolution of at least 4 Å.

The exemplary SA50S crystals in an exemplary composition-of-matter as described herein can be used to obtain X-ray diffraction data according to any method, process or X-ray source as known in the art. According to some embodiments, the data collection is carried out using a collimated X-ray beam at a high brightness synchrotron station.

A Computer System Comprising Structural Information:

The X-ray diffraction data collected using the herein-provided composition-of-matter that comprises a crystallized form of a large ribosomal subunit of a pathogenic bacterium (excluding *Escherichia coli*), a pathogenic Gram positive bacterium, or a pathogenic bacterium exhibiting degree of 23S rRNA sequence identity of at least 80% compared to the 23S rRNA of *Staphylococcus aureus*, such as the SA50S subunit, can be stored, processed and analyzed on a computer system that can further be used to elucidate the three-dimensional structure thereof.

In some of any of the respective embodiments of the present invention, the X-ray diffraction data is subjected to a computational molecular replacement procedure which assigns a phase to each of the diffracted reflections. In some of the embodiments, the molecular replacement procedure utilizes an experimentally-obtained or a calculated structure of a 50S subunit of another species, such as, but not limited to, the structure of the 50S subunit of *D. radiodurans* (D50S), having PDB ID: 2ZJR, which is used as a starting model.

The computer system can further be used, after the molecular replacement procedure, to provide positioning data indicative of atomic coordinates of the large ribosomal subunit. Typically, atomic coordinates are obtained by following a procedure wherein the computational atomic model of the large ribosomal subunit is built computationally into a graphic representation of the electron density map, which is computationally constructed from the experimentally recorded intensities and the calculated phases of the X-ray reflections. Then, an atomic model is computationally refined using a computational refinement procedure that further improves the calculated estimation of the phases iteratively, leading to a better defined calculated electron density map.

Thus, the computer system includes positioning data, which define the structural information of the large ribosomal subunit, either in its native form or in its ligand-bound state (a complex with a ligand), being recorded on one or more data-storage device forming a part of the computer system. The computer system includes software (computer programs) that can be used to compare that structural information to structural information of other ribosomal particles, provide and use protein and RNA sequence alignments and use the latter to model various structures, identify and analyze the molecular surface of various binding sites in the large ribosomal subunit, and provide structural data pertaining to putative ligands of the large ribosomal subunit.

According to some embodiments of the present invention, the atomic coordinates of the exemplary native (ligand-free) SA50S subunit are deposited at the Protein Data Bank under accession number PDB ID: 4WCE. It is noted herein that the phrase "atomic coordinates which are deposited at the Protein Data Bank under accession number PDB ID: 4WCE" refers to an embodiment of the positioning data pertaining to the native (ligand-free) SA50S ribosomal subunit, which has been determined using X-ray diffraction data obtained by using a composition-of-matter disclosed herein. It is further noted that the contents of the entry deposited at the Protein Data Bank under accession number PDB ID: 4WCE are provided herein, as an electronic document denoted "4WCE_SA50S_Native.pdb.txt".

Thus, according to some embodiments of an aspect of the present invention, there is provided a computer system that includes, without limitation:

(a) at least one data-storage device having stored therein positioning data indicative of atomic coordinates of a large ribosomal subunit of a pathogenic bacterium, wherein the pathogenic bacterium is a pathogenic Gram positive bacterium; and/or a pathogenic bacterium exhibiting a degree of 23S rRNA sequence identity of at least 80% compared to rRNA of *Staphylococcus aureus*; and/or a pathogenic bacterium exhibiting a degree of 23S rRNA sequence identity of less than 99.9% compared to rRNA of *Escherichia coli*, such as, for example, PDB ID: 4WCE which contains the atomic coordinates of the SA50S ribosomal subunit, which can be determined from an electron density map having a resolution of at least 4 Å calculated from X-rays diffraction data obtained using at least one crystal in the composition-of-matter presented herein; and (b) a processing unit in electrical communication with the data-storage device; and (c) a program for calculating a three-dimensional model representative of the ribosomal subunit from the set of atomic coordinates.

The computer system may further include a device for providing a visual representation of the three-dimensional model, namely a display (screen). The visual display may present the three-dimensional model of the instantly provided SA50S structure as an electron density map, a ball-and-stick model, a space-filling (Calotte) model, a secondary structure (ribbon) model, a molecular surface model, a skeletal model and the likes and any combination thereof, each of which is aimed at showing the relative positions of various attributes the atoms making up the SA50S subunit as captured in the crystal structure. The computer system is configured to present the entire SA50S or any parts and portions thereof, and further display entire or part of structures of other molecular entities, including ligands, putative designed ligands and/or structures of other ribosomal subunits in any combination with the molecular model of the SA50S subunit.

The computer system may further include various components which form part of the system and include, without limitation, input/output controllers and devices, memory modules, hard drives, discs and other form of magnetic and optic data storage controllers and devices, various ports and connectivity controllers and devices, network controllers and devices and the likes. It is noted that the computer system presented herein may be wholly or partially operated as could computing system (decentralized computing system), having one or more remote servers networked therewith for decentralized data storage and processing, and other forms of online access to decentralized computer services or decentralized resources.

According to some embodiments of the present invention, the computer system further includes the atomic coordinates of complexes of the large ribosomal subunit with various ligands bound thereto, such as antibacterial agents. Exemplary ligands include antibacterial agents such as linezolid, BC-3205 and telithromycin, as these are deposited at the Protein Data Bank under accession number selected from the group consisting of PDB IDs: 4WFA, 4WFB and 4WF9, respectively. It is noted herein that the phrase "atomic coordinates which are deposited at the Protein Data Bank under accession number PDB IDs: 4WFA, 4WFB and 4WF9" refers to an embodiment of the positioning data pertaining to the SA50S ribosomal subunit in a complex (bound state) with each of the ligands linezolid, BC-3205 and telithromycin respectively, which have been determined using X-ray diffraction data obtained by using a composition-of-matter disclosed herein.

It is further noted that the contents of each of the entries deposited at the Protein Data Bank under accession number PDB IDs: 4WFA, 4WFB, 4WF9, 5HL7 and 5HKV are provided herein, each as an electronic document denoted "4WFA_SA50S_lin.pdb.txt",
"4WFB_SA50S_bc3.pdb.txt",
"4WF9_SA50S_teli.pdb.txt", "SA50S_lefamulin.pdb.txt" and "SA50S_lincomycin.pdb.txt", respectively.

According to some of any of the embodiments presented herein, the atomic coordinates comprise atomic coordinates of at least one ribosomal RNA (rRNA) and further comprises atomic coordinate of at least one ribosomal protein (rProtein).

In addition to the atomic coordinates and protein and RNA sequence data of the large ribosomal subunit, the computer system may further include protein and RNA sequence and atomic coordinates of other ribosomal subunits. For example, the data-storage device of the computer system include the atomic coordinates and/or the sequence data of ribosomal subunits from *Staphylococcus aureus, Thermus thermophilus, Escherichia coli, Haloarcula marismortui, Deinococcus radiodurans* and *Saccharomyces cerevisiae, Tetrahymena thermophila*.

In some of any of the embodiments of the present invention, the atomic coordinates of *D. radiodurans* comprise at least a portion of the atomic coordinates deposited at the Protein Data Bank under accession number selected from the group consisting of PDB IDs: 2ZJR, 3DLL, 2OGM, 2OGN, 2OGO, 1XNP, 1SM1, 1P9X, 1JZY and 4U67.

In some of any of the embodiments of the present invention, the atomic coordinates of *E. coli* comprise at least a portion of the atomic coordinates deposited at the Protein Data Bank under accession number selected from the group consisting of PDB IDs: 2AW4, 3R8S, 3OAT and 3OFR.

In some of the respective embodiments of the present invention, the atomic coordinates of *T. thermophilus* comprise at least a portion of the atomic coordinates deposited at the Protein Data Bank under accession number selected from the group consisting of PDB IDs: 2WDL, 2WDK, 3OI3 and 3OHD.

In some of the respective embodiments of the present invention, the atomic coordinates of *H. marismortui* comprise at least a portion of the atomic coordinates deposited at the Protein Data Bank under accession number selected from the group consisting of PDB ID: 1S72, 3CC2 3CPW and 1YIJ.

In some of the respective embodiments of the present invention, the atomic coordinates of *T. thermophila* comprise at least a portion of the atomic coordinates deposited at the Protein Data Bank under accession number selected from the group consisting of PDB ID: 4A17, 4A18, 4A19, 4A1A, 4A1B, 4A1C, 4A1D and 4A1E.

In some of the respective embodiments of the present invention, the atomic coordinates of *S. cerevisiae* comprise at least a portion of the atomic coordinates deposited at the Protein Data Bank under accession number selected from the group consisting of PDB ID: 3U5B, 3U5C, 3U5D, 3U5E, 3U5F, 3U5G, 3U5H and 3U5I.

Using sequence alignment and experimental structural information, the structure of ribosomal particles which have not yet been obtained experimentally can be calculated computationally; hence, the data-storage device of the computer system presented herein may further include the structure of a host of a pathogenic bacterium. A host organism can be a mammalian, thus the computationally-calculated structure of a ribosomal subunit can even be the structure of a human ribosome, or at least some subunits and/or parts thereof. Such a structure can be used to gain insights on the minute structural differences between pathogenic and human host ribosome, allowing the design of de novo ligands which will be selective towards the pathogenic species and substantially inactive towards the host.

The atomic coordinates of any one of the SA50S native and complex structures, include the atomic coordinates of at least one binding site in the SA50S subunit. As used herein, the term "binding site" refers to a region on a protein, DNA, RNA or a combination thereof, to which specific molecules and/or ions (ligands) may bind to reversibly or irreversibly. As known in the art, ribosomal subunits comprise a plurality of binding sites which have been identified by various experimental methods including crystal structure elucidation, and some of those binding site have been identified or attributed to the large ribosomal subunit. It is noted that some binding site may be attributed to more than one subunit since these binding sites are defined by atoms which belong to more than one subunit, e.g., a binding site which is found at the interface between the small and large subunits.

According to some embodiments of the present invention, the term "binding site" refers to a locus in or on the ribosomal subunit which is related to one of more ribosomal functions in the sense that when being occupied by a ligand or freed thereof, the ribosomal function is altered. A binding site which is associated with a ribosomal functional is also referred to herein as a "ribofunctional locus". According to some embodiments, the term "ribofunctional locus" refers to a region of the ribosome or ribosomal subunit that participates, either actively or passively, in decoding of the genetic information (translation), or in protein or polypeptide synthesis within the ribosome or ribosomal subunit and/or export or translocation of a protein or polypeptide out of a ribosome.

Exemplary binding sites, or ribofunctional loci, which are associated with the large ribosomal subunits, the atomic coordinates of at least a portion of which are part of the atomic coordinates of the large ribosomal subunit of a pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, such as, e.g., SA50S, include without limitation an inter-subunit interface, a peptidyl transferase site, a GTPase center, an mRNA binding site, an A-site, a P-site, an E-site, a polypeptide exit tunnel, a translation initiation factor (IF1) binding site, a translation initiation factor (IF2) binding site, a translation initiation factor (IF3) binding site, an elongation factor G (EF-G) binding site, elongation factor Tu (EF-Tu) binding site, hibernation factor HPF binding site, hibernation factor RMF binding site, hibernation factor YfiA binding site, a GTP binding site and a ricin binding site.

According to embodiments of some aspects of the present invention, there is provided a computer readable medium comprising at least a portion of the positioning data in a retrievable format, which is indicative of atomic coordinates determined from an electron density map calculated from X-rays diffraction data obtained using a crystallized large ribosomal subunit of the pathogenic bacterium in the composition-of-matter provided herein.

As used herein, the term "computer readable medium" refers to any medium which can be read and accessed directly by a computer. Such media include, but are not limited to, a magnetic storage media, such as floppy discs, hard disc storage medium, and magnetic tape; optical storage media such as optical discs or CD-ROM; electrical storage media such as RAM and ROM; and hybrids of these categories such as magnetic/optical storage media; a solid-state memory device; an acoustic data; a chemically or photochemically recorded data; and any other machine-readable medium or automated data medium format known in the art. A skilled artisan can readily appreciate how any of the presently known computer readable mediums can be used to create an article comprising computer readable medium having recorded thereon an amino acid and/or nucleotide sequence, X-ray diffraction data, and/or atomic coordinates of the present invention.

As used herein, the term "recorded" refers to any process for storing information on computer readable medium. A skilled artisan can readily adopt any of the presently known methods for recording information on computer readable medium to generate articles comprising computer readable medium having recorded thereon an amino acid or nucleotide sequence, atomic coordinates and/or X-ray diffraction data of the present invention.

The computer readable medium can further include, according to some embodiments of the present invention, the X-ray diffraction data as a collection of digitized images, a list of reflection indexes and corresponding intensities and reflection spread, or any other format of recording the direct experimental results of the X-ray diffraction data obtained from a crystal of a large ribosomal subunit of a pathogenic bacterium.

The computer readable medium can further include, according to some embodiments of the present invention, atomic coordinates and/or rProtein/rRNA sequence data of any other ribosomal subunit, obtained either experimentally or computationally.

The computer readable medium can further include, according to some embodiments of the present invention, atomic coordinates of any known or putative ligand of any ribosomal subunit, a putative ligand of a large ribosomal subunit of a pathogenic bacterium, a pathogenic Gram positive bacterium, or a pathogenic bacterium exhibiting a degree of 23S rRNA sequence identity of at least 80% compared to the 23S rRNA of *Staphylococcus aureus*, such as, e.g., SA50S; while the putative ligand can be obtained using computer-aided structure-based drug design methodologies known in the art.

It is noted that comparative structural superimposition and sequence alignment comparisons and analysis, using the computer system provided herein and including the structure of a large ribosomal subunit of a pathogenic bacterium provided herein, can be used, according to embodiments of the present invention, to find structural differences between various ribosomal subunits, which can be exploited in the design of ligands that will exhibit species-specific affinity towards specific binding sites.

Computer-Aided Structure-Based Drug Design:

According to some embodiments of the present invention, the atomic coordinates of any ribosomal subunit, whether determined using X-ray diffraction, molecular modeling, homology modeling or molecular replacement, as these terms are known in the art, may be used in rational drug design (RDD) to design de novo ligands which can be used, for example, as novel modulators, inducers, mimetics or inhibitors of ribosomal function, which generally relate to cellular protein synthesis. It is has been contemplated by the present inventors that by using, for example, the SA50S subunit structure disclosed herein and the principles of RDD and computer-aided/assisted drug design (CADD), an ordinary skilled artisan can design, prepare, test, refine and use de novo protein synthesis inhibitors specifically engineered to reduce, induce, disrupt, augment or otherwise affect cellular ribosomal function in an organism or species of interest. For example, by using the principles discussed herein, the skilled artisan can engineer de novo ligands that specifically target and inhibit ribosomal function in a pathogenic bacterium, for example, a particular cocci bacterium, while preserving ribosomal function in a host, for example, a eukaryotic organism, specifically a mammal, and more specifically, a human. As a result, the atomic coordinates provided and discussed herein permit the skilled artisan to design de novo antibacterial agents that can kill certain pathogenic organisms while having little or no toxicity in the intended recipient, for example, a human, or to non-pathogenic bacteria that reside in the host.

It has been contemplated that structure-based drug design procedures using atomic coordinates of the large ribosomal subunit, according to any embodiment of the present invention, including that of a pathogenic bacterium, a pathogenic Gram positive bacterium, or a pathogenic bacterium exhibiting a degree of 23S rRNA sequence identity of at least 80% compared to the 23S rRNA of *Staphylococcus aureus*, such as, e.g., SA50S subunit, can be facilitated most readily via CADD using conventional computer hardware and software known and used in the art and discussed hereinabove.

It is noted that computer-aided drug design methods can utilize experimentally obtained positioning data of one target molecule, such as the structure if the SA50S subunit, to design ligands for large ribosomal subunits of other species, particularly other genetically-related bacteria, based on the non-limiting theory that their three-dimensional structure is similar due to a relatively high degree of identity in their 23S rRNA sequence (see, "degree of 23S rRNA sequence identity" hereinabove). Hence, the computer-aided drug design procedure can utilize the atomic coordinated of the SA50S subunit, as provided herein.

The putative ligands may be designed de novo or may be designed as a modified variant of an already known (pre-existing) ligand, for example, a pre-existing antibacterial agent or a conjugate of one or more pre-existing ligands and/or fragments thereof. According to some embodiments of the present invention, pre-existing ligands or pre-existing antibacterial agents are ligands and antibacterial agents which have been pre-verified by in-vitro and/or in-vivo bioactivity assays and found to have an affinity to the ribosome or ribosomal subunit of interest, using conventional methodologies. In some of any of the respective embodiments of the present invention, a putative ligand is having a molecular weight of less than about 1,500 grams/mol.

Once designed, putative ligands can be synthesized using standard methodologies known and used in the art. Following synthesis, the candidate molecules can be screened for bioactivity, for example, by their ability to reduce or inhibit ribosome function, their ability to interact with or bind to a ribosome or a ribosomal subunit once contacted with the ribosome or the ribosomal subunit. Based in part upon these results, the candidate molecules may be refined iteratively using one or more of the foregoing steps to produce a ligand with a more desirable biological activity. In general, a more desirable biological activity typically refers to a ligand exhibiting a high affinity (strong binding) and a high specificity and thus selective affinity towards a ribosome of a particular species, allowing the use of the ligand as an antibiotic drug requiring clear distinction between the pathogen and the mammalian host, low doses to eradicate a target pathogenic organism while exhibiting minimal adverse effects on the host organism.

The computer system provided herein may further include CADD programs, databases and other software components for calculating at least one structure of a putative ligand for binding to at least one binding site in, for example, the SA50S subunit. A computer-aided drug design program suit may include general purpose molecular modeling programs such as, but not limited to structure alignment program for superimposing atomic coordinates of independently-obtained structures; molecular mechanics, molecular dynamics and multifunctional programs which can be used to calculate a molecular model of a ribosomal subunit even without experimentally-obtained structural data; quantum chemistry calculations for small molecules; molecular orbital or quantum mechanical calculations; database of molecular structures of large and small molecules; software for storage and retrieval of molecular structure data; molecular graphic software for large and small molecules; and programs to visualize molecules.

Exemplary software for general purpose molecular modeling and computer-aided drug design include without limitation AMBER by Peter Kollman and coworkers; Midas Plus by UCSF Computer Graphics Laboratory; CHARMM by Martin Karplus and coworkers; QUANTA/CHARMm by Molecular Simulations Inc. (MSI); Insight/DISCOVER by Biosym, Inc.; SYBYL and Alchemy III by Tripos, Inc.; ECEPP by Harold Scheraga and coworkers; MM3 by Norman Allinger and coworkers; Chem3D Pro by Cambridge-Soft Corp.; Desktop Molecular Modeller by Oxford Elec. Publishing; Molecular Modeling Pro by WindowChem Software; and PC MODEL by Serena Software.

Additional computer programs useful for viewing or manipulating three-dimensional structures include: Midas (University of California, San Francisco); MOIL (University of Illinois); Yummie (Yale University); MacroModel (Columbia University); Cerius (Molecular Simulations, Inc.); LabVision (Tripos, Inc.); Rasmol (Glaxo Research and Development); Ribbon (University of Alabama); NAOMI (Oxford University); Explorer Eyechem (Silicon Graphics, Inc.); Univision (Cray Research); Molscript (Uppsala University); Chem-3D (Cambridge Scientific); Chain (Baylor College of Medicine); O (Uppsala University); GRASP (Columbia University); X-Plor (Molecular Simulations, Inc.; Yale University); Spartan (Wavefunction, Inc.); Catalyst (Molecular Simulations, Inc.); Molcadd (Tripos, Inc.); VMD (University of Illinois/Beckman Institute); Sculpt (Interactive Simulations, Inc.); Procheck (Brookhaven National Library); DGEOM (QCPE); RE_VIEW (Brunell University); Modeller (Birbeck College, University of London); Xmol (Minnesota Supercomputing Center); Protein Expert (Cambridge Scientific); HyperChem (Hypercube); MD Display (University of Washington); PKB (National Center for Biotechnology Information, NIH); ChemX (Chemical Design, Ltd.); Cameleon (Oxford Molecular, Inc.); and Iditis (Oxford Molecular, Inc.).

Exemplary databases that may be used in the computer-aided drug design based on the structure of a large ribosomal subunit of a pathogenic bacterium, such as the SA50S subunit structure presented herein, include, without limitation, structural data of various homologous ribosomal subunits obtained from X-ray diffraction, NMR and other structure determination procedures; protein and nucleic acid sequence data; quantitative structure-activity relationship (QSAR of conventional compound synthesis and combinatorial chemistry) and other chemical data.

The computer-aided drug design based on the structure of a large ribosomal subunit of a pathogenic bacterium presented herein, such as the SA50S subunit structure, may further include the use of molecular energy parameters pertaining to structural geometry and folding, molecular dynamics parameters pertaining to conformational changes, and molecular recognition parameters pertaining to putative ligand design.

The computer-aided drug design based on the availability of atomic coordinated (structure) of, for example, the SA50S subunit presented herein may further include the use of de novo ligand design methods which include, without limitation, fragment location methods, site point connection methods, fragment connection methods, sequential buildup methods, whole molecule methods, random connection methods and the likes computational procedures known in the art.

Determining desirable locations of atoms or small fragments within a binding site on SA50S in the computer-aided drug design based on the SA50S subunit structure presented herein may be accomplished by using GRID by Goodford and coworkers; GREEN by Itai and coworkers; HINT by Kellogg and coworkers; Dean by Lewis and coworkers; CAVEAT by Bartett and coworkers; and HOOK by Hubbard and coworkers.

The computer-aided drug design based on the SA50S subunit structure presented herein may further include the use of molecular surface matching (docking) and binding scope evaluation methods, which are aimed at fitting known compounds into a binding site in various orientations, assessing shape and/or electrostatic complementarity and other chemical and physical parameters. Such methods are implemented in software suits which include, without limitation, Dock by Kuntz and coworkers; AUTODOCK by Olsen and coworkers; and various Monte Carlo approaches.

The computer-aided drug design based on the SA50S subunit structure presented herein may make use of general purpose CADD suites including combinatorial chemistry software for structural accuracy and specificity and for rapid synthesis procedures and structural diversity.

Hence, according to some embodiments of the present invention, the data-storage device(s) in computer system may further include the atomic coordinates of a putative ligand, which has been designed for binding to one of the binding sites in the large ribosomal subunit, wherein the putative ligand is a product of a computer-aided drug design procedure being a structure-based drug design, namely the putative ligand is designed based on a structure of at least one binding site in the large ribosomal subunit of a pathogenic bacterium, such as the presently provided SA50S subunit.

Identifying Ligands of Ribosomal Subunits:

The tools and methodologies provided herein may be used to identify and/or design ligands which bind and/or interact in desirable ways with ribosomes and ribosomal subunits. Basically, the procedures utilize an iterative process whereby the ligands are designed, prepared, tested and characterized. De novo ligands can be designed based on the information gained in the testing and characterization of the initial molecules and then such newly identified molecules can themselves be tested and characterized. This series of processes may be repeated as many times as necessary to obtain molecules with desirable binding properties and/or biological activities. Methods for identifying candidate molecules are discussed in more detail below.

According to some embodiments of an aspect of the present invention, there is provided a method for designing and selecting a putative ligand having an affinity to a binding site of a large ribosomal subunit of a pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, such as the large ribosomal subunit of *Staphylococcus aureus*. According to some embodiments, the ligand exhibits high affinity and high specificity to the ribosomal subunit.

The method can be implemented using a computer system that includes the atomic coordinates (positioning data or structure) of a large ribosomal subunit of a pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, such as the SA50S subunit, and sequence data and software as described hereinabove. According to some embodiments, the design of a putative ligand can be facilitated using conventional computer systems available commercially from, for example, Silicon Graphics Inc. and Sun Microsystems, running, for example, UNIX based, Windows NT on IBM OS/2 operating systems, and capable of running conventional computer programs for molecular modeling and rational drug design. It is noted herein that any computer system having the overall characteristics of a typical computer system may be useful in the practice of the invention. Specifically, a typical computer system typically include input, processing, storage and output components in electrical communication with one another via, for example, an internal bus or external network, a central processing unit, a random access memory (RAM), a read only memory (ROM), a monitor or terminal, and optimally an external or internal data-storage device, for example, a diskette, CD ROM, or magnetic tape or a solid-state memory device. A decentralized (cloud based) computer system is also contemplated within the scope of the present invention.

According to some embodiments of the present invention, a putative ligand that can bind to a ribosomal subunit of a pathogen at a desired affinity and thus inhibit its protein biosynthesis can be designed entirely de novo or may be based upon a pre-existing (pre-verified) protein biosynthesis inhibitor(s). Either of these approaches can be facilitated by computationally screening databases and libraries of small molecules for chemical entities, agents, ligands, or compounds that can bind in whole, or in part, to ribosomes and ribosomal subunits, more preferably to large ribosomal subunits, more preferably to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, and more preferably to SA50S ribosomal subunit. In this screening, the quality of fit of such entities or compounds to the binding site or sites may be judged either by shape complementarity or by estimated interaction energy.

Briefly, the method comprises:

(a) obtaining positioning data indicative of atomic coordinates of at least one binding site of the large ribosomal subunit of a pathogenic bacterium, as defined herein, such as the SA50S subunit as provided herein;

(b) calculating the molecular surface of the binding site while denoting, for example, solvent accessible surface, charged functionalities and groups, hydrophobicity, hydrogen-bond donors/acceptors, and other chemical and physical characteristics of the molecular surface, using a suitable computer program;

(c) computationally constructing at least one chemically feasible ligand having a molecular surface that matches the molecular surface of a binding site of choice, namely a ligand exhibiting a pharmacophore corresponding to a binding site of choice, using suitable computer programs that correlate the molecular surface attributes provided in step (b) with feasible and matching chemical scaffolds and functional groups in the ligand.

In some of the respective embodiments of the present invention, the method further comprises computationally constructing a library of structures of chemically feasible ligands having a molecular surface that matches the molecular surface of the binding site (each exhibiting a pharmacophore corresponding to a binding site of choice):

(d) computationally determining a matching/binding score for each of the designed ligands, using docking algorithms that account for energy minimization, structural geometry constrains, shape and/or electrostatic complementarity and the likes; and (e) based on the matching score, selecting at least one putative ligand having a desired affinity to the molecular surface of the binding site of the large ribosomal subunit of a pathogenic bacterium.

According to some embodiments of the present invention, characterizing the binding of a ligand of the ribosomal subunit comprises obtaining or synthesizing a ligand, contacting the ligand with the ribosomal subunit thereby forming a complex thereof, and analyzing the complex by X-ray crystallography.

In some of any of the respective embodiments of the present invention, the search for a ligand of the large ribosomal subunit of a pathogenic bacterium can be based on a computerized search for complementarity of members of a library of known ligand structures. Such a search may provide insights for further manipulations of the known ligands, as well as serve as an advantageous starting model for de novo designed ligands. According to some embodiments, the library may include various chemically feasible variants of pre-existing ligands, namely a set of ligands which are based on a known ligand which has been modified computationally while observing feasible chemistry constrains and while allowing a wide range of chemically diverse variations.

According to some embodiments, a set of known and pre-verified ligands and variants thereof undergo the procedure of Step (d) as the de novo designed ligands of Step (c).

The procedure for computationally designing, docking and scoring the binding affinity of putative de novo designed ligands and/or modified ligands and/or modified known ligands, as described herein, can be repeated, according to some embodiments, using a molecular surface of the same binding site in a ribosomal subunit of another species, such as a host or a benign (non-pathogenic) species. A high affinity to a molecular surface can be seen as a match between the ligand and the target at that binding site, and a lower affinity to a molecular surface can be seen as a mismatch between the ligand and the target at that binding site. Such a procedure provides a list of putative ligands (a library) which exhibit a species-specific binding affinity, namely, ligands may be identified also according to a higher affinity to the ribosomal subunit of a pathogenic and a relatively lower affinity to the ribosomal subunit of the other organism.

A list of non-limiting examples of antibiotic binding sites in the SA50S is provided in the Examples section that follows below. A list of non-limiting examples of regions where structural differences have been identified between the SA50S and the corresponding regions in other ribosomal subunits is provided in the Examples section that follows below. The skilled artisan in possession of the foregoing or other exemplary binding sites may use the method for designing a ligand of the SA50S subunit provided herein to identify ligands that potentially bind to one or more of the binding sites and/or inhibit ribosomal activity. Furthermore, by taking into account which of the residues that define the target site are conserved in terms of sequence similarity between pathogens but not conserved between host species, the skilled artisan can design new species-specific protein synthesis inhibitors.

As known in the art, ribosomes from bacteria, archaea and eukaryotes differ in their size, sequence, structure, and the ratio of protein to RNA. The differences in structure allow some antibiotics to kill bacteria by inhibiting functions (e.g., protein synthesis) of their ribosomes, while leaving eukaryotic ribosomes (e.g., those of a host organism such as a human) unaffected. It is appreciated that the skilled artisan can take advantage of the regions that are not conserved between a bacterial pathogen and a eukaryotic host organism to provide target regions for rational drug design. By way of example, FIG. 14A shows certain regions of the erythromycin tunnel entrance binding pocket that are conserved between *Staphylococcus aureus* and *S. cerevisiae* and regions of the same pocket that are not conserved between *Staphylococcus aureus* and *S. cerevisiae*, where *S. cerevisiae* serves as a representative of a eukaryotic organism. In addition, the skilled artisan when in possession of mutations that prevent or reduce antibiotic activity (i.e., are related to antibiotic resistance) can use this information to model the relevant antibiotic binding product which can then be used as a basis for rational drug design to identify small molecules, having, for example, a molecular weight of less than about 1,500 grams/mol, that overcome drug resistance. It is contemplated that a variety of computer modeling procedures, for example, homology modeling protocols, can be used to provide a model of a drug resistance target site by implementing site directed mutagenesis of nucleotides and/or amino acids and then using the appropriate energy minimization and refinement protocols.

Starting with the structure of the exemplary SA50S ribosomal subunit provided herein, as well as other known structure of the large ribosomal subunit of other species, the structure of the ribosome from a non-targeted organism (for example, the human 60S ribosomal subunit) can be constructed by homology modeling, i.e., by changing the structure of residues at a target site of interest for the residues at the same positions in of the non-target ribosome. This can be achieved by removing computationally the side chains from the ribosome of known structure and replacing them with the side chains of the unknown structure put in sterically plausible and chemically feasible positions. In this way, it can be understood how the shapes of the target sites within the targeted and non-targeted ribosomes differ. This process, therefore, provides information concerning how a molecule that binds the target site can be chemically altered in order to produce ligands that bind tightly and specifically to the targeted ribosome but will simultaneously be prevented from binding to the non-targeted ribosome.

Accordingly, knowledge of portions of the bound ligands that face the solvent permits introduction of other functional groups for additional pharmaceutical purposes. The process of homology structure modeling can also be used to understand the mechanisms whereby mutant ribosomes become resistant to the effects of pharmaceuticals. Furthermore, with knowledge of the regions in a large ribosomal subunit of a pathogenic bacterium that participates in drug resistance, the skilled artisan may design new ligands that overcome the problem of drug resistance.

The use of homology structure modeling to design ligands that bind more tightly to the target ribosome than to the non-target ribosome has wide-spread applicability. The methods outlined herein can be used to control any targeted organism, for example, a pathogenic bacterium, by designing molecules that inhibit large ribosomal subunits of the targeted organisms while failing to inhibit the 50S or 60S ribosomal subunit of the non-targeted organism, for example, a host, to the same extent or not at all. The molecules identified or prepared by the methods of the present invention can be used to control the targeted organisms while causing the non-targeted organism little or no adverse effects. Thus, the ligands, identified or designed using the methods according to embodiments of the present invention, can be designed so that their administration kills the target organisms or inhibits some aspect of the biological functions of the target organisms while failing to have a similar effect on the non-targeted organism. The adverse effects of the agent on the targeted organisms may include, but are not limited to, death of the target organism; slowing growth rates; slowing or eliminating passage from one growth phase to another (e.g., extending the larval growth stage); slowing or eliminating reproduction, decreasing or preventing mating, decreasing or eliminating offspring production, limiting or eliminating target organism weight gains; decreasing or eliminating feeding ability and behaviors; and disrupting cellular, tissue and/or organ functions.

The novel ligands contemplated according to some embodiments of the present invention can be useful as antimicrobial agents (e.g., antifungals, antibacterials, antiprotozoals, etc.) to target specific organisms. For example, the novel ligands can target animal, prokaryotic organisms (pathogenic bacteria), and eukaryotic multicellular pests.

Antimicrobial agents that inhibit protein synthesis by interacting with ribosomes are known to the skilled artisan. A few examples are discussed below. These known agents can be modified to obtain novel agents by using computer modeling techniques and knowledge of the structure of ribosomes and ribosomal subunits and the structure of ribosome/agent and ribosomal subunit/agent complexes, such as the native and complex structures of large ribosomal subunits of a pathogenic bacteria provided herein, such as the SA50S.

The design of ligands of ribosomes or ribosomal subunits according to embodiments of the present invention generally involves consideration of two factors: the ligand is to be capable of physically and structurally associating with the large ribosomal subunit, while considering non-covalent molecular interactions which are present in the association of ribosomes and ribosomal subunits with the ligand, including electrostatic interactions, hydrogen bonding, van der Waals and hydrophobic interactions; and the ligand is to be able to assume a conformation that allows it to associate with the ribosomes or ribosomal subunits, more preferably to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, and more preferably with the SA50S ribosomal subunit. Although certain portions of the molecule may not directly participate in this association with a ribosome or ribosomal subunits those portions may still influence the overall conformation of the molecule. This, in turn, may have an impact on binding affinities, therapeutic efficacy, drug-like qualities, and potency. Such conformational requirements include the overall three-dimensional structure and orientation of the ligand in relation to all or a portion of the binding site or other region of the ribosomes or ribosomal subunits, or the spacing between functional groups of a ligand comprising several functional groups that directly interact with the ribosomes or ribosomal subunits, more preferably to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, and more preferably with the SA50S ribosomal subunit.

The putative calculated inhibitory or binding effect of a ligand on ribosomes and ribosomal subunits may be analyzed prior to its actual synthesis and testing by the use of computer modeling techniques. If the theoretical structure of the given ligand suggests insufficient interaction and association between it and ribosomes or ribosomal subunits, synthesis and testing of the ligand is obviated. However, if computer modeling indicates a strong interaction, the ligand may then be synthesized and tested for its ability to interact with the ribosomes or ribosomal subunits and inhibit protein synthesis. In this manner, synthesis of inoperative ligands may be avoided. In some cases, inactive ligands are synthesized, predicted on modeling and then tested to develop a SAR (structure-activity relationship) for ligands interacting with a specific region of the ribosome or ribosomal subunit, more preferably to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, and more preferably of the SA50S ribosomal subunit. As used herein, the term "SAR", shall collectively refer to the structure-activity/structure property relationships pertaining to the relationship(s) between a ligand's activity/properties and its chemical structure.

One skilled in the art may use one of several methods to identify chemical moieties or entities, ligands, or other agents for their ability to associate with a preselected target site within a ribosomes or ribosomal subunit. This process may begin by visual inspection or computer assisted modeling of, for example, the target site on the computer screen based on the atomic coordinates of the SA50S ribosomal subunit and/or its complexes with other analogues and antibacterial agents. In some of the respective embodiments of the present invention, ligand design uses computer modeling programs which calculate how different ligands interact with the various binding sites of the ribosome, ribosomal subunit, or a fragment thereof. Selected chemical moieties or entities, ligands, or agents may then be positioned in a variety of orientations, or docked, within at least a portion of the binding site of a ribosome or ribosomal subunit, more preferably to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, and more preferably of a SA50S ribosomal subunit. Databases of chemical structures are available from, for example, Cambridge Crystallographic Data Center (Cambridge, U.K.) and Chemical Abstracts Service (Columbus, Ohio). Docking may be accomplished using software such as Quanta and Sybyl, followed by energy minimization and molecular dynamics with standard molecular mechanics forcefields, such as CHARMM and AMBER.

According to some embodiments of the present invention, the affinity of a designed ligand may be increased, compared to, for example, a template ligand, by designing a ligand so as to exhibit more functional groups and moieties on its molecular surface, compared to the template ligand, which compliment and thus interact with counter functional groups on the molecular surface in or near a specific ribofunctional locus in the target ribosome; in other words, a ligand which exhibits a pharmacophore which better compliments the ribofunctional locus of interest in the target ribosome.

The specificity of the ligand towards a particular species is afforded by designing a ligand having functional groups and moieties that match counter functional groups in the ribosome of a target species that are specific to that ribosome, namely the ligand is designed based on structural differences between ribosomes of different species. Species-specific structural information is provided, for example, by the SA50S native and complex structures provided and described herein, which is used to identify the SA-specific pharmacophores which are the most diverse compared to equivalent pharmacophores which bind, for example, to a host's ribosome.

As an alternative approach to the de novo structure-based drug design approach, it is contemplated that pre-existing (pre-verified) ligands of the target pathogenic ribosome or ribosomal subunit may be used as a structural starting point (template) for the design of a novel ligand. It is contemplated that knowledge of the spatial relationship between a pre-verified ligand, such as a known protein biosynthesis inhibitor, and its respective binding site within a ribosome (its ribofunctional locus) of a target pathogen is conducive to the identification of a more elaborate pharmacophore, and to the design of a modified ligand that may have improved binding properties, for example, higher binding affinity and/or higher species specificity, relative to the original (template) ligand it has been derived from. Alternatively, structural knowledge of more than one pre-verified ligands and their respective ribofunctional loci in the ribosome or ribosomal subunit of the target pathogenic microorganism is conducive to the design of a novel ligand that contains, for example, a portion of each of the pre-verified ligands. Such a ligand is referred to herein as adduct or conjugate.

The positioning data of each pre-verified ligand relative to the large ribosomal subunit of a pathogenic bacterium, such as the SA50S provided herein, provides information on what portions of the ribosome or ribosomal subunit and what portions the ligand are in contact. Accordingly, using this structural information obtained experimentally, the skilled artisan can identify ribofunctional loci that can be used for de novo drug design, as discussed above, as well as identify portions of a ligand that can act as a ribosome binding moieties.

Based on the structural information pertaining to a large ribosomal subunit of a pathogenic bacterium, such as the SA50S provided herein, the skilled artisan may readily identify a more elaborate pharmacophore and design novel adduct ligands that comprise a ribosome binding moiety of a first pre-existing ligand or an analogue or a derivative thereof and a ribosome binding moiety of a second, different pre-existing ligand or an analogue or a derivative thereof, each expanding the pharmacophore of the other. As stated hereinabove, in some of any of the respective embodiments of the present invention, a pre-existing ligand used as templates for the expansion of the known pharmacophore and to the design of a novel adduct ligand, may refer to a pre-verified antibacterial agent. The resulting novel designed adduct ligand, according to embodiments of the present invention, preferably binds simultaneously to each of the respective ribofunctional loci within the ribosomal subunit by exhibiting a more elaborate pharmacophore, and thus exhibits higher binding affinity and/or higher specificity to the ribosomal subunit compared to the affinity and/or specificity exhibited by the two template antibacterial agents individually, and even exhibit synergistic binding properties compared to those of the two individual template antibacterial agents.

It is noted herein that embodiments of the present invention are meant to encompass design of novel ligands based on combining the pharmacophores of more than two, more than three and more than four pre-existing ligands; namely the expansion of the known pharmacophore is effected by obtaining complex structures of a ribosome or a ribosomal subunit with more than two different pre-existing ligands bound thereto, and the resulting novel ligand may share moieties (pharmacophore elements) stemming from more than two pre-existing ligands. In general, any number of complex structures of a ribosomal subunit bound to a pre-existing ligand can be used as a training set for the procedure of identification and expansion of a pharmacophore pertaining to any given ribofunctional locus, wherein the training set is the collection of ligands bound in a given binding site or near it, which can be superimposed on one-another based on common target's atoms positions.

The positioning data of the exemplary SA50S provided herein, native and/or complexes thereof with pre-verified antibacterial agents, allow the skilled artisan to identify putative antibacterial agents that may be used as templates in the synthesis of novel adducts, and also provide structural information necessary to produce linking moieties such that each ribosome binding moiety in the adduct is properly positioned and orientated relative to its respective binding site. As a result, it is contemplated that the skilled artisan may produce adduct ligands (adduct antibacterial agents) that bind to a SA ribosome or ribosomal subunit with a higher affinity and specificity, and/or exhibit higher ribofunctional inhibitory activity than either of the individual template antibacterial agents used to design the adduct. Alternatively, the conjugate (adduct antibacterial agent) may overcome resistance phenotypes that may have developed against either of the template antibiotics.

As used herein, the phrase "linking moiety" describes a chemical moiety that links two other chemical moieties via one or more covalent bonds, hence linking therebetween. In general, the linking moiety can be formed during a chemical reaction, such that by reacting two or more reactive groups, the linking moiety is formed as a new chemical entity which can comprise a bond (between two atoms), or one or more bonded atoms. Alternatively, the linking moiety can be an independent chemical moiety comprising two or more reactive groups to which compatible reactive groups on other compounds can be attached, either directly or indirectly. In the context of the present embodiments, the linking moiety can be, for a non-limiting example, a single, double or triple covalent bond; a heteroatom (such as, but not limited to, O, N, S, and P); and a saturated or unsaturated, aliphatic or aromatic, substituted or unsubstituted hydrocarbon chain having 1-6 carbon atoms, optionally interrupted by 1-6 heteroatoms.

For example, the proximity of a site occupied by the hydroxyl group of the tricyclic mutilin core of BC-3205 to the site occupied by the desosamine sugar of telithromycin and the proximity of a site occupied by the valyl moiety $NH_2$ of BC-3205 to the site occupied by the alkyl-aryl arm of telithromycin suggests that adducts comprising the aforementioned hydroxyl portion of both BC-3205 and the desosamine sugar portion of the telithromycin, spaced and positioned relative to one-another as they are seen in the crystal structure of the corresponding complex, may be an effective inhibitor of protein synthesis of the exemplary SA50S.

Furthermore, the positioning data of the SA50S provided herein, native and complexes, allow the skilled artisan to use the information pertaining to identify ribosome binding moieties and design other types of ribofunctional inhibitors, also for large ribosomal subunit of other pathogenic bacteria. For example, with an understanding of the ribosome contact region and the surrounding environment, and the identification of species-specific variations in the ribosome structure, the skilled artisan can design novel ligands, a portion of which is based upon the antibiotic binding site and another portion of which can be designed as a novel site that sterically inhibits or disrupts protein biosynthesis within the ribosome or secretion through the polypeptide exit tunnel. For example, the skilled artisan may combine the ribosome binding site of pre-verified antibacterial agent or an analog or derivative thereof, which binds to one side of the polypeptide exit tunnel close to the peptidyl transferase site, with, for example, a novel chemical moiety which is not present in antibacterial agent, and which is identified based on the structure of the SA50S, that can effectively block the polypeptide exit tunnel. Furthermore, it is contemplated that the skilled artisan may take advantage of one or more of the many of the antibiotic binding sites known in the art, and those that can be elucidated based on the provisions disclosed herein to design entirely new binding moieties.

According to some embodiments of the present invention, the skilled artisan can design ribofunctional ligands, for example, selective protein synthesis inhibitors, that are tailored to be more potent with respect to ribosomes of a target pathogenic organism, such as SA, and less potent, i.e., less toxic, to ribosomes of a non-target organism, for example, a host organism such as a human. The presently provided positioning data of the SA50S, native and complexes thereof with pre-verified ligands, allow the skilled artisan to design modifications to lead compounds, such as an antibacterial agent, that will bind more tightly to the SA50S ribosomal subunit and less tightly to a non-targeted ribosome, e.g., human 60S ribosomal subunit or a human mitochondrial ribosome. The positioning data provided herein can also be used to guide the modification of pre-verified ligand to produce new ligands that have other desirable properties for the applicable industrial and other uses (e.g., as pharmaceuticals), such as chemical stability, solubility or membrane permeability.

A variety of pre-verified ligands of the large ribosomal subunit that disrupt protein synthesis include, without limitation, chloramphenicols, macrolides, lincosamides, streptogramins, althiomycins, oxazolidinones, nucleotide analogs, thiostreptons (including microccocin family), peptides, glutarimides, trichothecenes, TAN-1057, pleuromutilins, hygromycins, betacins, eveminomicins, boxazomycins, and fusidanes.

Members of the chloramphenicol family include, for example, Chloramphenicol and Iodoamphenicol. Members of the macrolide family include, for example, Biaxin (Clarithromycin), Zithromax (Azithromycin; azalide), Ketek (Telithromycin; ketolide), ABT-773, Tylosin, Spiramycin I, Spiramycin II, Spiramycin III, Erythromycin A, Carbomycin A, Telithromycin, Methymycin, Narbomycin, Lankamycin, Oleandomycin, Megalomycin, Chalcomycin, Niddamycin, Leucomycin, Angolamycin, Picromycin, and Relomycin. Members of the licosamide family include, for example, Clindamycin and Lincomycin. Members of the streptogramin family include, for example, Streptogramin A, Streptogramin B, Ostreogrycin G, Synercid, Virginiamycin S1, Virginiamycin S2, Virginiamycin S3, Virginiamycin S4, Vernamycin B, Vernamycin C, Patricin A, and Patricin B. A member of the althiomycin family includes, for example, Althiomycin. Members of the oxazolidinone family, include, for example, Linezolid, Eperezolid, and DuP721. Members of the family of nucleotide analogs include, for example, Sparsomycin, Puromycin, Anisomycin, and Blasticidin S. Members of the thiostrepton family include, for example, Thiostrepton, Siomycin, Sporangiomycin, Microccocin M1, Microccocin P, and Thiopeptin. Members of the peptide family include, for example, Viomycin, Capreomycin IA, Capreomycin IB, Capreomycin IIA, and Capreomycin IIB. Members of the glutarimide family include, for example, Cycloheximide, Streptovitacins, Streptimidone, Inactone, Actiphenol. Members of the trichothecene family include, for example, Trichodermin, Trichodermol, Trichodermone, Vomitoxin, T-2 toxin, Trichothecin, Nivalenol, and Verrucarin A. Tan-1057 includes Tan-1057A, Tan-1057B, Tan-1057C, and Tan-1057D. Pleuromutilins include, for example, Pleuromutilin, Tiamulin, Azamilin, and Valnemulin. Hygromycins includes the Hygromycin A antibiotics. Betacins include, for example, the family of betacin natural products and VCR4219. Everninomicins include, for example, Ziracin, Avilamycin, Evernimicin, and Curamicin. Boxazomycins include, for example, Boxazomycin A and B. Fusidanes include, for example, fusidic acid and 175, 20S-dihydrofusidic acid diethylene glycol hydrate.

Once a putative ligand has been designed or selected by the above methods, the affinity with which that ligand binds to the ribosome or ribosomal subunit may be tested and optimized by computational evaluation and/or by testing biological activity after synthesizing the compound and contacting the same with the ribosome or ribosomal subunit of choice. Putative ligands may interact with the ribosomes or ribosomal subunits in more than one conformation, each of which has a similar overall binding energy. In those cases, the deformation energy of binding may be considered to be the difference between the energy of the free molecule and the average energy of the conformations observed when the ligand binds to the ribosomes or ribosomal subunits, or to the large ribosomal subunits, or to the 50S ribosomal subunits of various pathogenic bacteria, or to large ribosomal subunits of pathogenic bacterium excluding *Escherichia coli*, a pathogenic Gram positive bacterium, or a pathogenic bacterium exhibiting a degree of 23S rRNA sequence identity of at least 80% compared to the 23S rRNA of *Staphylococcus aureus*, or to the SA50S ribosomal subunit.

A ligand designed or selected as binding to a ribosome or ribosomal subunit may be further computationally optimized so that in its bound state it preferably lacks repulsive electrostatic interaction with the target region. Such non-complementary (e.g., electrostatic) interactions include repulsive charge-charge, dipole-dipole and charge-dipole interactions. Specifically, the sum of all electrostatic interactions between the ligand and the molecular surface of its binding site when the ligand is bound to the ribosome or the ribosomal subunit, preferably makes a neutral or favorable contribution to the enthalpy of binding. Weak binding ligands can also be designed by these methods so as to provide SAR information.

Specific computer programs that can evaluate a ligand deformation energy and electrostatic interaction are available in the art. Examples of suitable programs include, without limitation, Gaussian 92, revision C (M. J. Frisch, Gaussian, Inc., Pittsburgh, Pa.); AMBER, version 4.0 (P. A. Kollman, University of California at San Francisco, Calif.); QUANTA/CHARMM (Molecular Simulations, Inc., Burlington, Mass.); OPLS-AA ("OPLS Force Fields." W. L. Jorgensen. Encyclopedia of Computational Chemistry, Schleyer, Ed.; Wiley: New York, 1998; Vol. 3, pp 1986-1989.) and Insight II/Discover (Biosym Technologies Inc., San Diego, Calif.). These programs may be implemented, for instance, using a Silicon Graphics workstation, IRIS 4D/35 or IBM RISC/6000 workstation model 550. Other suitable computer systems and software packages are known to those skilled in the art.

Once a ligand has been selected or designed, as described above, substitutions may then be made in some of its atoms or side groups in order to improve or modify its binding properties. Generally, initial substitutions are conservative, i.e., the replacement group will approximate the same size, shape, hydrophobicity and charge as the original group. It is to be understood that components known in the art to alter conformation and non-feasible chemical structures should be avoided. Such substituted ligands may then be analyzed for efficiency of fit to the ribosome or ribosomal subunit by the same computer methods described herein.

The designed ligand can be prepared by chemical procedures known in the art, and can further be prepared according to a computer-assisted organic synthesis (CAOS) program. CAOS programs are used in organic chemistry and computational chemistry to facilitate the task of reactions design and prediction. A CAOS program can take into synthesis considerations the spatial limitations and constrains stemming from the structure-based drug design process so as to suggest a synthetic procedure that can afford a viable and chemically feasible ligand. A typical CAOS program identifies a sequence of chemical reactions capable of producing a desired target molecule. CAOS algorithms typically utilize a database of known chemical reactions and a second database of known starting materials (i.e., typically commercially available molecules). Preferred synthetic plans and procedures are selected according to cost considerations, expected yield, and avoidance of hazardous reactants, reactions and intermediates. Exemplary CAOS programs and software packages that can be used in the context of embodiments of the present invention include, without limitation, WODCA, OSET, CHIRON, SynGen, LHASA, SYLVIA and ARChem.

In addition, the putative ribosome ligands, complexes or mimetics thereof may be co-crystallized with ribosomes or their subunits and analyzed using X-ray diffraction. The diffraction data are similarly used to calculate the three-dimensional interaction of a putative ligand and the ribosome, ribosomal subunit, or a mimetic, in order to confirm that the ligand binds to, or changes the conformation of, a particular binding site on the ribosome or ribosomal subunit, or where the mimetic has a similar three-dimensional structure to that of a ribosome, ribosomal subunit or a fragment thereof.

A High-Affinity/High-Specificity Ligand:

Embodiments of the present invention provides the use of molecular and computer modeling techniques to design and select novel ligands of ribosomal particles, such as antibacterial agents or other therapeutic agents, that interact with ribosomes and ribosomal subunits. Such antibiotics and other types of therapeutic agents include, but are not limited to, antifungals, antivirals, antibacterials and the likes. It is noted that the novel ligand, according to embodiments of the present invention, is designed to be structurally different from all known and/or naturally occurring ligands, and further designed to exhibit improved binding properties (affinity and specificity) compared to known and/or naturally occurring ligands. Hence, previously known ligands of the ribosome of pathogenic bacteria, including all previously known naturally occurring and/or synthetic antibiotics, polypeptides, nucleic acids and the likes, are excluded from the scope of the present invention in the context of some embodiments thereof pertaining to de-novo designed ligands of the ribosome of the pathogenic bacteria.

It will be appreciated that due to the tight correlation between structure and activity of biological molecular systems, and the tight correlation between biological molecular target structure and the specificity and affinity of a given ligand, knowledge of the intricate relations between the ribosomal subunit of one species and its corresponding ligands can serve for insights for designing ligands that will be active (exhibit high affinity and specificity) with respect to corresponding ribosomal subunit of various phylogenetically/evolutionary/genealogically related species, as this concept is defined herein.

As described hereinabove, a ligand can be designed to exhibit an affinity to a molecular surface of at least one binding site or a ribofunctional locus of a ribosomal subunit of a pathogenic bacterium, a pathogenic Gram positive bacterium, or a pathogenic bacterium exhibiting a degree of 23S rRNA sequence identity of at least 80% compared to the 23S rRNA of *Staphylococcus aureus*, such as the SA50S provided herein.

According to an aspect of some embodiments of the present invention, there is provided a ligand having an affinity to a molecular surface of at least a portion of a binding site or a ribofunctional locus of a large ribosomal subunit of a pathogenic bacterium provided herein, designed by the method provided herein.

The general concept of the rational/structure-based drug design paradigm is based on the availability of several experimental crystal structures of the target entity, namely the pathogen's protein synthesis machinery, embodied by the bacterial ribosome or subunits thereof, having a known and pre-verified ligands thereof bound thereto. The paradigm includes the identification and recordation of the pharmacophore associated with each of the pre-verified ligands, and in particular the interaction of functional groups in the active-site with moieties in each of the pre-verified ligands. According to some embodiments, the de-novo ligand presented herein is designed as adduct (a conjugate) of two or more molecular entities or moiety, each representing, mimicking or duplicating a moiety in a pre-existing antibacterial agent which has been pre-verified by in-vitro and/or in-vivo bioactivity assays. In such embodiments the possession of positioning data of the SA50S subunit (i.e., the molecular target) allows the design of the adduct such that one moiety is attached to the other moiety so as to permit all moieties to bind with its respective ribofunctional locus, preferably simultaneously, thereby providing a highly effective and species-specific antibacterial agent that disrupts protein synthesis in the target ribosomal subunit.

Non-limiting examples of pre-existing antibacterial agents include linezolid, BC-3205 and telithromycin.

The resulting designed ligand, according to some embodiments of the present invention, has a molecular weight no greater than about 1,500 grams/mol, no greater than about 1,000 grams/mol, no greater than 750 grams/mol or no greater than about 500 grams/mol. The designed ligand preferably has a molecular weight in the range from about 250 grams/mol to about 1500 grams/mol, or in the range from about 500 grams/mol to about 1200 grams/mol.

According to some embodiments, the affinity of the ligand to the ribosomal subunit can be characterized by the association/dissociation constant (interchangeably referred to herein as an affinity constant, a binding constant or $k_D$) of the ligand to the ribosomal subunit, as detectable by a binding assay. According to some embodiment of the present invention the binding affinity is high and considered "specific" if it occurs with a $k_D$ of 1 mM or less, generally in the range of 500 μM to 10 pM.

According to some embodiments of the present invention, the designed ligand has a minimal inhibitor concentration lower than 50 μM, lower than 10 μM, or lower than 1 μM, required for inhibiting 50 percent activity ($IC_{50}$) in a biological assay, for example, an in vitro translation assay, for example, an SA translation assay. The designed ligand has an $IC_{50}$ in the range of from about 0.001 µM to about 50 µM, or in the range of from about 0.01 µM to about 10 µM, or in the range of from about 0.1 µM to about 1 µM.

In some of any of the respective embodiments of the invention, a substantially rigid ligand is designed, such that the ligand have relatively small number of conformations it can take by virtue of having a relatively small number of rotatable bonds. It should be appreciated that absolutely rigid molecules are generally not feasible, hence the term "substantially rigid" is used. Without being bound by any particular theory, it is assumed that as the structure of a given molecule is characterized by a higher degree of freedom and the less rigid the molecule is, the harder it is for the molecule to bind to a receptor and the less tight is its binding. However, less rigid molecules with some degree of conformational freedom are contemplated, taking into account design and/or synthetic and/or pharmaceutical considerations, as well as other practical reasons.

In some of any of the respective embodiments of the present invention, the ligand is a pathogenic bacterium-specific protein synthesis inhibitor; in some of the embodiments, the ligand is a protein synthesis inhibitor of a Gram positive cocci bacterium; in some of the embodiments, the ligand is a protein synthesis inhibitor of a *Staphylococcus* bacterium; in some of the respective embodiments, the ligand is a protein synthesis inhibitor of *Streptococcus pneumoniae*; in some of the respective embodiments, the ligand is a protein synthesis inhibitor of *Bacillus subtilis*; in some of the respective embodiments, the ligand is a protein synthesis inhibitor of *Clostridium difficile*; and in some of the respective embodiments, the ligand is a protein synthesis inhibitor of *Staphylococcus aureus*.

It is noted that the novel designed ligand for a ribosomal subunit of a pathogenic microorganism is not a naturally occurring ligand, such as a peptide, a protein or an aminoglycoside, but it may exhibit some chemical elements (moieties) which are similar or mimic moieties of some naturally occurring chemical entities or ligands. For example, while the novel ligand is not a peptide, it made comprise one or more peptide (amide) binds, one or more amino acids bound by a peptide bond and the likes, however the ligand comprises other chemical moieties that render it clearly distinguishable from any naturally occurring peptide that may serve as a naturally occurring ligand to the target ribosome.

A Method of Treating an Infection:

Treatment includes abscess drainage, debridement of necrotic tissue, removal of foreign bodies (including intravascular catheters), and use of antibacterial agents. Antibacterial agents are typically selected based on severity of the infection and local resistance patterns. Initial choice and dosage of antibiotics depend on infection site, illness severity, and probability that resistant strains are involved. Thus, it is useful to acquire information pertaining to local resistance patterns for initial therapy, and ultimately, to monitor actual drug susceptibility.

Treatment of toxin-medicated staphylococcal disease (disease caused by Gram positive pathogenic bacterium such as Gram positive cocci bacterium), most serious of which is toxic shock syndrome, involves: decontamination of the toxin-producing area by exploration of surgical wounds, irrigation and debridement; intensive support by IV fluids, vasopressors and respiratory assistance; electrolyte balancing; and the use of antimicrobial agents. In vitro evidence supports a preference for protein synthesis inhibitors over other classes of antibiotics.

It is noted that many staphylococcal strains produce penicillinase, an enzyme that inactivates several β-lactam antibiotics; these strains are resistant to penicillin G, ampicillin and antipseudomonal penicillins. Community-acquired strains are often susceptible to penicillinase-resistant penicillins, such as methicillin, oxacillin, nafcillin, cloxacillin, dicloxacillin, cephalosporins, carbapenems, imipenem, meropenem, ertapenem, doripenem, macrolides, fluoroquinolones, trimethoprim/sulfamethoxazole (TMP/SMX), gentamicin, vancomycin and teicoplanin.

MRSA isolates have become common, especially in hospitals. These resistant strains, although resistant to most β-lactams, are usually susceptible to TMP/SMX, doxycycline, or minocycline and are often susceptible to clindamycin, but there is the potential for emergence of clindamycin resistance by strains inducibly resistant to erythromycin. Vancomycin is effective against most MRSA, sometimes with rifampin and an aminoglycoside added for serious infections. Some alternative drugs such as daptomycin, linezolid, quinupristin/dalfopristin, TMP-SMX and ceftaroline, may be considered when treating MRSA strains with a vancomycin.

Vancomycin-resistant *S. aureus* (VRSA) and vancomycin-intermediate-susceptible *S. aureus* (VISA) strains have appeared in the North America. Control over these organisms requires the use of linezolid, quinupristin/dalfopristin, daptomycin, TMP/SMX or ceftaroline.

Because incidence of resistant SA strains has increased, initial empiric treatment for serious staphylococcal infections, particularly those that occur in a health care setting, typically include a drug with reliable activity against MRSA. Thus, for proven or suspected bloodstream infections, vancomycin or daptomycin are typically used. For pneumonia, vancomycin or linezolid are used because daptomycin is not reliably active in the lungs.

It is noted that all of the above known methods of treatment are limited in their efficacy due to growing rate of resistance immergence among pathogenic strains of bacteria, and the presently provided ribosomal 50S subunit ligands offer a comprehensive solution to the problems associated with the treatments against such pathogenic strains by virtue of being a genus of rationally designed ligands that have been designed based on the structural information afforded by the presently disclosed crystal structure of the native and AB-complex SA50S exemplary structures.

The resulting ligands can be useful in treating, inhibiting or preventing the biological activities of target organisms, thereby killing the organism or impeding its growth. Alternatively, the resulting molecules can be useful for treating, inhibiting or preventing microbial, e.g., bacterial, infections in any organism, particularly animals, more particularly humans.

According to an aspect of some embodiments of the present invention, there is provided a method of treating an infection associated with a pathogenic bacterium. The method is effected by administering to a subject in need thereof a therapeutically effective amount of the ligand presented herein.

In some of any of the embodiments of the present invention, the pathogenic bacterium is a pathogenic Gram positive bacterium, or a pathogenic bacterium exhibiting a degree of 23S rRNA sequence identity of at least 80% compared to the 23S rRNA of *Staphylococcus aureus*; in some of the respective embodiments, the pathogenic bacterium is a Gram positive cocci bacterium; in some of the respective embodiments, the pathogenic bacterium is a *Staphylococcus* bacterium; in some of the respective embodiments, the pathogenic bacterium is *Streptococcus pneumoniae*; in some of the respective embodiments, the pathogenic bacterium is *Bacillus subtilis*; in some of the respective embodiments, the pathogenic bacterium is *Clostridium difficile*; and in some of the respective embodiments, the pathogenic bacterium is *Staphylococcus aureus*.

According to some of any of the respective embodiments of the present invention, the pathogenic bacterium is a Gram positive cocci bacterium, a *Staphylococcus* bacterium or *Staphylococcus aureus*, and in some of the embodiments the *Staphylococcus aureus* is a drug-resistant strain thereof.

According to some embodiments, the ligand is administered alone or in combination with one or more other antibacterial agents.

According to some embodiments, the infection associated with a pathogenic bacterium is a skin infection, which is one of the most common types of disease produced by *Staphylococcus* bacterium (Staph infections). Staph infections of the skin can progress to impetigo (a crusting of the skin) or cellulitis (inflammation of the deeper layers of skin and connective tissue under the skin, leading to swelling and redness of the area). In some cases, a serious complication known as scalded skin syndrome can develop from Staph infections. In breastfeeding women, Staph infections can result in mastitis (inflammation of the breast) or in abscess of the breast. Staphylococcal breast abscesses can release bacteria into the mother's milk.

When the *Staphylococcus* bacteria enter the bloodstream and spread to other organs, a number of infections can occur. Spread of the organisms to the bloodstream is known as bacteremia or sepsis. Staphylococcal pneumonia predominantly affects people with underlying lung disease and can lead to abscess formation within the lungs. Infection of the heart valves (endocarditis) can lead to heart failure. Spread of Staphylococci bacteria to the bones can result in severe inflammation of the bones known as osteomyelitis. When Staphylococci bacteria are present in the blood, a condition known as staphylococcal sepsis (widespread infection of the bloodstream) or staphylococcal bacteremia exists. Staphylococcal sepsis is a leading cause of shock and circulatory collapse, leading to death, in people with severe burns over large areas of the body. When untreated, *S. aureus* sepsis carries a mortality rate of over 80%. *S. aureus* has been reported as a cause of chorioamnionitis and neonatal sepsis in pregnancy, leading to life-threatening condition for the fetus.

Staphylococcal infections are contagious and can be transmitted from person to person.

A Pharmaceutical Composition:

According to an aspect of some embodiments of the present invention, there is provided a pharmaceutical composition which includes as an active ingredient, the ligand of the ribosomal subunit of a pathogenic bacterium, as provided herein.

In some of any of the respective embodiments of the present invention, the pharmaceutical composition is packaged in a packaging material and identified in print, in or on the packaging material, for use in the treatment of an infection associated with a pathogenic bacterium, e.g., *S. aureus* infection.

The active ligand, once identified according to some embodiments of the present invention, may be incorporated into any suitable carrier prior to use. More specifically, the dose of active ligand, mode of administration and use of suitable carrier will depend upon the target and non-target organism of interest.

With regard to mammalian recipients, the active ligand may be administered by any conventional approach known and/or used in the art. Thus, as appropriate, administration can be oral or parenteral, including intravenous and intraperitoneal routes of administration. In addition, administration can be by periodic injections of a bolus, or can be made more continuous by intravenous or intraperitoneal administration from a reservoir which is external (e.g. an intravenous bag). In certain embodiments, the active ligand of the invention can be therapeutic-grade, namely certain embodiments comply with standards of purity and quality control required for administration to humans. Veterinary applications are also within the intended meaning as used herein.

The formulations, both for veterinary and for human medical use, of the active ligand according to the present embodiments, typically include such agents in association with a pharmaceutically acceptable carrier, and optionally other therapeutic ingredient(s). The carrier(s) should be "acceptable" in the sense of being compatible with the other ingredients of the formulations and not deleterious to the recipient thereof. Pharmaceutically acceptable carriers, in this regard, are intended to include any and all solvents, dispersion media, coatings, antibacterial and antifungal agents, isotonic and absorption delaying agents, and the like, compatible with pharmaceutical administration. The use of such media and agents for pharmaceutically active substances is known in the art. Except insofar as any conventional media or agent is incompatible with the active ligand, use thereof in the compositions is contemplated. Supplementary active agents, identified or designed according to the invention and/or known in the art, also can be incorporated into the compositions. The formulations may conveniently be presented in dosage unit form and may be prepared by any of the methods well known in the art of pharmacology/microbiology. In general, some formulations are prepared by bringing the active ligand into association with a liquid carrier or a finely divided solid carrier or both, and then, if necessary, shaping the product into the desired formulation.

Pharmaceutical compositions according to some embodiments of the present invention are formulated to be compatible with its intended route of administration. Examples of routes of administration include oral or parenteral, e.g., intravenous, intradermal, inhalation, transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide.

Useful solutions for oral or parenteral administration can be prepared by any of the methods well known in the pharmaceutical art, described, for example, in Remington's Pharmaceutical Sciences, (Gennaro, A., ed.), Mack Pub., (1990).

Pharmaceutical compositions suitable for injectable use, according to some embodiments of the present invention, include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, N.J.) or phosphate buffered saline (PBS).

The active ligand may be prepared with carriers that will protect the ligand against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials also can be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811. Microsomes and microparticles also can be used.

As noted above, active ligands identified or designed according to embodiments of the present invention can be formulated into pharmaceutical compositions by admixture with pharmaceutically acceptable nontoxic excipients and carriers. Such compositions can be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition can include the active ligand dispersed in a fibrinogen-thrombin composition or other bioadhesive. The active ligand can then be painted, sprayed or otherwise applied to the desired tissue surface. Alternatively, the active ligand can be formulated for parenteral or oral administration to humans or other mammals, for example, in therapeutically effective amounts, e.g., amounts which provide appropriate concentrations of the active ligand to target tissue for a time sufficient to induce the desired effect.

Active ligands identified or designed by any of the methods provided herein may also come in a form of precursors of the active ligands. The term "precursor" refers to a pharmacologically inactive (or partially inactive) derivative of a parent ligand that requires biotransformation, either spontaneous or enzymatic, within the organism to release the active ligands. Precursors are variations or derivatives of the ligands of the invention which have groups cleavable under metabolic conditions. Precursors become the active ligands of the invention which are pharmaceutically active in vivo, when they undergo solvolysis under physiological conditions or undergo enzymatic degradation. Precursor forms often offer advantages of solubility, tissue compatibility, or delayed release in the mammalian organism (see Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992).

Active ligands as identified or designed by any of the methods described herein can be administered to individuals to treat disorders (prophylactically or therapeutically). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a drug as well as tailoring the dosage and/or therapeutic regimen of treatment with the drug.

With regard to mammals, it is contemplated that the effective dose of a ligand that serves as a protein synthesis inducer or inhibitor, will be in the range of about 0.01 to about 50 mg/kg, preferably about 0.1 to about 10 mg/kg of body weight, administered in single or multiple doses. Typically, the ligand may be administered to a human recipient in need of treatment at a daily dose range of about 1 to about 2000 mg per patient.

It is expected that during the life of a patent maturing from this application additional relevant structures of large ribosomal subunit of pathogenic bacteria and SA50S-specific ligands will be developed and the scope of the terms SA50S structures and SA50S-specific ligands is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

Preparation of 50S Subunit Sample from SA

SA Growth and Cell Wall Disruption:
Following Iordanescu and Surdeanu [*Journal of General Microbiology*, 1976, 96(2), p. 277-81] *Staphylococcus aureus* (SA) strain RN4220 (ATCC 35556) was grown overnight at 37° C., and cells were harvested at $OD_{600nm}$ of about 1.5. The bacterial culture was centrifuged twice in a table top centrifuge for 10 minutes at 4000 rpm at 4° C. The supernatants were discarded and the wet cell pellets were weighed, resuspended in 10 mM Tris-Acetate buffer, pH=8.0, 14 mM Mg-Acetate, 1 M KCl, 1 mM DTT and 50 µg/ml lysostaphin (glycylglycine endopeptidase that breaks down the cell wall Staphylococci species), incubated at 37° C. for 1 hour and periodically inverted.

The lysates were centrifuged for 30 minutes at 36,000 rpm, at 4° C. for removing cell debris. The supernatants were incubated in 670 mM Tris-Acetate buffer pH=8.0, 20 mM Mg-Acetate, 7 mM DTT, 7 mM $Na_3$-phosphoenolpyruvate, 5.5 mM ATP, 70 mM from each amino acid and 1.9 mg Pyruvatkinase at 37° C. for 30 minutes and dialyzed overnight at 4° C. against dialysis 10 mM Tris-Acetate buffer pH=8.0, 14 mM Mg-Acetate, 60 mM K-Acetate and 1 mM DTT.

The extract was then flash-frozen and stored at −80° C.

Purification of SA Ribosomes:
Cell extract was layered on a sucrose cushion (Selmer et al., 2006) 1.1 M sucrose, 10 mM Hepes (pH=8.0, pH was set according to the pH of the cell extract), 15 mM $MgCl_2$, 100 mM $NH_4Cl$, 50 mM KCl, 6 mM β-mercaptoethanol, and ultracentrifuged twice, each time for 17 hrs at 4° C. at 55 Krpm using a Ti-70 rotor. The supernatant was then discarded; the pellet was dissolved in 10 mM Hepes, 15 mM $MgCl_2$, 150 mM $NH_4Cl$, 50 mM KCl and 6 mM β-mercaptoethanol buffer set at pH=8.0. Ribosomal subunits were then separated by zonal ultracentrifugation, using a Ti-15 zonal rotor with a gradient of 8-40% sucrose, keeping low $Mg^{2+}$ concentration (1 mM $MgCl_2$) for 17.5 hours at 27K rpm. After separation, the $Mg^{2+}$ concentration was increased to 10 mM and the ribosomal subunits fractions were collected and concentrated using sequential centrifugations. The samples were kept at 10 mM Hepes buffer, 10 mM $MgCl_2$, 60 mM $NH_4Cl$ and 15 mM KCl buffer set at pH=7.6, and brought to a final concentration of 600-1000 or 800-1000 $A_{260}$ $ml^{-1}$, then were flash-frozen for storage at −80° C.

Ribosome Activity Assay:
The SA ribosomes activity was tested and its level was determined in a bacterial coupled transcription/translation assay system which measures the expression of the luciferase gene, according to Murray, R. W. et al. [*Antimicrobial agents and chemotherapy*, 2001, 45(6), p. 1900-1904]. Briefly, the luciferase gene was inserted into plasmid with T7 RNA polymerase promoter. The 30 µl reaction's volume contained 160 mM Hepes-KOH buffer (pH 7.5), 6.5% PEG 8K, 0.074 mg/ml tyrosine, 1.3 mM ATP, 0.86 mM CTP, GTP and UTP, 208 mM potassium glutamate, 83 mM creatine phosphate, 28 mM $NH_4OAc$, 0.663 mM cAMP, 1.8 mM DTT, 0.036 mg/ml folinic acid, 0.174 mg/ml *E. coli* tRNA mix, 1 mM amino acid, 0.25 mg/ml creatine kinase, 0.027 mg/ml T7 RNA polymerase, ribosome free *E. coli* cell free extract, 300 nM of SA ribosomes and 0.003 µg/µl luciferase plasmid.

The reaction mixture was incubated at 37° C. for 1 hour, and erythromycin was added at a final concentration of 8 µM in order to terminate the reaction. 50 µl of Luciferin Assay Reagent (LAR, Promega) was added to the mixture and luminescence was measured in order to quantify the reaction's products.

Example 2

Crystallization of 50S Subunit from SA

Native SA50S Crystals:
Crystals of the 50S ribosomal subunit extracted from *Staphylococcus aureus* (SA50S) were obtained at 20° C. by the hanging-drop vapor diffusion technique. The crystallization solution contained 0.166% 2-methyl-2,4-pentanediol (MPD), 0.333% EtOH, 20 mM Hepes, 10 mM $MgCl_2$, 60 mM $NH_4Cl$ and 15 mM KCl buffer set to pH range of 6.8-7.8, 5 mM spermidine, 0.5 mM $MnCl_2$ and 1-1.6 mg/ml SA50S. The reservoir solution contained 15% of 1:2 ethanol-MPD and 110 mM Hepes, 10 mM $MgCl_2$, 60 mM $NH_4Cl$ and 15 mM KCl buffer. The SA50S subunits were heat activated for 30 minutes at 37° C. before crystallization. These conditions usually yield about 60-300 µm hexagonal crystals, which appeared as hexagons. High resolution diffracting crystals were obtained by macro seeding, using crystals that were extracted from the crystallization drop, washed in 10 μl of 7.5% EtOH, 7.5% MPD, 110 mM Hepes, 10 mM MgCl$_2$, 60 mM NH$_4$Cl and 15 mM KCl buffer and 0.5 mM MnCl$_2$, and seeded in a crystallization drop as described hereinabove, pre-equilibrated for 24 hours.

SA50S crystals were kept in a stabilization solution containing 15% MPD, 15% EtOH, 110 mM Hepes, 10 mM MgCl$_2$, 60 mM NH$_4$Cl and 15 mM KCl buffer set to pH range of 6.8-7.8) and 0.5 mM MnCl$_2$.

Crystals of SA50S Complexes:

For obtaining SA50S antibiotics complexes, SA50S crystals obtained as described hereinabove were soaked in solutions containing 6 μg/ml linezolid, 11.4-22.7 μg/ml BC-3205, or 16.2 μg/ml telithromycin in the stabilization solution for 3-6 hours prior to exposure to X-ray and data collection.

Example 3

Crystal Structure of 50s Subunit from SA

Data Collection and Processing:

Prior to exposure to X-ray, the crystals were immersed in a cryoprotectant solution containing 20% MPD, 15% EtOH, 110 mM Hepes, 10 mM MgCl$_2$, 60 mM NH$_4$Cl and 15 mM KCl buffer and 0.5 mM MnCl$_2$. Crystallographic X-ray diffraction data were collected at the ID23-1, ID23-2 and ID-29 beamlines, at the European Synchrotron Radiation Facility (ESRF), Grenoble, France, from the hexagonal crystals at a temperature of 100° K. Up to 15 SA50S crystals were used for yielding a complete dataset using 0.1 degree oscillations. Data were processed with HKL-2000 [Otwinowski, Z. and Minor, W., *Methods in Enzymology, Macromolecular Crystallography, part A*, 1997, 276, p. 307-326, Carter, C. W. Jr. and Sweet, R. M., Eds., Academic Press (New York)] and CCP4 package suite [Winn, M. D. et al., *Acta Crystallographica Section D: Biological Crystallography*, 2011, 67, p. 235-242].

Electron Density Map Calculation, Model Building and Refinement:

The structures were determined by molecular replacement using PHASER implemented in PHENIX [McCoy, A. J. et al., *J Appl Crystallogr*, 2007, 40, p. 658-674], using the structure of D50S (PDB ID: 2ZJR) as a starting model. Once initial phases were obtained, rigid body and positional refinement were performed using Phenix.refine [Afonine, P. V. et al., *Acta Crystallogr D Biol Crystallogr*, 2012, 68, p. 352-67] and CNS [Brunger A. T. et al., *Acta Crystallogr D Biol Crystallogr*, 1998, 54(5), p. 905-21].

For R-free calculations during refinement cycles, random 5% of the data were omitted during refinement. Tracing the ribosomal RNA and remodeling the ribosomal proteins with SA strain NCTC8325 sequence according to the electron density maps was performed using Coot [Emsley, P. et al., *Acta Crystallogr D Biol Crystallogr.*, 2010, 66(4), p. 486-501], Rosetta ERRASER [Chou, F. C. et al., *Nat Methods.*, 2013, 10(1), p. 74-6] was used to facilitate further building and to improve the quality of the RNA geometry. Figures were generated using Pymol [The PyMOL Molecular Graphics System, Version 1.5.0.4 Schrödinger, LLC]. Sequence alignments were performed using BLAST [Altschul, S. F. et al., *J Mol Biol.*, 1990, 215(3), p. 403-10] and presented by JalView [Waterhouse, A. M. et al., *Bioinformatics*, 2009, 25, p. 1189-1191]. Structure alignments were performed using LSQMAN [Kleywegt, G. J. and Jones, T. A., Structure, 1995, 3, p. 535-540] and Coot.

FIG. 1 presents a graphic illustration of the large ribosomal subunit of SA (SA50S), wherein the rRNA is colored in grey, the rProteins are colored in various colors, the PTC is marked by a red star and the approximate path of the internal exit tunnel is marked by a band colored in dark blue.

In summary, the structures of the large ribosomal subunit from *Staphylococcus aureus* and of its complexes with linezolid, telithromycin and BC-3205 were determined by X-ray crystallography, and the data were refined using molecular replacement phasing. Table 3 presents a summary of the crystallographic data and structure refinement statistics of native SA50S structure (SA50S), SA50S structure in complex with linezolid (SA50Slin), SA50S structure in complex with BC-3205 (SA50SBC-3205) and SA50S structure in complex with telithromycin (SA50Steli). Ninety three percent of the nucleotides and most of the amino acid residues of 26 of SA50S rProteins (ribosomal proteins) were traced in the electron density map. Also detected was electron density putatively assigned to hydrated ions such as Mg$^{2+}$ and Mn$^{2+}$.

TABLE 3

| Subject | SA50S | SA50Slin | SA50SBC-3205 | SA50Steli |
|---|---|---|---|---|
| Crystal information | | | | |
| Space group | P6$_5$22 | P6$_5$22 | P6$_5$22 | P6$_5$22 |
| a [Å] | 279.6 | 279.9 | 280.9 | 282.7 |
| b [Å] | 279.6 | 279.9 | 280.9 | 282.7 |
| c [Å] | 872.7 | 870.6 | 875.6 | 877.1 |
| α, β, γ [°] | 90, 90, 120 | 90, 90, 120 | 90, 90, 120 | 90, 90, 120 |
| Complex with | — | linezolid | BC-3205 | telithromycin |
| Diffraction data statistics | | | | |
| X-ray source | ID23-1/2 (ESRF) | ID23-1 (ESRF) | ID23-2 (ESRF) | ID23-1 (ESRF) |
| Wavelength [Å] | 0.873, 0.972 and 1.00 | 0.972 and 1.00 | 0.873 | 0.973 |
| Number of crystals | 11 | 8 | 20 | 11 |
| Crystal oscillation [°] | 0.1 | 0.1 | 0.1 | 0.1 |
| Resolution [Å] | 50-3.51 (3.57-3.51) | 200-3.4 (3.46-3.4) | 50-3.43 (3.47-3.43) | 50-3.45 (3.51-3.45) |
| Unique reflections | 236855 | 246474 | 253918 | 257382 |
| Observed reflections | 2813593 | 1392748 | 2109298 | 1792405 |
| Redundancy | 12 (6) | 5.7 (2.8) | 8.3 (3.4) | 7 (5) |
| Completeness [%] | 96.3 (84.3) | 89.4 (64.8) | 92.1 (78.9) | 98.5 (96.5) |
| <I>/<σ> | 7.4 (1.43) | 8.45 (1.16) | 10.51 (1.21) | 8.84 (1.21) |
| R-merge [%] | 25.3 (97.8) | 15.6 (77.6) | 15.2 (74.4) | 16.5 (92.6) |

TABLE 3-continued

| Subject | SA50S | SA50Slin | SA50SBC-3205 | SA50Steli |
|---|---|---|---|---|
| Refinement | | | | |
| R-factor [%] | 20.18 | 20.87 | 20.42 | 19.53 |
| R-free (5%) [%] | 24.65 | 25.23 | 24.2 | 23.57 |
| RMSD bonds [Å] | 0.006 | 0.006 | 0.006 | 0.006 |
| RMSD angles [°] | 1.161 | 1.12 | 1.099 | 1.118 |

FIGS. 2A-F present the weighted $2F_o$-$F_c$ electron density maps of linezolid (FIG. 2A), telithromycin (FIG. 2B) and BC-3205 (FIG. 2C), contoured at 1.0 σ, and the weighted $F_o$-$F_c$ electron density maps of linezolid (FIG. 2D), telithromycin (FIG. 2E) and BC-3205 (FIG. 2F), contoured at 3.0 σ.

Example 4

Main Cross-Species Structural Variability

Structural Variability in rRNA Between Species:

Sequence alignment of the 23S rRNA shows 81%, 76% and 73% identity between S. aureus and D. radiodurans, E. coli, and T. thermophilus, respectively, suggesting almost identical rRNA structures with some diversity. Since this diversity may highlight clues for species specificity in resistant mechanisms stemming from the unique features of SA50S structure, its structure was compared with the structures of D50S (PDB ID: 2ZJR), T70S (PDB IDs: 2WDL and 2WDK) and E70S (PDB IDs: 2AW4 and 3R8S).

The crystal structure comparison revealed significant similarities in the rRNA folds of all high resolution structures available to date. Nevertheless, several internal structural differences, alongside some regions that are located on the surface of the 50S subunit were identified, which seem to originate from sequence variability rather than from crystal packing interactions. Some of such regions are located mainly at the subunit interface within the active ribosome. The general locations of the variable rRNA regions within the entire large subunit are shown in FIGS. 3A-B and close-up illustrations for each region are shown in FIGS. 4A-H.

FIGS. 3A-B present a graphic illustration of the structure of SA50S showing relative locations of the rRNA regions with fold variability on the SA50S subunit, wherein SA50S 23S rRNA is shown in teal, the variable regions are shown in orange and (FIG. 3A and FIG. 3B) are rotated 90° with respect to each other.

FIGS. 4A-H present graphic illustrations of superimposed structure models of S. aureus (colored in teal), D. radiodurans (colored in grey), E. coli (colored in purple) and T. thermophilus (colored in orange), showing the structural variability in the rRNA backbone, wherein (FIG. 4A) emphasizes the h25 region, (FIG. 4B) emphasizes the h9 region, (FIG. 4C) emphasizes the h63 region, (FIG. 4D) emphasizes the h10 region, (FIG. 4E) emphasizes the h79 region, (FIG. 4F) emphasizes the h15 and h16 regions, (FIG. 4G) emphasizes the h68 region, and (FIG. 4H) emphasizes the h28 region.

Herein and throughout, lower case "h" is used as a prefix for the numbers of the rRNA helices.

As can be seen in FIGS. 4A-H, a rather significant fold variance was observed in the h28 region; in SA50S it possesses a different orientation compared to the other three structures (FIG. 4H). Additional examples are found in the h25 and h9 regions that have different folds in all 4 structures (FIGS. 4A and B); the h63 region, which is in proximity to the intersubunit bridge B5 and has a different length in each of the four structures, longest is in E70S, shorter in SA50S and T70S and the shortest in D50S (FIG. 4C). Helices h10 and h79, which are interacting with each other and with rProteins L28 and L2, respectively, are extended in SA50S and E70S compared to their conformation in T70S and D50S (FIGS. 4D and E). The h16 region of SA50S and E70S is the longer compared to that of T70S and D50S (FIG. 4F). Interestingly, h15 does not exist in E70S crystal structure and could not be traced in D50S, whereas it is clearly resolved and shows small structural diversity between SA50S and T70S, indicating a varying level of flexibility (FIG. 4F).

As can further be seen in FIGS. 4A-H, the h68 region, which is involved in the binding of rProtein L1, EF-P (elongation factor-G), RRF (ribosomal recycling factor) and belongs to the intersubunit bridge B7a with the 30S subunit, is longer in SA50S than the h68 of T70S and D50S; however it is not fully traced in SA50S structure (FIG. 4G).

FIGS. 5A-B present graphic illustrations of the flexible nucleotides at the PTC and at the exit tunnel (FIG. 5A), showing U2506, U2585, A2062, A2602 and U2491, where the P-site tRNA (shown as a green surface) and the A-site tRNA (shown as a blue surface) would bind, whereas S. aureus 23S RNA backbone and nucleotides are colored in teal, and D. radiodurans, T. thermophilus and E. coli nucleotides are shown in grey, orange and purple, respectively, and further showing the flexible nucleotides towards the tunnel opening (FIG. 5B), wherein A90, A91 and A508 are located in the ribosomal exit tunnel, detected with different conformations in all 4 structures, and a possible path of the backbone of a modeled nascent poly-alanine chain is represented by a yellow string.

As can be seen in FIGS. 5A-B, within the core of the ribosome, the rRNA fold is mostly conserved in the four eubacterial ribosome structures, including the previously identified flexible nucleotides with variable conformations at the PTC, namely U2506, U2585, A2062, A2602, U2491 and at the exit tunnel, namely A508 and A90-91.

Structural Variability in rProteins Between Species:

Sequence alignment of the large ribosomal subunit proteins showed an overall identity of about 50% between the S. aureus, E. coli, T. thermophilus and D. radiodurans.

The crystal structure comparison of the rProteins showed a greater diversity in their detailed structures compared to the differences observed for the rRNA structure. Typically, the main features of the rProteins folds, such as the globular domains and the secondary structure elements that interact with the rRNA are rather conserved; however, several SA50S rProteins contain extensions that were not seen in any other ribosome structure previously published. Relative positions of the globular domains of the rProteins on the subunit surface are shown in FIGS. 6A-D.

FIGS. 6A-D present a graphic illustrations of the surface of the SA50S indicating the locations of the globular regions of the rProteins, whereas rRNA is shown in grey and the various rProteins are shown in different colors, showing a view from the SA50S intersubunit surface (FIG. 6A), a view from the SA50S outer surface (FIG. 6B), and views of a +90 degrees and −90 degrees vertical rotation of the intersubunit surface (FIGS. 6C and D respectively).

It is noted that almost all the rProteins contain N- and/or C-terminal extensions, as well as extended internal loops (both types may reach 70-80 Å in length), which penetrate into the ribosome core and interact with the ribosomal RNA. These extensions contain most of the structural variability of the rProteins.

SA rProteins numbering is used throughout the comparative analysis owing to the significant variability in the rProteins sequences and folds of the four compared structures.

The Inter-Subunit Interface:

FIGS. 7A-B present a graphic illustrations of the subunit interface, showing some of the structural differences of the rProteins, while focusing on L5 (FIG. 7A) and L16 (FIG. 7B).

As can be seen in FIGS. 7A-B, there is a notable structural variability in M38-A53 and G126-D144 loops of L5 that participates in the B1b intersubunit bridge with 30S subunit (16S, colored in grey) with rProtein S13 (colored in dark green) (FIG. 7A). Also the SA50S L16 is extended compared to T70S, E70S and D50S structures thus may form a unique interaction net with A-site tRNA acceptor stem (colored in blue) and the P-site tRNA (colored in green) interacts with the loop L77-V90 that has some structural variability (FIG. 7B). By superposition of the SA50S subunit on the corresponding part in T70S, one can identify the structural variability in M38-A53 and G126-D144 loops of L5 that interact with rProtein S13 in the 70S ribosome, embracing S13 interface helix in all four structures (FIG. 7A). The L16 protein is positioned in the intersubunit surface and interacts with the A-site and P-site tRNAs, superposed on PDB ID: 2WDK. The N-terminal of L16 SA50S is extended compared to T70S, E70S and D50S structures thus may form a unique interaction network with A-site tRNA acceptor stem (see, FIG. 7B).

Furthermore, the fold of the N-terminal of protein L2 in SA50S is somewhat different from that of E70S, in which L2 is longer. Interestingly in D50S, 30 residues of protein L2 could not be traced, whereas in SA50S only 14 residues could be traced. The rProtein L5 participates in the B1 intersubunit bridge with the 30S subunit, together with the rProtein S13.

FIGS. 8A-B present a graphic illustration that emphasizes the structural differences between SA50S, T70S, E70S and D50S in the rProteins that interact with substrates, while focusing on L28 (FIG. 8A) and L27 (FIG. 8B).

As can be seen in FIG. 8A, protein L28 is located close the 50S surface, where the CCA 5' of the E-site tRNA (shown in yellow) binds, and the L28 in D50S and T70S has a 15 residues extended loop (S19-K27) that reaches h11 of the 23S rRNA. This loop is shorter in SA50S and E70S that interacts with h21 and h75. As can be seen in FIG. 8B, L27 in D50S reaches to the acceptor stem of the P-site tRNA (shown in green), whereas in T70S it reaches the PTC, in the proximity of the CCA end of the P-site tRNA. Additional differences found in L14 structures are within the core of the subunit may facilitate substrate stabilization during protein synthesis. As previously observed, the flexible N-terminal of L27 appears in several conformations in four differently obtained crystal structures. In the presently provided SA50S crystal structure, the N-terminal of L27 is discernible by in the electron density map (can be traced) from residue 19 (based on sequence alignment) and is folded slightly differently than in the other 50S structures from other species. It has been previously reported that SA has an extended L27 N-terminus which is being cleaved post-translationally by a specific and essential protease, prior to or concurrent with ribosome assembly. Therefore in the presently provided SA50S crystal structure only 10 residues of the N-terminal are not modeled (traced) due to a fragmented electron density, confirming the flexibility of this part of the structure. In the E70S crystal structure a shift of 4-5 residues is suggested, based on sequence alignment of L27 on *T. thermophilus, D. radiodurans* and SA, and thus indicating that only 4-5 amino acid residues cannot be traced in the electron density map due to local chain flexibility and motility. In D50S, where almost the entire N-terminal was traced in the electron density map, and no tRNA exists in the crystal, superposition on the T70S with 3 tRNA molecules in the complex, indicating that it may reach the acceptor stem of the P-site tRNA, whereas in T70S it reaches the PTC interacting with the CCA 3'end of the P-site tRNA (see, FIG. 8B).

The Nascent Protein Exit Tunnel:

The exit tunnel is of around a 100 Å in length. It has a non-uniform shape with a variable diameter. It contains a constriction located about 5-7 peptide bonds away from its entrance, which is shaped at its far end, by the hairpin loops of rProteins L4 and L22 that reach the tunnel walls in all four compared structures despite some small sequence and structural variability.

L4 loop of *S. aureus* is more hydrophobic compared to the other compared bacterial species. From the opposite tunnel wall, the L22 hydrophobic hairpin loop has a similar fold in all structures compared; however, the orientations of R92 (R/S/R in T70S, D50S and E70S) are somewhat different in all four structures. It is noted that the macrolide (e.g., Erythromycin) binding site is proximal to this constriction.

FIGS. 9A-G present graphic illustrations that emphasizes the structural differences between SA50S, T70S, E70S and D50S in the rProteins at the walls of the nascent protein exit tunnel, the subunit's core and central protuberance, whereas the possible path of the backbone of a modeled nascent protein chain is indicated in lime/yellow in some of the illustrations.

Figure 9A:
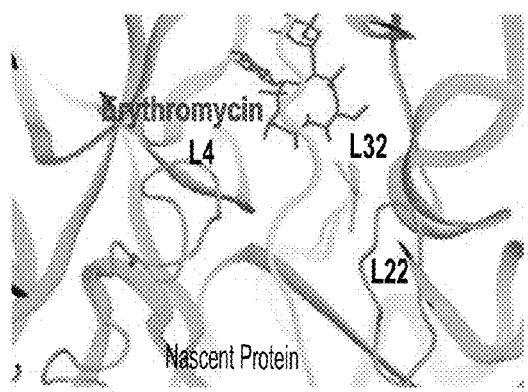
Figure 9B:
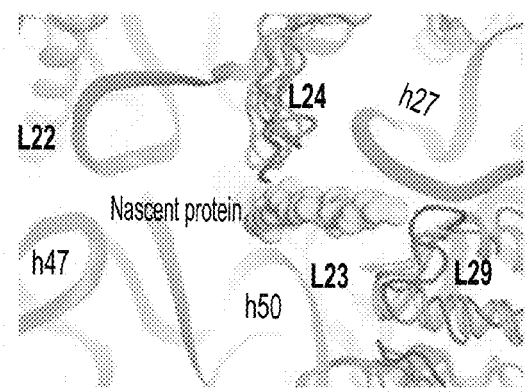
Figure 9C:
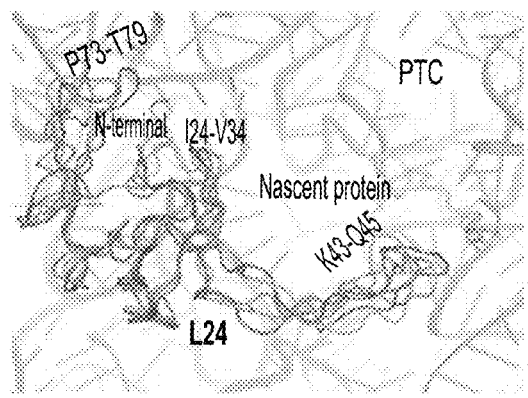
Figure 9D:
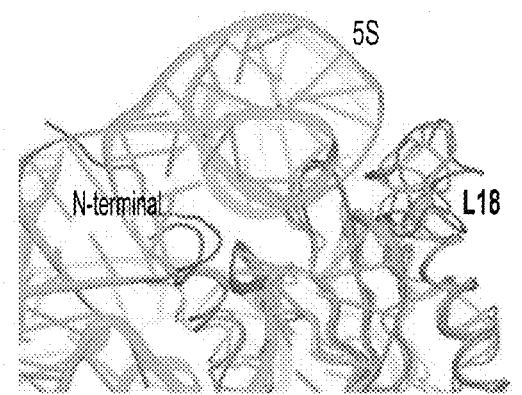
Figure 9E:
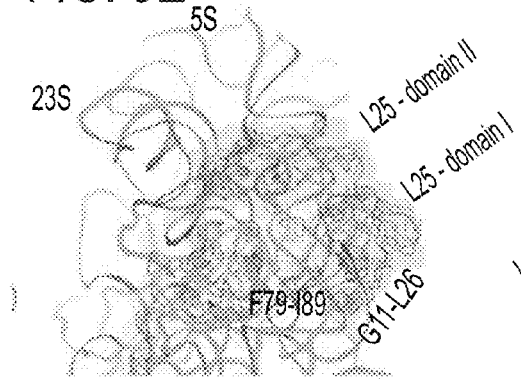
Figure 9F:
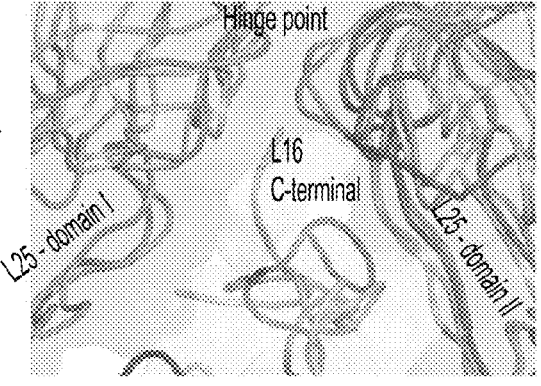
Figure 9G:
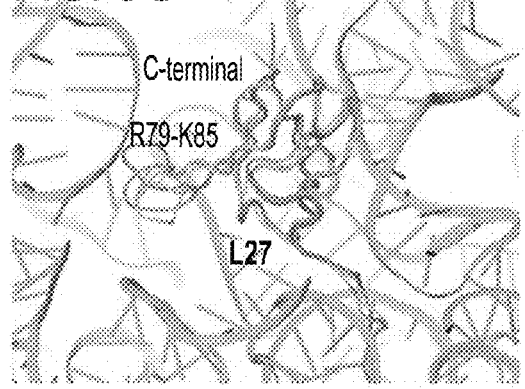

As can be seen in FIGS. 9A-G, L32 N-terminal in D50S and T70S is elongated relative to SA50S and E70S, thus reached the rims of the erythromycin binding site (FIG. 9A); a view into the exit tunnel opening shows structural variability of the rProteins L23, L24, and L29 (FIG. 9B); the L24 is compared in all 4 structures (FIG. 9C). The L18 N-terminal domain is elongated in SA relative to D50S, T70S and E70S reaching the other side of the central protuberance (FIG. 9D); the L25 domains are shown, as well as structural variability in the fold of G11-L26, I49-T69, F79-186 loops, and the L16 C-terminal is longer in T70S than in SA50S, D50S and E70S (FIG. 9E); a zoom-into view of the hinge between the L25 domains shows that the L16 C-terminal is longer in T70S structure than in SA50S, D50S and E70S where it penetrates into the proximity of L25, thus changing the angle between L25 domains (FIG. 9F); and the L27 R79-K85 loop and C-terminal fold exhibits variability among the 4 structures (FIG. 9G).

The N-terminals of L32 in D50S and T70S are elongated relative to SA50S and E70S, thus creating a void proximal to the macrolides binding site. This void may be exploited for potential new or improved drugs (i.e. extended macrolides). In addition, L32 V24-Q37 that reaches the subunit surface, possess structural variability among the 4 structures. Its C-terminal is 14-17 residues shorter in SA50S than in D50S, T70S and E70S.

At the vicinity of the tunnel opening structural variations were observed in ribosomal proteins L23, L29, L24, L32 and L22, creating different surfaces for ribosomes interactions with cellular factors, such as the translocon, ER membranes, chaperons and the likes. The L23 K63-Y71 loop that is pointing into the tunnel, displays a different conformation in SA50S and T70S in comparison to E70S and D50S. Specifically, in the four compared structures, residue R67 (Q in E70S) points into the tunnel in different orientations. The tyrosine in D50S stacks to A508 nucleotide but A508 has a different conformation in each of the 4 structures, which underlines its flexibility (see, FIG. 4B). The L23 C-terminal of SA50S is similar in length to its mates in D50S and T70S, but its fold is different from that of E70S, which has an extended C-terminal tail. Consequently, this region of the subunit surface that interacts with other cell components as the ER membrane or chaperons is altered among the four structures examined (see, FIG. 4B).

The L24 N-terminal interacts with h7 and the junction between h18, h19 and h20 of the 23S rRNA. The D50S N-terminal is 10-13 residues longer than in the other 3 structures. The SA50S and T70S N-terminals are shorter (the SA50S N-terminal first two amino acids could not be traced due to not interpretable density) and the E70S N-terminal is the shortest. The E70S L24 I24-V34 loop folds different than in SA50S, D50S and T70S whereas K43-G55 loop of SA50S folds similar to T70S exhibiting extended loop, different from E70S and D50S. Additionally, the 5' end of L24 T79-I93 loop and the C-terminal tail are highly divergent among the 4 structures (FIG. 9C). In E70S, the L37-T40 loop of rProtein L29 is extended compared to the 3 other structures (FIG. 9B).

Subunit Core and the Central Protuberance:

The rProteins globular regions are located on the surface of the large ribosome subunit. Their long extended tails and loops penetrate into the subunit core and interact with the rRNA. Since differences in proteins that are interacting with the rRNA may result in allosteric alterations in the nucleotides, several substantial structural variability in ribosomal core proteins are noted herein.

FIGS. 10A-H present graphic illustrations emphasizing the structural differences between *S. aureus* (colored in teal), *D. radiodurans* (colored in grey), *T. thermophilus* (colored in orange) and *E. coli* (colored in purple) in some rProteins at the subunit surface.

As can be seen in FIGS. 10A-H, SA50S rProtein L3 has a unique extended A57-L67 loop compared to those of each of D50S, T70S and E70S (FIG. 10A), and that the SA50S L17 has an extended (T65-A81) loop which is unique to SA50S, its C-terminal is about 10 amino-acids longer than in E70S, and it is also longer than its counterparts in the other 3 organisms (FIG. 10B). The length variations detected in the V6-I17 surface loop of protein L4 and N-terminal of L15 that is located in its vicinity, whereas the most extended is found in SA50S, less extended in E70S and D50S and has altogether different orientation in T70S (FIG. 10C). The C and N-terminals of L4 has different backbone folds in the four eubacterial structures (FIGS. 10D-E). SA50S L15 loops I69-T89 and T89-V97 have different structures compared to the corresponding loops in D50S, T70S and E70S (FIG. 10F). The L15 N-terminal in E70S, D50S (traced from the 4th amino acid), T70S (traced from the 5th amino acid), is the shortest in SA50S (traced from the 1st amino acid) (FIG. 10G). The T70S L28 globular domain has a fold that differ significantly from all other L28 structures compared (FIG. 10H).

L14 loop L25-S28 is extended in D50S compared to SA50S, E70S and T70S structures and makes a unique interaction with h95 in addition to the common interaction with h90. L15 N-terminal is a long extended strand with different fold among the compared structures (SA50S exhibiting is the shortest L15 N-terminal) that penetrates into the subunits core (see, FIGS. 10C and 10G), and interacting with protein L35 which has a similar fold in the four compared structures. The N-terminal of SA50S L17, which is located in proximity to h100-h101, h61 and h96, is 4 residues shorter relative to other 3 structures compared (FIG. 10B).

The central protuberance which lies on the surface of the 50S subunit is a sub-complex of the 5S rRNA with rProteins L5, L18, L25, L27 and L25 (referred to as TL5 in the context of T50S and CTC in the context of D50S). This rProtein interacts with the 5S rRNA. In E70S rProtein L25 is built of a single domain, in SA50S and T70S it has two domains and in D50S the CTC protein contains three domains. The first L25 domain of SA50S and E70S has an extended G11-L26 loop that interacts with 5S rRNA. The F79-I86 loops that interact with the 23S rRNA have different backbone folds and orientations in the four compared structures. The C-terminal of L16 R134-T141 reaches the L25 domains interface and 5S rRNA. The N-terminal of L16 is longer in T70S and penetrating deeper into the domains interface, thus, the angle between the two TL5 domains is larger compared to D50S and SA50S (see, FIGS. 9D and 9E). L18 N-terminal in SA50S is longer than in E70S, D50S and T70S. Its N-terminal has been traced only from the eighth and eleventh amino acid respectively. It reaches rProtein L5 that is located on the other side of the 5S rRNA (see, FIG. 9D). The rProtein L27 has a similar structure in all four compared structures apart from variability in the fold of R79-K85 loop that reaches the 5S rRNA in all structures. Structural variations of the C-terminal that reaches the subunit surface are also observed (see, FIG. 9F) in addition to the gross differences in the N-terminal tail mentioned above.

The Subunit Surface:

Among the structural differences identified in the structures of the large ribosomal subunits that are located on their surfaces is SA50S rProtein L3 that has an extended (H58 R69) loop next to h100 of 23S rRNA (see, FIG. 10A). Similarly, rProtein L17 of SA50S has a unique extended T65-A81 loop; its C-terminal is about 10 amino acid residues longer than in E70S, and is also longer than in the other three compared structures. In both L3 and L17 these differences cause a different shape of the subunit surface (see, FIG. 10B). Also, the N- and C-terminals of L29, which reach the subunit surface, possess variable folds in the four compared structures. The N-terminals are extended in T70S and E70S compared to their folds in SA50S and D50S structures, whereas the C-terminals are of similar length but their fold is variable.

In addition, variability in SA50S L3 backbone fold compared with D50S, T70S and E70S was observed. Among them E29-V34 and F91-A112 and loops V15-P24, S142-P151, G152-P170 and Q187-K198 have a different fold and orientation in SA50S compared to T70S and E70S (see, FIG. 10A and FIG. 13A). The L4 of SA50S has an extended V6-I17 surface loop compared to this loop in E70S and D50S, which in T70S adopts a different orientation (see, FIG. 10C). In addition, in SA50S L4 N-terminal has a different backbone fold, Q119-E132 (see, FIG. 10E), and different structure and orientation of its C-terminal tail (I186-T195) (FIG. 10D) compared to E70S, T70S and D50S.

The SA50S L15 C-terminal domain is located on the surface of the 50S subunit. Its loops I69-T89 and T89-V97 have different structure compared to the corresponding loops of E70S, but similar to T70S and D50S C-terminal domain (see, FIG. 10F). FIG. 10C shows the surface shared by L4 and L15 and their overall structural differences among the four different crystal structures. The L15 N-terminal is the longest in E70S, shorter in D50S (traced from the fourth amino acid residue) and shorter in T70S (traced from the fifth amino acid residue). The L15 N-terminal is the shortest in SA50S (traced from the first amino acid residue) but its 70 amino acids residues extended the N-terminal tail intercalated differently with the 23S rRNA of the 4 structures compared (see, FIGS. 10F and 10G).

Furthermore, although L19 N-terminus of SA50S and D50S are positioned differently, both interact with h101 while D50S L19 N-terminus interacts with h100 and L3 and while T70S and E70S N-terminals are shorter. In SA50S L21 N-terminal, K24-D31 loop and G43-V58 loop have a slightly different backbone fold than the other three compared structures. The N-terminal of D50S L22 is 22-residues longer compared to SA50S, T70S and E70S resulting in a rather different surface of the D50S subunit. In addition, the core structure of L28, which is situated in proximity to the outer surface of the large subunit, is folded differently in the four compared structures. Also, the L28 I38-W48 loop adopts a different orientation in SA50S compared to E70S, T70S and D50S (FIG. 10H).

The L30 N-terminal that is located on the particle's outer surface is positioned differently in SA50S and T50S structures compared to E70S, whereas the D50S N-terminal is shorter. The L30 C-terminal, that also reaches the subunit outer surface, is longer in T70S compared to the other three compared structures.

FIGS. 11A-B present graphic illustrations emphasizing the structural differences between SA50S, T70S, E70S and D50S in the N-terminal of protein L32 that resides in the second shell around the erythromycin binding pocket.

As can be seen in FIG. 11A, the L32 is shorter in SA50S (colored in teal) as well as in E70S (colored in purple) compared to its length in the ribosomes of the non-pathogenic bacteria *D. radiodurans* (colored in grey) and *T. thermophilus* (colored in orange) as seen in FIG. 11B.

In summary, some of the differences in rProteins detected in SA include:

(i) the length of the N-terminus of rProtein L17 (see, FIG. 10B);

(ii) the flexible N-terminal of rProtein L27 that displays structural fold variability in proximity to the acceptor stem and 3' end of P-site tRNA (see, FIG. 8B);

(iii) a shorter loop in rProtein L28 that lies in proximity to E-site tRNA; and (iv) a significantly shorter N-terminal region of rProtein L32 that results in the creation of an additional void at the rims of the macrolides binding site.

Thus, in D50S and T70S the N-terminal tails of L32 reach the erythromycin binding pocket, whereas in the pathogenic SA50S and the potential pathogenic E70S they are distal to this pocket (see, FIGS. 11A and 11B). Notably, in most bacteria L32 N-terminal is shorter, similar to what is seen for SA50S and for E70S (see seq. alignment attached). In addition, in all known structures of eubacterial ribosomes nucleotide A2058 is stacked onto G2057 that interacts with residue 5 of L32 N-terminal tail. The sequence and structure variability of this residue (Lys in SA50S, T70S and D50S and Gln in E70S), creates different environments around A2057.

A detailed comparative structural analysis presenting the main structural differences in SA50S rProteins and rRNA is summarized in Table 4 and Table 5 respectively.

TABLE 4

| rProtein | Residues | Difference | Ribosome Site | FIG. |
|---|---|---|---|---|
| L2 SEQ ID NO. 3 | N-terminal | Variation in its length and fold. 30 residues are missing from the D50S structure. In the current SA50S structure it is traced from the 3$^{rd}$ residue. | intersubunit surface, next to h34 | |
| L3 SEQ ID NO. 4 | V15-P24 | Different fold and orientation compared with T70S and E70S. | subunit surface next to L14 and L19 | 10A |
| L3 SEQ ID NO. 4 | E29-V34 | Variability in backbone folds in all four structures. | subunit surface within its globular domain | 10A |
| L3 SEQ ID NO. 4 | A57-L67 | SA50S extended loop next to h100 of 23S rRNA, compared to E70S, D50S and T70S. | subunit surface next to h100 | 10A |
| L3 SEQ ID NO. 4 | F91-A112 | Variability in backbone folds in all four structures. | subunit surface within its globular domain | 10A |
| L3 SEQ ID NO. 4 | H134-P170 | Different fold and orientation compared with T70S and E70S. | subunit core, in between h61, h35 and h90 | 13B |
| L3 SEQ ID NO. 4 | Q187-K198 | Different fold and orientation compared with T70S and E70S. | subunit surface within its globular domain | 10A |
| L4 SEQ ID NO. 5 | N-terminal | Different backbone folds in the four structures. | subunit surface within its globular domain, next to h29 | 10E |
| L4 SEQ ID NO. 5 | V6-I17 | Extended surface loop compared to this loop in E70S and D50S. This loop adopts a different orientation in T70S structure. | subunit surface within its globular domain | 10C |
| L4 SEQ ID NO. 5 | W65 | W65 of SA50S (W/W/Y in E70S, T70S and D50S) points into the exit tunnel and has a different orientation relative to the other structures. | Protein exit tunnel entrance | 13E, 13F |

TABLE 4-continued

| rProtein | Residues | Difference | Ribosome Site | FIG. |
|---|---|---|---|---|
| L4 SEQ ID NO. 5 | K66 | K66 in SA50S (R/G/P in E70S, D50S and T70S) interacts with nucleotide U790 in the 23S rRNA that is pointing into the exit tunnel. | Protein exit tunnel entrance | 13E, 13F |
| L4 SEQ ID NO. 5 | K68 | Conserved among all 4 structures. Situated in proximity to the PTC nucleotides A2060 and U2061, but exhibits a different orientation in each of the 4 structures. | Protein exit tunnel entrance | 13E, 13F |
| L4 SEQ ID NO. 5 | R72 | R72 in SA50S (R/R/N in E70S, T70S and D50S) points into the exit tunnel in different orientations in the four structures. | Protein exit tunnel entrance | 13E, 13F |
| L4 SEQ ID NO. 5 | Q119-E132 | Different backbone fold in the four structures | subunit surface, close to h19, h20 junction | 10E |
| L4 SEQ ID NO. 5 | C-terminal | Different structure and orientation in the four structures. | subunit surface within its globular domain, next to h28 | 10E |
| L5 SEQ ID NO. 6 | M38-A53 | High structural variability observed among four structures. | part of intersubunit bridge B1b | 7A |
| L5 SEQ ID NO. 6 | G126-D144 | High structural variability observed among four structures. | part of intersubunit bridge B1b | 7A |
| L14 SEQ ID NO. 9 | L25-S28 | Extended loop in D50S compared to SA50S, E70S and T70S, forming a unique interaction with h95 in addition to the common interaction with h90. | Subunit core in between h90, h92 and h95 | |
| L15 SEQ ID NO. 10 | N-terminal | L15 N-terminal is a long extended strand with fold variation among the four structures that begins at the subunit surface and penetrates into the core of the 23S rRNA. In SA50S this loop is the shortest. | reaches subunit surface, next to L4 | 10C |
| L15 SEQ ID NO. 10 | I69-V97 | Different structure of this loop in the four structures. | subunit surface within its globular domain, close to h28 | 10F |
| L16 SEQ ID NO. 11 | N-terminal | SA50S L16 N-terminal is extended compared to T70S, E70S and D50S structures thus may form unique interactions with A-site tRNA acceptor stem. | intersubunit surface, between h38 and h89, A-site tRNA binding site. | 7B |
| L16 and L25 SEQ ID NOs. 11 and 20 | C-terminal | T70S C-terminal is longer, penetrating deeper between L25 domains thus, the angle between the L25 domains is larger compared to D50S and SA50S L25 structures. | central protuberance, subunit surface | 9F |
| L17 SEQ ID NO. 12 | N-terminal | SA50S N-terminal is four residues shorter relative to other 3 structures compared and it folds differently. | Subunit core in between h96, h91 and h100 | 10B |
| L17 SEQ ID NO. 12 | T65-A81 | This loop is most extended in SA50S. | subunit surface between h47, h59 and h57 | 10B |
| L17 SEQ ID NO. 12 | C-terminal | ~10aa longer in E70S compared to other three structures, thus is extended at the subunit surface. | subunit surface within its globular domain, close to h101 | 10B |
| L18 SEQ ID NO. 13 | N-terminal | SA50S N-terminal is longer than E70S tail, reaching protein L5 across the 5S rRNA. In D50S and T70S this N-terminal has been traced only from aa 8 and 11 respectively. | central protuberance, subunit surface | 9D |
| L18 SEQ ID NO. 13 | T53-A73 | Variable fold among the four structures. | central protuberance, subunit surface | 9D |
| L19 SEQ ID NO. 14 | N-terminal | SA50S L19 N-terminus interacts with h101 whereas D50S L19 N-terminus interacts with h100 and L3. T70S and E70S N-terminus are shorter. | subunit surface next to h101 | |
| L21 SEQ ID NO. 16 | N-terminal | SA50S backbone fold is slightly different than the backbone fold in the other three structures. | subunit surface within its globular domain next to L20 | |
| L21 SEQ ID NO. 16 | K24-D31 | SA50S backbone fold is slightly different than the backbone fold in the other three structures. | subunit surface next to h45 | |
| L21 SEQ ID NO. 16 | G43-V58 | SA50S backbone fold is slightly different than the backbone fold in the other 3 structures. | subunit surface within its globular domain next to L20 | |
| L22 SEQ ID NO. 17 | N-terminal | D50S N-terminal is 22 residues longer compared to SA50S, T70S and E70S resulting in a rather different surface of the D50S subunit at this face. | subunit surface next to h24 | |
| L22 SEQ ID NO. 17 | K83 | This Lys side chain in SA interacts with nucleotide C1261 (h26) adopting a different orientation compared with E70S, T70S and D50S structures. | Protein exit tunnel entrance | |
| L22 SEQ ID NO. 17 | R84 | R84 in SA50S, E70S and T70S points in different direction than in D50S. | Protein exit tunnel entrance | |

TABLE 4-continued

| rProtein | Residues | Difference | Ribosome Site | FIG. |
|---|---|---|---|---|
| L22 SEQ ID NO. 17 | S85-F94 | Hydrophobic loop that folds differently in SA50S, D50 and T70S compared to E70S | Protein exit tunnel entrance | |
| L22 SEQ ID NO. 17 | R86 | Only in SA50S residue R86 (I/L/M in D50S, T70S and E70S) reaches nucleotide C1325 (h50) U/A/A in E70S, D50S and T70S. | Protein exit tunnel entrance | |
| L22 SEQ ID NO. 17 | Q90 | Q in SA and R in D50S and T70S. Pointing into the exit tunnel. Glutamine side chain is shorter than arginine, allowing a wider passage in the tunnel. Since E. coli has a different backbone fold in this region, the aligned residue is K and it's in a different position. | Protein exit tunnel entrance | |
| L22 SEQ ID NO. 17 | R92 | R/S/R in T70S, D50S and E70S. Orientation is different among all four structures. | Protein exit tunnel entrance | |
| L23 SEQ ID NO. 18 | K63-Y71 | Pointing into the tunnel, displays a 3 different orientation between SA50S/T70S, D50S and E70S . . . Especially, residue R67 (Q in E70S) which points into the tunnel in different directions | Protein exit tunnel | 4B |
| L23 SEQ ID NO. 18 | C-terminal | SA50S C-terminal tail is similar in length to D50S and T70S. It folds different from E70S that exhibits extended C-terminal tail. Consequently this part of the subunit surface, which interacts with the ER membrane, is altered among the four structures. | Protein exit tunnel end (surface) | |
| L24 SEQ ID NO. 19 | N-terminal | Reaches the outer subunit surface via interactions with h7 and the junction h18, h19, h20 of the 23S rRNA. In D50S the N-terminal of L24 is 10-13 residues longer than in the other 3 structures. The SA50S and T70S N-terminals are shorter (the SA50S N-terminal is partly not traced due to uninterruptable density). The E70S N-terminal is the shortest. | subunit surface via interactions with the h7 and the junction h18, h19, h20 | 9C |
| L24 SEQ ID NO. 19 | I24-V34 | The E70S loop folds different than in SA50S, D50S and T70S. | surface next to h7 | 9C |
| L24 SEQ ID NO. 19 | K43-G55 | This loop has a different orientation and a slightly different fold between all four structures. | Protein exit tunnel end (surface) next to h24 and h7 | 9C |
| L24 SEQ ID NO. 19 | T79-I93 | Highly divergent among the four structures. | surface of the subunit between L7 and L18 | 9C |
| L24 SEQ ID NO. 19 | C-terminal | Highly divergent among the four structures. | surface, close to h7 | |
| L25 SEQ ID NO. 20 | domains | L25 of E70S is a single domain protein whereas in SA50S and T70S L25 is composed of 2 domains and in D50S L25 is composed of 3 domains. | central protuberance, subunit surface | 9E |
| L25 SEQ ID NO. 20 | G11-L26 | SA50S and E70S have an extended loop that interacts with 5S rRNA. | central protuberance, subunit surface | 9E |
| L25 SEQ ID NO. 20 | I49-T69 | Variable backbone fold and orientation in all four structures. | central protuberance, subunit surface | |
| L25 SEQ ID NO. 20 | F79-I86 | Variable backbone fold and orientation in all four structures. | central protuberance, subunit surface | |
| L27 SEQ ID NO. 21 | N-terminal | SA50S L27 is truncated as could be tracing only from aa 19 (by sequence alignment). Its positioning is somewhat different compared to T70S (complex with tRNA) and D50S embracing the superimposed P-site tRNA. In E70S (2AW4) structure N-terminal tail is the shortest and also embracing the superimposed P-site tRNA. | intersubunit surface | 8B |
| L27 SEQ ID NO. 21 | R79-K85 | Variable fold among the four structures. | central protuberance, subunit surface | |
| L27 SEQ ID NO. 21 | C-terminal | Structural variations, as reported earlier for all known structures (Maguire, B. A 2005). | central protuberance, subunit surface | 9G |
| L28 SEQ ID NO. 22 | Entire protein | The T70S L28 has different fold compared with its fold in E70S, D50S and SA50S structures. | intersubunit surface | 10H |
| L28 SEQ ID NO. 22 | S19-K27 | In D50S and T70S L28 has an extended loop, compared to E70S and SA50S, that reaches h11 of the 23S rRNA and should interact with the CCA 5' of E-site tRNA. | intersubunit surface, between h11 and h21 | 8A |
| L28 SEQ ID NO. 22 | I38-W48 | Adopts a different orientation in SA50S compared to E70S, T70S and D50S | intersubunit surface between h79 and h10 | 10H |
| L29 SEQ ID NO. 23 | N-terminal | Extended in T70S and E70S compared to SA50S and D50S N-terminal structures. | subunit surface, next to h7 | |
| L29 SEQ ID NO. 23 | L37-T40 | E70S loop is more extended than in the 3 other structures. | Protein exit tunnel exit (surface) | 9B |
| L29 SEQ ID NO. 23 | C-terminal | Variable folds among the four structures. | subunit surface next to h18 | |

TABLE 4-continued

| rProtein | Residues | Difference | Ribosome Site | FIG. |
|---|---|---|---|---|
| L30 SEQ ID NO. 24 | N-terminal | Pointing in different directions in SA50S and T50S structures compared to E70S. In D50S the N-terminal is shorter. | subunit surface close to its C-terminal and h38 | |
| L30 SEQ ID NO. 24 | C-terminal | Longer in T70S compared to the other three structures. | subunit surface close to its N-terminal and h38 | |
| L32 SEQ ID NO. 25 | N-terminal | D50S and T70S are elongated relative to SA50S and E70S, thus penetrating deeper into the tunnel wall. | Protein exit tunnel entrance | 9A, 11A, 11B |
| L32 SEQ ID NO. 25 | V24-Q37 | Structural variability among the four structures | surface between L22 globular domain h101 and h99 | |

TABLE 5

| 23S rRNA SEQ ID NO. 1 | Difference | Ribosome Site | FIG. |
|---|---|---|---|
| h9 | Different fold among the four structures compared. | Surface, in vicinity to L23 | 4B |
| h10 | Elongated in SA50S and E70S structures relative to T70S and D50S structures. | interacting with h79 and with proteins L28 | 4D |
| h15-h16 | In SA50S h15 and h16 fold differently than in E70S and h16 in D50S. Interestingly, h15 is missing in the E70S structure and could not be traced in D50S, presumably owing to its flexibility. | Surface, in vicinity to L28 | 4F |
| h25 | Different fold among the four structures compared. | Surface, in vicinity to L21 | 4A |
| h28 | Different fold among the four structures compared. | next to the surface of rProtein L4 globular domain | 4H |
| h63 | Variable lengths in all four structures, longest in E70S, shorter in SA50S and T70S and shortest in D50S. | in proximity to intersubunit bridge B5 | 4C |
| h68 | Not fully traced in SA50S structure as it is longer than h68 of T70S and D50S structures. | involved in the binding of rProtein L1, EF-P, RRF and is part of the intersubunit bridge B7a | 4G |
| h79 | Elongated in SA50S and E70S relative to T70S and D50S. | interacting with h10 and with proteins L2 | 4E |
| U2506, U2504, U2609, U2585, A2062, A2602 (h93), U2491 (h89) | Flexible nucleotides. | PTC | 5A |
| A508, A90-A91 (h7) | Flexible nucleotides. | exit tunnel exit, on the surface of the subunit | 5B |

Example 5

The Complex Crystal Structure of SA50S with Antibacterial Agents

FIGS. 12A-F present graphic illustrations of linezolid bound to SA50S (SA50S in complex with linezolid), referred to herein as SA50Slin (A and B), telithromycin bound to SA50S, referred to herein as SA50Steli (C and D) and BC-3205 bound to SA50S, referred to herein as SA50SBC-3205 (E and F).

FIG. 12A shows a comparison of native SA50S peptidyl transferase center (PTC) structure (colored in teal) and SA50Slin complex (colored in pale orange). Hydrogen bonds between linezolid (colored in orange) and 23S rRNA are shown in black dashes. FIG. 12B shows an overlay of the structures of various ribosome-linezolid complexes [SA50Slin (colored in pale orange), H50Slin (colored in green) complexed also with CCA-Phe substrate analog (colored in teal) (PDB ID: 3PCW), D50Slin (colored in grey) (PDB ID: 3DLL) and of the model of E70Slin (colored in pink). The color code of the rRNA components of the various linezolid binding pockets is the same as of corresponding linezolid molecules. FIG. 12C shows a comparison between native SA50S PTC (colored in teal) and SA50Steli complex (colored in red). The main hydrogen bond between telithromycin (colored in slate) and 23S rRNA is shown in black dashes. FIG. 12D shows a structural overlay of various telithromycin conformations observed in various ribosome-telithromycin complex structures, presenting SA50Steli (colored in slate), D50Steli (colored in orange) (PDB ID: 1P9X), H50Steli (colored in grey) (PDB ID: 1YIJ), E70Steli (colored in pink) (PDB ID: 3OAT), and T70Steli (colored in green) (PDB ID: 3OI3). The color code of the rRNA components of the various telithromycin binding pockets is in brighter tone than the corresponding telithromycin molecules. FIG. 12E shows a comparison between the structure of the PTC in native SA50S (colored in teal) and in SA50SBC-3205 (colored in purple), the arrows in this figure show the movements of nucleotides U2585 and U2506 in the bound versus the native structure. Hydrogen bonds between BC-3205 (colored in violet) and 23S rRNA are shown as black dashes. FIG. 12F shows a structural overlay of various pleuromutilins in their binding pockets in (colored in violet), D50S-SB571519 (colored in green) (PDB ID: 2OGM), D50S-retapamulin (colored in cyan) (PDB ID: 2OGO), D50S-tiamulin (colored in slate) (PDB ID: 1XBP), and D50S-SB280080 (colored in lemon) (PDB ID: 2OGN). Only one hydrogen bond between BC-3205 (colored in violet) and 23S rRNA is shown as black dashes.

Crystal Structure of SA50S-Linezolid Complex:

The SA50S-linezolid complex structure (SA50Slin) revealed that linezolid is bound at the PTC, blocking the A-site, thus perturbing tRNA accommodation, in an orientation grossly similar to that observed in other ribosome linezolid complexes with D50S, H50S and the E50Slin model. However, in SA50Slin complex the flexible nucleotide U2585 undergoes a significant rotation and forms a hydrogen bond with the 04 of the linezolid morpholino ring, which yields a nonproductive conformation of the PTC (see, FIGS. 12A and 12B).

The flexibility of U2585 plays a role in the rotatory motion of the translocation of the tRNA 3' end from the A-site to the P-site. Hence, fixing its conformation by a hydrogen bond with linezolid should paralyze the PTC catalytic activity. The linezolid 1,3-oxazolidin-2-one moiety and acetamide group form additional hydrogen bonds with G2505 and A2451, respectively. The fluorophenyl moiety of linezolid is located in a heteroaromatic crevice formed by the PTC residues C2451 and C2452, the so-called A-site cleft. All of its other interactions with the rRNA nucleotides, namely G2061, C2501, U2504, U2506 and G2447, are either Van der Waals or hydrophobic interactions.

Comparing SA50Slin structure (see, FIG. 12A) with other available crystal structures or models of large ribosomal subunits in complex with linezolid, namely H50Slin, D50Slin and E70Slin model (see, FIG. 12B) revealed that in all structures the drug is bound at the same pocket; however, there are subtle differences between the conformation of the linezolid acetamide group in SA50Slin and the other structures. These include a 100-120 degree rotation of the acetomide group which, in SA50Slin enables fixation of A2451 by a hydrogen bond. In addition, in H50Slin complex, the NH of the acetomide group is forming a hydrogen bond with the oxygen on the phosphate of G2505, whereas in D50Slin complex no such specific interaction is observed. Noteworthy, H50Slin complex was crystallized in the presence of CCA-Phe (tRNA 3' end substrate analogue), assuming that in such environment it should interacts strongly with the 50S subunit P-site. Indeed, it seems that this P-site analog altered linezolid conformation, compared to other linezolid complex structures that were determined with empty P-site. Interestingly, a hydrogen bond between the morpholino ring of linezolid and nucleotide U2585 was observed in D50Slin and in SA50Slin, but not in H50Slin. Additionally, for detecting linezolid in the H50Slin crystal structure the drug concentration was three orders of magnitude higher than the concentrations used for linezolid soaking into D50S or SA50S crystals.

The Structure of SA50S-Telithromycin Complex:

The SA50Steli structure shows that telithromycin is bound at the $MLS_BK$ binding site, and forms the typical ketolides (and macrolides) hydrogen bond between its desosamine sugar and A2058. At this position it is partly blocking the protein exit tunnel, as was found in other ribosome-$MLS_BK$ complex structures [Schlünzen, F. et al., Molecular Microbiology, 2004, 54(5), p. 1287-1294; Belousoff, M. J. et al., P.N.A.S USA, 2011, 108(7), p. 2717-2722 and Berisio, R. et al., J Bacteriol., 2003, 185(14), p. 4276-9]. In SA50Steli complex the flexible nucleotide U2062 is rotated compared to its conformation in native SA50S and its conformational range is minimized by the hydrogen bond with A2503 (see, FIG. 12C). All of its other interactions with the rRNA nucleotides, namely G2505, A2059, C2611 and U746, are either hydrophobic interactions or based on Van der Waals distances.

Comparing SA50Steli structure with other available crystal structures of ribosomal particles in complex with telithromycin [Berisio, R. et al., J Bacteriol., 2003, 185(14), p. 4276-9; Tu, D et al., Cell, 2005, 121(2), p. 257-70; Dunkle, J. A. et al., Proc Natl Acad Sci USA, 2010, 107(40), p. 17152-17157; and Bulkley, D. et al., Proc Natl Acad Sci USA, 2010, 107(40), p. 17158-63] revealed that in all structures the drug is bound at the same pocket but with distinct differences in the orientations of the alkyl-aryl moiety. Similar orientation of this moiety was seen in SA50Steli and in H50Steli. In both, the arm is folded back over the macrolactone ring, thus creating a rather compact structure of the drug; however, in SA50Steli the alkyl-aryl arm is reaching the center of the tunnel about 5 Å closer to the PTC compared to its location in H50Steli and may block the nascent protein progression in an earlier stage. In this orientation the alkyl-aryl arm is almost overlapping the location of the cladinose sugar of erythromycin in its complex with D50S (see, FIG. 13A). In contrast, in T70Steli and E70Steli this arm is stacked to A752 and U2609, a base pair that is located on the tunnel wall further away from the PTC, so that it can block nascent protein progression about 10 Å away from the point of blockage observed in H50Steli. In D50Steli, the alkyl-aryl arm is extended, thus blocks the tunnel by interacting with U790 across the tunnel, creating a barrier located 15 Å further along the tunnel compared to SA50Steli (see, FIG. 12D). It has been suggested that the structure of E70Steli reflects the telithromycin binding mode to the ribosomes of medically relevant (namely pathogenic) eubacteria species, since A752-U2690 base pair is conserved among all eubacteria [Dunkle, J. A. et al., Proc Natl Acad Sci USA, 2010, 107(40), p. 17152-17157], and in addition, telithromycin resistant Streptococcus pneumonia AA752 mutant has been isolated and characterized. Nevertheless, in SA50Steli the alkyl-aryl arm of telithromycin does not interact with A752-U2690 base-pair, thus demonstrating that antibiotic (antibacterial agent) binding modes are species specific; hence, clearly demonstrating that general description of the overall antibiotics binding properties is the main outcome from the previous structures cannot be extrapolated safely to other species.

The Structure of SA50S-BC3205 Complex:

In SA50SBC-3205 complex structure, BC-3205 is bound at the PTC, where the tricyclic mutilin core is blocking the A-site, and its C14 extension is pointing into the P-site, thus perturbing A-site and P-site tRNA accommodation, as was found in other ribosome-pleuromutilin complex structures with D50S. In SA50SBC-3205 the conformation of the flexible nucleotide U2585 is different from that of the unbound SA50S and its conformational range is reduced because of partial overlap by the BC-3205 (see, FIG. 12E). In addition, U2506 is shifted towards the walls of the binding pocket, forming a hydrogen bond between its 04 carbonyl to the valyl moiety NH₂ of BC-3205. An additional hydrogen bond is formed between the acetyl carbonyl and the NH₂ of G2061. All of its other interactions with the rRNA nucleotides, namely A2063, A2503, U2504, G2505, A2451, C2452 and U2585, are either hydrophobic interactions or based on Van der Waals distances.

Comparing SA50SBC-3205 with the crystal structures of D50S in complex with various pleuromutilins (see, FIG. 12F) revealed that all pleuromutilins bind to the same pocket, albeit by somewhat different interactions, including a shift of U2585. In SA50SBC-3205, this shift is larger than in all other pleuromutilin complexes so that the base of U2585 is located about 6 Å away from its position in the native conformation. Similarly, a movement of U2506 towards the bound drug was observed in pleuromutilins complexes with D50S. Notably, in SA50SBC-3205, U2506 forms a hydrogen bond with the NH₂ of the valyl moiety of the drug, hence its shift is the largest. Consequently the two sides of BC-3205 are held within its binding pocket by hydrogen bonds, compared to the single hydrogen bond created in the other pleuromutilins complexes with G2061, thus indicating a better fit of BC-3205 to its binding site. This additional interaction of BC-3205 seems to account for its higher potency against MRSA resistant strains and its low $IC_{50}$ value.

Example 6

Structural Analysis of Known SA Resistance Mechanisms

FIGS. 13A-F present graphic illustrations of structures of native SA50S rRNA and rProteins (colored in teal), D50S (colored in grey), E70S (colored in purple) and T70S (colored in orange) superimposed for comparative analysis and study of the resistance and cross resistance mechanisms in SA, showing rRNA nucleotides of SA in regions where they can be well aligned with the corresponding nucleotides in all other structures used for the comparisons.

FIG. 13A shows SA telithromycin (colored in slate) conformation within its SA complex where its alkyl-aryl arm is folded such that it overlaps the desosamine sugar of erythromycin (colored in red) in its complex with D50S. SA50teli L22 (colored in blue) is superimposed on rProtein insertion resistant mutant of L22 (colored in red) that allows nascent protein progression although it binds erythromycin (PDB ID: 4U67). FIG. 13B shows SA50S rRNA nucleotides of the linezolid (colored in orange) and BC-3205 (colored in green) binding sites are superimposed on the corresponding E70S rRNA (colored in purple). G2576 is located in the 2nd shell around the linezolid and BC-3205 binding sites, in proximity to the 1st shell nucleotides G2505 and U2506 thus G2576 mutation may cause alterations in them. The locations of the L3 mutations acquiring resistant of SA are marked on the protein chain (colored in yellow). For comparison, the structure of E70SL3 (colored in purple) is superposed on SA50S L3 (colored in teal). Key structural differences are marked by arrows. The orange stars indicate deletions (SA numbering system is used). FIGS. 13C-D show linezolid (colored in orange), chloramphenicol (colored in green) and dalfoprostin (streptograminsA, colored in red) in the SA50S rRNA binding pocket. FIG. 13E shows SA50S rRNA A2058 and A2059 are main binding determinants of MLS$_B$K family of antibiotics, represented here by erythromycin (PDB ID: 3OFR) (colored in red). rProteins L4 and L32 form a second shell around erythromycin binding pocket next to A5058 and A2059. Structure variability of L4 among D50S, E70S, T70S and SA50S is also shown. FIG. 13F shows rProtein L4 is in vicinity to SA linezolid (colored in orange) and SA BC-3205 (colored in green) binding pockets. The structural variability of its loop (W65-Q75) in all fours species is also shown.

SA linezolid resistance is caused mainly by G2576U (SA G2603U) mutation, a nucleotide that is more than 98% conserved throughout all kingdoms, and located in the second shell around linezolid binding pocket, at the PTC, in vicinity to rProtein L3. This nucleotide is stacked to G2505 that is located adjacent to U2504 and U2506. These three nucleotides are part of the first shell around linezolid binding pocket and make direct contacts with linezolid in all available crystal structures of its complex with the large ribosomal subunit. It is conceivable that a mutation in G2576 may cause alterations in these first shell nucleotides since it is stacked to the first shell nucleotide G2505 and forms a hydrogen bond with U2506. Compared to E70S, the L3 loop G152-P170 in SA50S is bent towards the minor groove of h72 away from G2576, hence permitting more flexibility (see, FIGS. 13B-C).

SA linezolid resistance is also caused by rRNA mutations in U2500A, A2503G, U2504C and G2447U nucleotides, which are more than 98% conserved throughout all kingdoms. Within the SA50S, D50S and H50S-linezolid complexes, the drug interacts with U2504; mutating it to C will abolish the CU base-pair interactions with C2452, thus may change the shape of the linezolid binding pocket. G2447 interacts with A2451 that is part of the linezolid binding pocket. The mutation G2447U may form a new base-pair with A2451 that may limit the A2451 flexibility thus influencing drug binding. U2500 is base-paired with A2453, and its mutation to A will abolish the base-pair interactions and consequently change the PTC environment (see, FIG. 13D). These nucleotides are part of a network that stabilizes the PTC, which is also the binding site of a few antibiotics (antibacterial agents) from different families. Once mutated, the interactions described above are eliminated and antibiotic binding does not occur. The G2447U mutation, which renders also *M. smegmatis* and *M. tuberculosis* linezolid resistant, confers lethality in *E. coli* and has been suggested to belong to the functional differences between the ribosomes of Gram positive and Gram negative bacteria. Interestingly, significant structural similarity was observed in this region of ribosome from T70S, D50S, E70S and SA50S, which represent both Gram positive and Gram negative species. Such high cross-types (Gram positive and Gram negative) sequence similarity opens the path for designing ligands that are characterized by high affinity to large ribosomal subunits of both Gram positive and Gram negative bacteria.

Cross resistance to linezolid, chloramphenicol and dalfoprostin (streptograminA; a constituent of Synercid which contains also streptogramin B) is associated with the second shell nucleotide G2576U mutation. Linezolid, chloramphenicol and streptograminsA bind at the PTC via the first shell nucleotide G2505 that is stacked to U2576. In addition, cross resistance of SA to linezolid and chloramphenicol, of which the binding pockets partially overlap, may be caused by G2505A and U2500A mutations although the conservation level of these nucleotides is more than 98% throughout all kingdoms. These mutations indicate that despite its high conservation, this nucleotide is not essential for ribosomal function. Nucleotide G2505 is base-paired to C2610 and its ribose and phosphate are located in the vicinity of the antibiotic. The mutation G2505A leads to a mismatch in this base pair, thus altering the antibiotic binding pocket. Similarly, U2500 is base paired with A2453 and has hydrophobic interactions with U2504. The mutation U2500A is disrupting the base pair U2500-A2453, thus may enable U2504 tilting away from the linezolid binding pocket (see, FIG. 13C).

SA resistant mutations are also associated with the region of rProtein L3 that is located in proximity of the PTC. This rProtein is involved in several resistance mechanisms, such as: (a) G152D and G155R that acquire resistance to linezolid, tiamulin, chlorampenicol and retapamulin, (b) ΔS145 acquire resistance to linezolid and tiamulin, (c) R149S trigger resistance to tiamulin, (d) ΔF127-H146 acquire linezolid resistance, (e) S158L and D159Y cause resistance to tiamulin and retapamulin, (f) G144D and S153Y acquire resistance to retapamulin and (g) the combinations of G152D, D159Y, G144R or G152D, D159Y, G155R, H134N or G152D, D159Y, G155R, A150T acquire resistance to retapamulin, tiamulin and chloramphenicol. In SA50S, the fold of L3 loop G139-A150 is similar to its folds in D50S and T70S, all bending toward h90 and h62 (lower case "h" is used throughout as prefix for the numbers of the rRNA helices), but is different in E70S as it bends towards h61 major groove (see, FIG. 13B). All mutated amino acids that were found in clinical resistant isolates are located in the L3 region that is adjacent to the third shell of nucleotides around the PTC, appear to reshape the antibiotics binding pocket (colored in yellow in FIG. 13B). Mutations in the L3 loops that are in vicinity of G2578 and C2575, which are part of the second shell nucleotides, may affect G2576 and its interactions with nucleotides G2505-U2506 that are part of the tiamulin and linezolid binding pockets.

L3 loop F127-P170 is located also in the vicinity to G2574 that interacts with A2572, which is proximal to the flexible nucleotide U2504. In D50S and SA50S, this nucleotide is located in the first shell around linezolid and tiamulin binding pockets, and interacts with them (see, FIG. 13B). This nucleotide has been previously implicated in PTC antibiotics resistance acquired by induced fit alterations that although not directly interacting with the bound drugs, reshape the binding pocket via networks of remote interactions, most of which through the flexible nucleotide U2504. In another SA linezolid resistance strain, a deletion of F127-H146 occurs in rplC gene, which is encoding rProtein L3. In L3 wild type, this loop is located within the area described above, in vicinity to 23S rRNA helix h90 nucleotides G2576-G2580, which reside in the second shell around linezolid binding pocket. Loop deletion may eliminate or alter interactions of L3 with its proximal rRNA, thus may reshape the drug binding pocket and hamper the antibiotics binding (see, FIG. 13B). Similarly, mutations in locations somewhat distal from the actual antibiotic binding pockets that confer resistance by allosteric rearrangements have been detected in other systems.

U2506 seems to be one of the most flexible nucleotides within the linezolid and BC-3205 binding pockets. It adopts a different conformation in each of the available crystal structures (see, FIG. 12B) [Wilson, D. N. et al., *P.N.A.S. USA*, 2008, 105(36), p. 13339-44; Ippolito, J. A. et al., *J Med Chem*, 2008, 51(12), p. 3353-6; Selmer, M. et al., *Science*, 2006, 313(5795), p. 1935-1942; and Schuwirth, B. S. et al., *Science*, 2005, 310(5749), p. 827-834], resulting in a significantly different shapes of the linezolid binding pockets in the pathogen SA versus the archaeal H50S and the whole E70S ribosomes.

Nucleotides A2058 and A2059 are more than 98% conserved in eubacteria. Notably, in all higher organisms, including archaea, position 2058 is a guanine. These nucleotides, particularly A2058, are known as the main determinants for binding MLS$_B$K antibiotics by direct interactions (see, FIG. 13E) [Schlünzen, F. et al., *Nature*, 2001, 413 (6858), p. 814-821; Harms, Jorg M. et al., *BMC biology*, 2004, 2, p. 4]. Indeed, the identity of the nucleotide in position 2058 plays a key role not only in patient-pathogen discrimination, but also in resistance to MLS$_B$K antibiotic families that is acquired either by A2058G mutation, or by post posttranscriptional modifications performed by the erm genes, which encode methyltransferase, an enzyme that methylates A2058 in SA as well as in other eubacteria. Other mutations in this region, i.e. A2058U, A2058G and A2059G cause resistance to azithromycin and erythromycin in SA.

A2058 and A2059 are in direct contact with the W65-K68 loop of rProtein L4, which has diverse sequences in SA50S, E70S, T70S and D50S (see, FIGS. 13E-F). Mutations in rProtein L4, G69A and T70P acquire SA resistance to linezolid, Q67K, G69E, G69A and T70P mutations acquire SA resistance to erythromycin. In addition, AK68 and AG69 are susceptible to linezolid and K68Q mutation acquires SA resistance to linezolid, pleuromutilins, chloramphenicol and tedezolid. Since L4 Q67-T70 loop is located in the vicinity of the phosphate of A2059, which belongs to the MLS$_B$K binding pocket, the above mentioned mutations may alter the W65-Q75 loop conformation thus affecting A2059 conformation (see, FIGS. 13E-F). In E70S, T70S and SA50S structures, residue R72 of L4 is arginine, whereas in D50S it is asparagine. Each of these four side chains of residue 72 points to a different direction, creating different environment around nucleotide A2059 in the four compared crystal structures. Residue K68 is located in vicinity of the phosphate of nucleotide G2061 (SA G2088, DR G2044) and the sugar-phosphate backbone of A2059 that are in direct contact with linezolid. It has a similar orientation in E70S, SA50S and T70S, but is different from D50S (see, FIG. 13F). The mutation K68Q replaces a long positively charged side chain by a shorter uncharged one, with no electrostatic interactions with G2061 and A2059. G69A and T70P point mutations introduce hydrophobic residues, which may increase the flexibility of the binding pocket, thus reducing the efficiency of the binding and explaining how resistance to linezolid is gained in these cases. All available NCBI sequences of rProtein L4 indicate that its residue 68 lysine is highly conserved; however, in H50S, the respective residue is serine, a short polar uncharged residue, which seems to reduce binding efficiency. This may be an additional feature of the weaker binding mode of linezolid to H50S.

The L22 hairpin loop is part of the exit tunnel wall point mutations, deletions and insertions in this loop, between residues R80-S108, in SA confer resistance to erythromycin, synercid and telithromycin although its location is too far for direct chemical interactions with the bound drugs. Interestingly, similar resistance mutations were also observed in additional bacterial species including some pathogens. Crystal structure of one of these mutants provided the structural basis for this resistance, showing that the insertion of 3 amino acids (VPR after R109-D50 numbering) into L22 hairpin loop reshapes the binding region. Thus, the repositioning of the tip of L22 hairpin loop, triggered a cascade of structural rearrangements of the rRNA nucleotides that propagates to erythromycin binding site, reshaping the tunnel walls in a fashion permitting nascent protein progression in the tunnel even in the presence of erythromycin (see, FIG. 13A). It is conceivable that similar mechanisms play roles in acquiring resistance in SA deletion/insertion mutants.

Multidrug resistance to phenicols, lincosamides, oxazolidinones, pleuromutilins, and streptograminA (PhLOPS$_A$) is facilitated in SA by the Cfr and RlmN genes that code enzymes that methylate A2503 in two positions, namely C8 and C2. A2503 is more than 98% conserved throughout all kingdoms; nevertheless, it can be modified without terminating protein biosynthesis. A2503 methylation, which increases its size, interferes with $PhLOPS_A$ drugs binding, thus conferring resistance to them. Similarly, mutation or methylation of A2503G causes linezolid resistance in SA presumably by creating a steric clash with the drug (see, FIG. 13B).

Example 7

Structural Differences and Selectivity Between Eukaryotic and Pathogen Ribosome

Selectivity, namely the distinction between bacterial pathogens and eukaryotes, is crucial for clinical usage of antibiotics. Below we highlight the main differences between the structures of the antibiotics binding sites in the large ribosomal subunits of the pathogen SA and their mates in eukaryotic ribosomes, based on comparisons of SA50S structure with the currently available eukaryotic ribosome structures, namely those of *S. cerevisiae* 80S ribosome [Ben-Shem, A. et al., *Science*, 2011, 334(6062), p. 1524-1529] and *T. thermophila* 60S large ribosomal subunit [Klinge, S. et al., *Trends In Biochemical Sciences*, 2012, 37(5), p. 189-198], as well as on the relevant sequences in human ribosome. Another study compared between the binding pockets of inhibitors of eukaryotic ribosomes in *S. cerevisiae* and *E. coli* [de Loubresse, N. G. et al., *Nature*, 2014, 513(7519), p. 517].

FIGS. 14A-C present graphic illustrations of regions in the superimposed structures of *S. cerevisiae* 60S (PDB ID: 3U5D) (colored in yellow), *T. thermophilia* 60S (PDB ID: 4A18) (colored in red) and SA50S (colored in teal), showing the sequence and structural variability among eukaryotes and prokaryotes rRNA antibiotics binding pockets and vicinity.

FIG. 14A shows the $MLS_BK$ (erythromycin (PDB ID: 3OFR) (shown in red) binding pocket in SA50S and the two eukaryotes structures. FIG. 14B shows the ketolides binding pocket of telithromycin in SA50S and the two eukaryotes structures. FIG. 14C shows the PTC binding pocket of tiamulin (PDB ID: 1XBP) (colored in purple) in SA50S and the two eukaryotes structures.

Macrolides, lincosamides, ketolides and streptogramins$_B$ ($MLS_BK$) bind to the protein exit tunnel near to its constriction. Their selectivity is attributed to the difference in the identity of binding pocket nucleotide 2058 that binds the desosamine sugar of the macrolides, which is guanine in eukaryotes and adenine in eubacteria. In addition, the second shell nucleotides around the macrolide binding site play a key role is selectivity. Thus, G2057 and G2056 are base-paired with C2611 and C2612 in SA50S. In eukaryotes both 2057 and 2056 nucleotides are adenines (see, FIG. 14A), hence their base-pairing interactions are compromised. These two base-pairs play important roles in the stabilization of position of G2058. It is worth noting that in D50S and T70S, only one of these base-pairs, namely between C2611 and G2057 is maintained, while the other is replaced by His 4 of L32 that extents towards the macrolide binding pocket deeper than in SA50S and E70S structures.

Nucleotides C2611 and C2610 belong to the $MLS_BK$ binding pocket. Both are uridines in eukaryotes and the variability in their identity between prokaryotes and eukaryotes is also important for pathogen/patient selectivity.

Another nucleotide that is related to the selectivity of SA50S $MLS_BK$ binding pocket is C2586 that in SA is located in proximity to the C12-C13 of the erythromycin macrolactone ring and is U in *E. coli* and eukaryotes. C1782 and U1781 are additional nucleotides that may contribute to SA specificity in the binding pocket of $MLS_BK$. C1782 is U in *E. coli* and eukaryotes, as well as nucleotide U1781 which is U in prokaryotes, including SA, but A in eukaryotes (see, FIG. 14A).

Interestingly, in the SA50S and T70S and D50S, nucleotide 790, which is U in all structures except D50S, is pointing into the tunnel, whereas it points into the particle's core in the two eukaryotes structures (see, FIG. 14B). In SA50teli, nucleotide U2609 is base-paired with A752 that is an important determinant of ketolides improved activity; however, as discussed above, the drug is not directly interacting with this base-pair. Nevertheless, its absence may alter the ketolides binding pocket thus affecting their inhibitory activity. This base-pair is found in yeast but not in *T. termophila*. Additional selectivity determinants at the $MLS_BK$ binding pocket are nucleotide U746, a first shell nucleotide, which is G in eukaryotes, and G753, that is a second shell nucleotide around telithromycin binding pocket, is A in *E. coli* but U in eukaryotes, whereas residue U754, a third shell nucleotide, is C in eukaryotes (see, FIG. 14B).

The exit tunnel nucleotides that are conserved among prokaryotes versus eukaryotes are A2058, A2057, C2610, C2611, C2612, U1781, U746 and U754. SA sequence specific nucleotides versus eukaryotes and other prokaryotes are C2586, C1782 (both at the exit tunnel) and G753 (second shell to telithromycin binding pocket). Thus, drug selectivity of eubacteria versus eukaryotes is achieved by eight nucleotides that are located at the $MLS_BK$ binding pocket or in its second to third shells. Interestingly, nucleotides 2586 and 1782 that belong to the $MLS_BK$ binding site are C in SA but U in other prokaryotes and eukaryotes. These unique identities may play a role in the SA species specific drug resistance mechanisms, and hence may be exploited for the design of novel specific antibiotics. Similarly, G753, a second shell nucleotide at the $MLS_BK$ binding pocket is G in SA but A in EC and U in eukaryotes might be used for selective distinction between the SA and other ribosomes.

The PTC that is highly conserved in all kingdoms contains flexible nucleotides, detected also in SA50S. Variations in PTC nucleotides orientations between the structures of SA50S and other bacterial and eukaryotic ribosomes include the conserved nucleotides, namely A2062, U2504, U2506, U2585 and A2602. A2062, which has a different orientation in SA50S compared to the eukaryotic ribosomes, is found in resistant strains (see, FIG. 14C). U2504 has been pointed as being at the crossroad of remote mutations networks that hamper binding of PTC antibiotics. U2585 and U2506 display flexibility upon the pleuromutilins binding. U2585 and A2602 are two universally conserved nucleotides facilitating the translocation of the 3'-end tRNA A-site to P-site. Among them, U2585, may also be involved in D-amino acid rejection, and in the synergistic action of members of the streptogramin class of antibacterial agents. Interestingly, the involvement of the PTC second shell nucleotide 2453 in maintaining the PTC conformation is less dependent on its identity. Thus, it is A in bacteria and U in eukaryotes. However, although its role in peptide bond formation seems to be less crucial, it plays a role in drug selectivity at the PTC. The second shell nucleotide C2055 is the only nucleotide around the PTC that is C in bacteria and A in eukaryotes, thus creating different interactions with the first shell nucleotide U2504 in bacteria versus eukaryotes second and third shell nucleotides that are modulating a conserved drug binding site can play roles in selectivity and resistance (see, FIG. 14C). Thus, G2576 and C2055 are both second shell residues around the PhLOPS$_A$ binding site; G2576 is mutated in resistant strains while the residue 2055 is C in prokaryotes and A in eukaryotes, thus has role in selectivity.

Example 8

Design of a Novel Ribosomal Ligand

Following is a general procedure for designing a novel ligand for the SA50S subunit, based on the native and complex structures provided herein. A procedure for designing the ligand is based on developing an expanded pharmacophore and generally involves the following steps:

Providing a set of SA50S complex structures with a diverse set of ligands bound in or near a ribofunctional locus of interest. The set of atomic coordinates of the diverse bound ligands is used as a training set for developing the pharmacophore model.

Superimposing each of the complex structures on the native structure so as to afford a fit between a maximal number of ribosomal atoms in different complexes, thereby affording superimposition of the ligands (the members of the training set) in their bound conformation and relative spatial positions.

Transforming the superimposed ligands into a spatially positioned set of abstract representations of pharmacophore elements. For example, superimposed phenyl rings from different ligands occupying a relatively small space are jointly referred to as an "aromatic ring" pharmacophore element at the center of the space. Likewise, hydroxyl groups are referred to as a "hydrogen-bond donor/acceptor" pharmacophore element.

Identifying the combined pharmacophore having the maximal number of contributions (pharmacophore elements) from each of the complex structures, thereby maximally expanding the pharmacophore.

Designing a rigid molecular skeleton which links spatially all the pharmacophore elements, and designing functional groups on the skeleton corresponding to each of the pharmacophore elements.

In an exemplary embodiment of the invention, a putative ligand is designed as an adduct of moieties which stem from the chemical structure of each of the ligands linezolid, BC-3205 and telithromycin, which are used as a diverse set of ligands for the training set.

According to some embodiments, each of the pre-verified ligands, linezolid, BC-3205 and telithromycin, is individually parsed computationally to arbitrary yet chemically viable segments, which can be used as building blocks of a rationally designed de-novo ligand, according to some embodiments of the present invention.

For example, linezolid can be parsed to the following exemplary and non-limiting moieties:

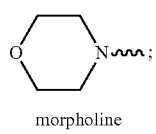

morpholine

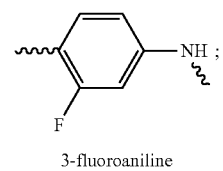

3-fluoroaniline

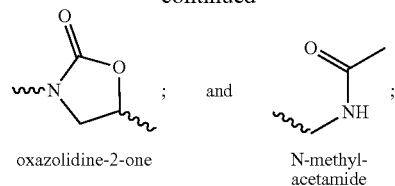

oxazolidine-2-one    N-methyl-acetamide wherein each of the wavy lines represent an optional linking position which can be used to link the moiety to a skeleton of an adduct or to another moiety in the adduct.

Similarly, telithromycin can be parsed to the following exemplary and non-limiting moieties:

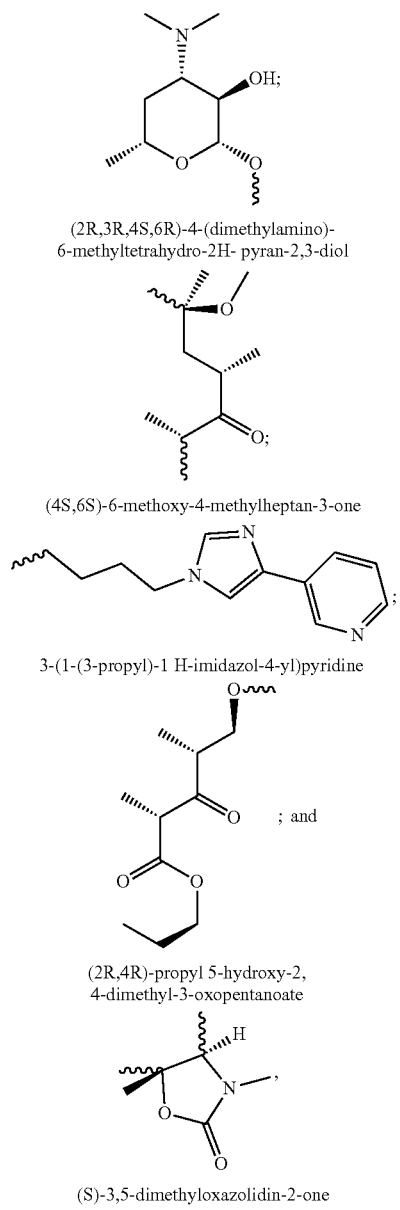

(2R,3R,4S,6R)-4-(dimethylamino)-6-methyltetrahydro-2H-pyran-2,3-diol (4S,6S)-6-methoxy-4-methylheptan-3-one 3-(1-(3-propyl)-1H-imidazol-4-yl)pyridine (2R,4R)-propyl 5-hydroxy-2,4-dimethyl-3-oxopentanoate (S)-3,5-dimethyloxazolidin-2-one wherein each of the wavy lines represent an optional linking position which can be used to link the moiety to a skeleton of an adduct or to another moiety in the adduct.

Similarly, BC-3205 can be parsed to the following exemplary and non-limiting moieties:

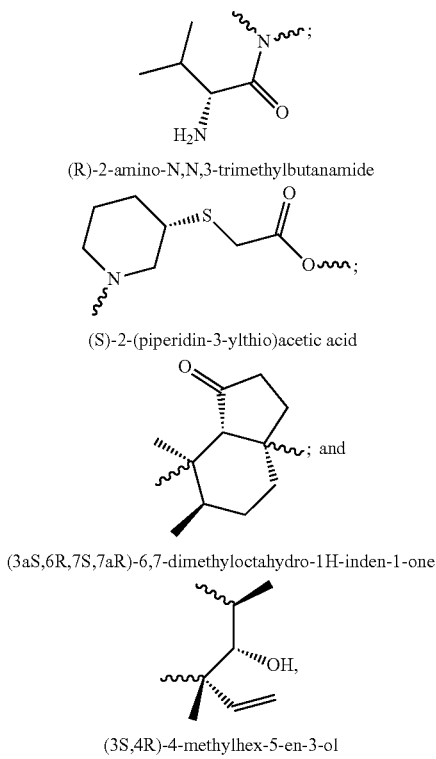

(R)-2-amino-N,N,3-trimethylbutanamide (S)-2-(piperidin-3-ylthio)acetic acid (3aS,6R,7S,7aR)-6,7-dimethyloctahydro-1H-inden-1-one (3S,4R)-4-methylhex-5-en-3-ol wherein each of the wavy lines represent an optional linking position which can be used to link the moiety to a skeleton of an adduct or to another moiety in the adduct.

It is noted that the parsing of a pre-verified ligand can take other forms, and each moiety can be further parsed to sub-moieties and so forth.

In the exemplary embodiment presented herein, the superimposition of the complex structures over the native structure is based on fitting phosphate atoms of the rRNA chains common to all native and complex structures.

FIG. 15 presents an illustration of linezolid (green stick model), BC-3205 (blue stick model) and telithromycin (red stick model), as these three ligands are positioned in the crystal structure of the corresponding complex with SA50S, wherein each complex structures is superimposed on the native SA50S crystal structure, and further presents the molecular surface of the combined ligand structures illustrated as a wire mesh encasing the three ligands, wherein the coloring of mesh corresponds to the color of the ligand which contributes to the molecular surface at the corresponding region thereof.

As can be seen in FIG. 15, linezolid and BC-3205 occupy a similar binding site commonly referred to as the PTC, while telithromycin occupies a proximal binding site commonly referred to as the polypeptide tunnel opening. As can further be seen in FIG. 15, the relatively short distance between the atoms of BC-3205 and telithromycin (about 2.5]) can readily be bridged by a linking moiety in the form of an linking, for example, the isopropyl moiety of BC-3205 (a sub-moiety of the (R)-2-amino-N,N,3-trimethylbutana-mide illustrated hereinabove) to the pyridine moiety of telithromycin. Alternatively, the deoxy-sugar moiety of telithromycin ((2R,3R,4S,6R)-4-(dimethylamino)-6-methyltetrahydro-2H-pyran-2,3-diol) can be linked by a linking moiety to the vinyl moiety of BC-3205 (a sub-moiety of the (3S,4R)-4-methylhex-5-en-3-ol illustrated hereinabove).

Hence, an adduct-type ligand is designed to substantially occupy the space which is at least partially occupied by all three ligands, namely at least a portion of the space delineated in the wire mesh illustration in FIG. 15, and exhibit moieties which belong to the expanded pharmacophore corresponding to the combined structures of all three ligands, such as for a non-limiting example, the morpholine and the N-methylacetamide moieties of linezolid, the cyclopentanone and the 2-amino-3-methyl-1-(piperidin-1-yl)butan-1-one moieties of BC-3205, and the 3-(1H-imidazol-4-yl)pyridine and the oxazolidin-2-one moieties of telithromycin. The moieties are linked by molecular skeleton and linking moieties which are designed to exhibit the moieties in the relative positions and conformation corresponding to the positions and conformations of the corresponding moieties as they appear in the bound form of the corresponding ligand in each of the complex crystal structure. An exemplary skeleton for an exemplary de-novo designed ligand, according to some embodiments of the present invention, can be a moiety that mimics or duplicates the macrolide ring (the large macrocyclic lactone) of telithromycin, or a moiety that mimics or duplicates the bicyclo[5.3.1]undecane or the tricyclic mutilin core of BC-3205. Alternatively, the skeleton can be any alkyl, heteroalkyl, alicyclic, hetero-alicyclic moiety, aryl and/or heteroaryl moiety, and any combination thereof.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

Example 9

The complex crystal structure of SA50S-lefamulin (SA50Slef) Lefamulin (BC-3781), developed by Nabriva Therapeutics, Vienna, Austria, is a semi-synthetic pleuromutilin compound that is highly active against pathogens that are commonly associated with community-acquired bacterial pneumonia (CABP), including multi-drug resistant *S. pneumoniae, S. aureus,* and *M. pneumonia.*

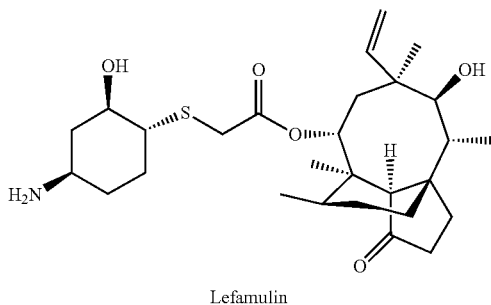 [SMILES: C=C[C@]1(C)C[C@@H](OC(=O)CS[C@@H]2CC[C@@H](N)C[C@H]2O)[C@]2(C)[C@H](C)CC[C@]3(CCC(=O)[C@H]32)[C@@H](C)[C@@H]1O]

Lefamulin

Crystal Structure of SA50S-Lefamulin Complex:

The complex structure of the antibiotic drug lefamulin bound to SA50S, SA50S crystals, obtained essentially as described hereinabove were soaked in a solution containing 22.8 μg/ml lefamulin in a stabilization solution for 6 hours prior to flash freezing and data collection.

The crystal structure of the large ribosomal subunit from *S. aureus* complexed with lefamulin (SA50Slef; PDB ID: 5HL7) was obtained and characterized as summarized in Table 6 below (in parentheses are the values for the highest resolution shells of 3.61-3.55).

TABLE 6

| Subject | SA50Slef |
| --- | --- |
| Space group | P6₅22 |
| a = b [Å] | 282.1 |
| c [Å] | 875.3 |
| α, β, γ [°] | 90, 90, 120 |
| Complex with | lefamulin (BC-3781) |
| X-ray source | ID23-1 (ESRF) |
| Wavelength [Å] | 0.972 |
| Number of crystals | 12 |
| Resolution [Å] | 50-3.55 (3.61-3.55) |
| Unique reflections | 236087 |
| Observed reflections | 2606786 |
| Redundancy | 11.0 (9.2) |
| Completeness [%] | 95.7 (94.6) |
| <I>/<σ> | 9.0 (1.71) |
| R-merge [%] | 20.9 (99.4) |
| Refinement | |
| R-factor [%] | 18.69 |
| R-free (5%) [%] | 22.66 |
| RMSD bonds [Å] | 0.010 |
| RMSD angles [°] | 1.610 |

FIG. 16 presents a graphic illustration of an overlay of lefamulin in the pleouromutilin binding site, as elucidated from the complex structures SA50Slef PDB ID: 5HL7 (orange), D50S-retapamulin (cyan; PDB ID: 2OGO) and D50S-SB280080 (lemon; PDB ID: 2OGN).

FIG. 17 presents a graphic illustration of an overlay of the PTC in native SA50S (teal) and in SA50Slef complex PDB ID: 5HL7 (orange), revealing the movements of nucleotide U2585 in the bound vs. native structure.

FIG. 18 presents a graphic illustration of an overlay of the PTC in complex structure SA50SBC-3205 (magenta) and in complex structure SA50Slef (orange).

As can be seen in FIG. 16, in the SA50Slef complex crystal structure, lefamulin was found to be bound at the PTC, so that its tricyclic mutilin core is blocking the A-site, and its C14 extension is pointing into the P-site, thus perturbing A- and P-site tRNA accommodation, as was found in the ribosome-pleuromutilin complexes with D50S and SA50S.

As can further be seen in FIGS. 16-18, as all pleuromutilins are assumed to bind to the same pocket, a hydrogen bond is formed between the drug's acetyl carbonyl and the NH₂ of G2061. In the SA50Slef complex, the conformation of the flexible nucleotide U2585 is different from that of the unbound SA50S and of the SA50SBC-3205 complex. Interactions with the rRNA nucleotides C2063, U2506, A2503, U2504, G2505, A2453, C2452, A2425 and C2424 are either hydrophobic or based on van der Waals forces.

FIG. 19 presents a graphic illustration of the ribosomal binding pocket of lefamulin, as seen in the complex crystal structure SA50Slef, showing that the ligand is held within the PTC by a net of hydrogen bonds with the 23S rRNA, wherein the U-U interactions between U2585 and U2506 stabilizes the lefamulin binding pocket (the electron density of lefamulin is weighted $2F_o$-$F_c$ contoured at 1.0 σ).

As can be seen in FIG. 19, in the SA50Slef complex, U2585 conformational range is reduced because of a stacking interaction with the C14 extension of lefamulin. This interaction is stabilized by a U-U-4-carbonyl N3 symmetric interactions between U2585 and U2506, which is shifted towards the binding pocket. Another hydrogen bond is formed between NH2 group of the lefamulin C14 extension and the O2 of A2062 ribose.

FIGS. 20A-B present the results of in vitro transcription-translation cell-free inhibition assays of bacterial protein synthesis, wherein the inhibitory effect on protein expression in *S. aureus* system of BC-3205 is presented in FIG. 20A and of lefamulin is presented in FIG. 20B. The activity of the reporter protein (luciferase) in the presence of various concentrations of BC-3205 and lefamulin is shown as arbitrary unit of luminescence [a.u.]. The IC50 values calculated by the plotted data showed better inhibition of lefamulin than BC-3205 on protein synthesis.

As can be reckoned from the results, lefamulin has a single additional interaction with the PTC 23S rRNA nucleotides compared to BC-3205 (with A2062) and its U2585 and U2506 U-U interactions stabilize the lefamulin binding pocket. Compared to other pleuromutilins, it makes two additional hydrogen bonds. This might be the reason for lefamulin prior potency over BC-3205 in *S. aureus* cell free in vitro transcription-translation assay; IC50=0.09 μg/ml of lefamulin comparing to $IC_{50}$ 0.42 μg/ml of BC-3205 (see, FIGS. 20A-B).

Following the rationale for novel species-specific protein synthesis inhibitors, such as presented in Example 8 hereinabove, the SA50Slef complex structure may contribute structural data pertaining to spatial positioning of moieties in the lefamulin molecule, that interact with various ribosomal moieties, and particularly lefamulin moieties that interact with ribosomal moieties that differ structurally and chemically across species. One non-limiting example of such a moiety is 2-((4-amino-2-hydroxycyclohexyl)thio)acetyl:

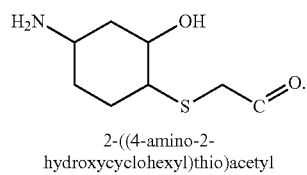

2-((4-amino-2-hydroxycyclohexyl)thio)acetyl

Example 10

The Complex Crystal Structure of SA50S with Lincosamides

Lincosamides are known to inhibit the peptidyl transferase reaction taking place in the ribosome during transcription-translation. Lincomycin, a member of the lincosamides family of antibacterial drugs, is a naturally occurring compound that is produced by the bacteria *Streptomyces lincolnensis*. It is a narrow-spectrum antibiotic agent and targets primarily Gram-positive bacteria, including pathogenic Streptococci, Staphylococci, *Mycoplasma*, anaerobic bacteria, most anaerobic bacteria such as *Bacteroides fragilis*, and some protozoa. Lincomycin is used to treat severe bacterial infections in people who cannot tolerate penicillin-type antibiotics. It shows weak activity against most Gram-negative bacteria.

Clindamycin, a semi-synthetic lincosamide antibiotic agent. Lincomycin structure is similar to clindamycin, except for its 7-hydroxy group, which is a chlorine atom in clindamycin. Clindamycin has largely replaced lincomycin due to an improved side effect profile, and due to its higher potency against Gram-negative bacteria. This is in part due to the higher lipid solubility of clindamycin that enables it to permeate the outer membrane of the target bacteria.

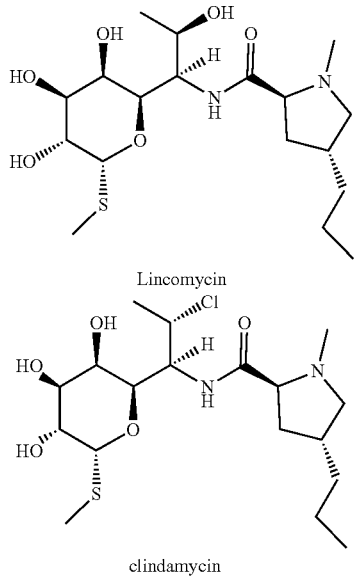

Lincomycin clindamycin

Shortly after the introduction of erythromycin in therapy in the 1950s, resistance to the drug was observed in bacterial pathogens. More disquieting was the observation that *Staphylococcus aureus* erythromycin-resistant strains were cross-resistant not only to all other macrolides but also to the chemically unrelated lincosamide and streptogramin B drugs. This phenomenon was termed the macrolide-lincosamide-streptogramin B ($MLS_B$) antibiotic resistance phenotype and was found to be caused by to expression of a methyltransferase enzyme, ermC. This enzyme methylates 23S rRNA at the N-6 position of adenosine A2058 (*Escherichia coli* numbering throughout), which is a pivotal nucleotide for the binding of $MLS_B$ antibiotics. Later, an additional methyltransferase enzyme, encoded by the Cfr gene, was found to cause multidrug resistance in *S. aureus* to phenicols, lincosamides, oxazolidinones, pleuromutilins, and streptogramin A (PhLOPSA) by methylation of the C8 position of the 23S rRNA nucleotide A2503. Even though resistance in bacteria with multiple rrn operons, such as *Staphylococcus* species, is generally conferred by rRNA modifications such as these methylations, several mutations are rRNA and rProteins were identified in *S. aureus*.

The A2058G, A2058U mutations in the 23S rRNA were associated with $MLS_B$ resistance, similar to those already reported for other organisms. A2059G mutation is associated with macrolide-lincosamide resistance; however the insusceptibility to lincosamides seemed to be moderate as previously reported for *Helicobacter pylori* and *Streptococcus pneumoniae*. Cross-resistance to chloramphenicol, linezolid, and streptogramin A, of which the binding pockets partially overlap, is associated with the second shell nucleotide G2576U mutation. In addition, cross-resistance of *S. aureus* to chloramphenicol and linezolid may be caused by G2505A and U2500A mutations. The mutation K68Q in the rProtein uL4 in *S. aureus* causes resistance to chloramphenicol, linezolid, pleuromutilins, and tedizolid. This residue (68) has been identified in the *S. aureus* crystal structure provided herewith, and found to be in proximity to the mentioned above A2058 and A2059.

To obtain SA50S-lincomycin complex (SA50Slinc), SA50S crystals, provided as described hereinabove, were soaked in solutions containing 22 μg/ml lincomycin in the stabilization solution for 6 hours prior to flash freezing and data collection. The crystal structures of the large ribosomal subunit from *S. aureus*, complexed with lincomycin (SA50Slinc; PDB ID: 5HKV) was determined according to the procedure described above. The crystallographic results are summarized in Table 7 below (in parentheses are the values for the highest resolution shells of 5HKV (3.70-3.64).

TABLE 7

| Subject | SA50Slinc |
| --- | --- |
| Space group | $P6_522$ |
| A = b [Å] | 280.8 |
| c [Å] | 873.5 |
| α, β, γ [°] | 90, 90, 120 |
| Complex with | lincomycin |
| X-ray source | ID29, ID23-1 |
| Wavelength [Å] | 0.971 |
| Number of crystals | 30 |
| Resolution [Å] | 50-3.64 (3.70-3.64) |
| Unique reflections | 2230088 |
| Observed reflections | 223602 |
| Redundancy | 10.0 (4.4) |
| Completeness [%] | 98.0 (78.1) |
| <I>/<σ> | 9.08 (1.37) |
| R-merge [%] | 23.7 (97.2) |
| Refinement | |
| R-factor [%] | 18.74 |
| R-free (5%) [%] | 23.40 |
| RMSD bonds [Å] | 0.009 |
| RMSD angles [°] | 1.438 |

FIG. 21 presents a graphic illustration of the electron density map (weighted 2Fo-Fc contoured at 1.0 σ) attributed to a molecule of lincomycin as seen in the crystal structure of the antibiotic agent complexed with SA50S (PDB ID: 5HKV).

FIG. 22 presents a graphic illustration showing a structural superposition of the two lincosamides in their common binding site, wherein the structure of the bound lincomycin is derived from SA50Slinc PDB ID: 5HKV (presented in pink) and structure of the bound clindamycin is derived independently from PDB ID: 1JZX disclosing *D. radiodurans*-lincomycin complex (D50S-CLY, presented in grey), PDB ID: 1YJN disclosing *H. marismortui*-lincomycin complex (H50S-CLY, presented in sky-blue), and PDB: ID 3OFZ disclosing *E. coli*-lincomycin complex (E70-CLY, presented in green).

As can be seen in FIG. 22, the pyrrolidinyl propyl group of the two lincosamides is positioned at the PTC and interferes with A-site tRNA positioning while their lincosamine moieties point towards the nascent chain exit tunnel.

FIGS. 23A-B present a graphical illustration of the binding pocket of lincomycin in SA50S, wherein FIG. 23A shows lincomycin (presented in pink) interacts with the PTC A-site by numerous hydrogens bond (dashed line) with the 23S rRNA (presented in grey), and FIG. 23B is a 90 degrees horizontal rotated view of FIG. 23A.

The available crystal structures indicate that the two lincosamides exhibit four hydrogen bonds with the 23S rRNA nucleotides surroundings 4): (1) O2 group of the lincosamine forms a hydrogen bond with N4 of C2611; (2) O3 group of the lincosamine forms a hydrogen bond with N6 of A2058; (3) O4 group of the lincosamine forms hydrogen bond with O2 of A2503's sugar; and (4) The bridging amine (NH) of lincomycin creates hydrogen bond to the ribose O4 of G2505. The lincomycin's and clindamycin's (H50S-CLY and E70S-CLY structures) O2, O3 and O4 groups are also involved in hydrogen bonding with N1 of A2058, N6 of A2059 and OP1 of G2505, respectively. Other interactions of lincomycin with the rRNA nucleotides U2504, C2452, A2451, G2061 and U2506 are either hydrophobic interactions or van der Waals force interactions.

FIG. 24 present a graphical illustration of a structural superposition of the PTC in native SA50S (presented in teal) and in SA50S-lincomycin complex (presented in pink), showing a difference in the position of nucleotide A2062 in the SA50Slinc towards the spermidine (SPD) compared to the native structure.

Comparisons of the SA50Slinc, D50S-CLY, H50S-CLY and E70S-CLY complex structures show that nucleotide A2062 has different orientations. In *S. aureus, E. coli* and *D. radiodurans* the orientations are only slightly different, whereas in *H. marismortui* this nucleotide is shifted towards clindamycin, so that N6 of A2062 forms a hydrogen bond with the carbonyl of the clindamycin. In SA50Slinc electron density map an additional electron density was observed between the lincomycin and nucleotide A2062 that can accommodate a molecule of spermidine (an additive of the crystallization conditions). This spermidine interacts with the 7-hydroxy group of the lincomycin and with A2062 thus stabilizes A2062 in its place which is slightly different from the non-bound structure (SA50S). The interaction with A2062 does not occur with clindamycin since it contains a chlorine atom instead of the 7-hydroxy group.

U2504 and U2506 are in a similar position in SA50Slinc and E70S-CLY but differ from D50S-CLY and H50S-CLY. A2503 in D50S-CLY is flipped by 180 degrees from its position in the other structures. In SA50Slinc U2585 nucleobase could not be placed in the electron density map due to its flexibility while in the SA50S complexed with clindamycin and in SA50S it has a slightly different orientation (see, FIGS. 23A-B).

In D50S-CLY the clindamycin is positioned somewhat different, so that its pyrrodinyl propyl tail is pointing 102 degrees away from its position in the other available structures.

As can be concluded from the data and structural analysis of SA50Slinc the other available structures of 50S-lincomycin complex, lincosamines bind at the same binding pocket in the large ribosomal subunit. It appears that in the studied organisms, the lincosamide sugar has similar H-bond interactions with the 23S nucleotides. This sugar moiety may be the main determinant for targeting the lincosamines to the ribosome. The structural data presented herein shows that by replacing the moiety that is attached to the sugar moiety, binding and inhibition can still be achieved mainly through this moiety.

It is also seen that lincomycin complex with SA50S accommodates a spermidine in the binding pocket. This spermidine, a polyamine, interacts with the 7-hydroxyl of the lincomycin and with A2062. Under physiological conditions this spermidine can be replaced by an ion, which tightens the lincomycin pocket. In the complex H50S-CLY A2062 N6 forms hydrogen bond with the carbonyl, but in the D50S-CLY and E70S-CLY there is no hydrogen bond between this nucleotide and clindamycin. It seems that the interaction with A2062 improves the drug binding properties as lincomycin has a super low $IC_{50}$ against *S. aureus* ribosome compared to *E. coli* ones (available data no shown).

The Crystallographic data indicate that the interactions of the 4-propyl-2-pyrrolidinyl ring of the lincosamide antibiotics lincomycin and clindamaycin with the 23S nucleotides are based essentially on van der Waals forces. This data may indicate that the contribution of the 4-propyl-2-pyrrolidinyl moiety is small, yet, this moiety affects the pharmacokinetic properties of lincosamides and its overall protein translation inhibition properties.

As lincosamines bind at the tRNA A-site and at the entrance to the exit tunnel so that the lincosamine sugar moiety overlaps with the site occupied by the desosamine sugar of macrolides, the cross-resistance between lincosamines and the macrolides may be explained thereby. From the comparison with the macrolide it may be rationalized why the sugar moiety of the lincosamides alone does not inhibit protein synthesis (available data no shown).

Following the rationale for novel species-specific protein synthesis inhibitors, such as presented in Example 8 hereinabove, the SA50Slef complex structure may contribute structural data pertaining to spatial positioning of moieties in the lincomycin molecule, that interact with various ribosomal moieties, and particularly lincomycin moieties that interact with ribosomal moieties that differ structurally and chemically across species. Non-limiting example of such moieties include lincosamine and 4-propyl-2-pyrrolidinyl moieties.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method producing a ligand having an affinity to a binding site of a large ribosomal subunit of a pathogenic bacterium, the method comprising:
   (a) obtaining positioning data indicative of atomic coordinates of at least one binding site determined from an electron density map having a resolution of at least 4 Å calculated from X-rays diffraction data obtained using at least one of a composition-of-matter that comprises a crystallized *Staphylococcus aureus* 50S large ribosomal subunit, wherein the crystallized 50S large ribosomal subunit effectively diffracts X-rays for calculating an electron density map and determination of atomic coordinates to a resolution of at least 4 Å and forms in a hexagonal space group with unit cell dimensions of a=279.6±10 Å, b=279.6±10 Å, c=872.7±10 Å, α=90, β=90, γ=120;
   (b) calculating a molecular surface of the binding site;
   (c) computationally constructing a model of a chemically feasible ligand having a molecular surface that match the molecular surface of the binding site; and
   synthesizing the ligand based on said model.

2. The method of claim 1, wherein said *Staphylococcus aureus* is capable of developing a resistance to an antibacterial agent.

3. The method of claim 2, wherein said *Staphylococcus aureus* is selected from the group consisting of a methicillin-resistant *Staphylococcus aureus* (MRSA), an oxacillin-resistant *Staphylococcus aureus* (ORSA), a vancomycin-resistant *Staphylococcus aureus* (VRSA) and a vancomycin intermediate *Staphylococcus aureus* (VISA).

4. The method of claim 2, characterized by the atomic coordinates deposited at the Protein Data Bank under accession number PDB ID: 4WCE.

5. The method of claim 1, wherein a ligand is bound to said large ribosomal subunit to form a crystallized complex of the subunit and said ligand.

6. The method of claim 5, wherein said ligand is selected from the group consisting of linezolid, BC-3205, telithromycin, lefamulin and lincomycin.

7. The method of claim 6, wherein said ligand is linezolid and the composition is characterized by the atomic coordinates deposited at the Protein Data Bank under accession number PDB ID: 4WFA.

8. The method of claim 6, wherein said ligand is BC-3205 and the composition is characterized by the atomic coordinates deposited at the Protein Data Bank under accession number PDB ID: 4WFB.

9. The method of claim 6, wherein said ligand is telithromycin and lincomycin and the composition is characterized by the atomic coordinates deposited at the Protein Data Bank under accession number PDB ID: 4WF9.

10. The method of claim 6, wherein said ligand is lefamulin and the composition is characterized by the atomic coordinates deposited at the Protein Data Bank under accession number PDB ID: 5HL7.

11. The method of claim 6, wherein said ligand is lincomycin and the composition is characterized by the atomic coordinates deposited at the Protein Data Bank under accession number PDB ID: 5HKV.

12. The method of claim 1, further comprising, prior to step (c): computationally constructing a library of structures of chemically feasible ligands having a molecular surface that matches the molecular surface of the binding site.

13. The method of claim 12, further comprising:
    (d) computationally determining a matching score for each of said ligands; and
    (e) based on said matching score selecting at least one putative ligand having the desired affinity to the binding site of the large ribosomal subunit of a pathogenic bacterium.

14. The method of claim 13, further comprising, prior to step (d), adding to said library a plurality of structures of chemically feasible variants of pre-existing ligands.

15. The method of claim 1, further comprising, prior to step (c), calculating a molecular surface of at least a portion of the binding site of a large ribosomal subunit of a different organism.

16. The method of claim 15, wherein said different organism is selected from the group consisting of a host of the pathogenic bacterium and a benign microorganism.

17. The method of claim 16, wherein step (c) comprises computationally constructing a chemically feasible ligand having a molecular surface that matches the molecular surface of the binding site of the large ribosomal subunit of a pathogenic bacterium, and mismatches at least one feature in said molecular surface of the binding site in said of a large ribosomal subunit of said different organism.

18. The method of claim 1, wherein the binding site is selected from the group consisting of a inter-subunit interface, a peptidyl transferase site, a GTPase center, an mRNA binding site, an A-site, a P-site, an E-site, a polypeptide exit tunnel, a translation initiation factor (IF1) binding site, a translation initiation factor (IF2) binding site, a translation initiation factor (IF3) binding site, an elongation factor G (EF-G) binding site, elongation factor Tu (EF-Tu) binding site, hibernation factor HPF binding site, hibernation factor RMF binding site, hibernation factor YfiA binding site, a GTP binding site and a ricin binding site.

19. The method of claim 1, wherein the ligand has a molecular weight of less than 1,500 g/mol.

\* \* \* \* \*

SEQUENCE LISTING

<160> NUMBER OF SEQ ID NOS: 28

<210> SEQ ID NO 1
<211> LENGTH: 2923
<212> TYPE: RNA
<213> ORGANISM: STAPHYLOCOCCUS AUREUS
<220> FEATURE:
<221> NAME/KEY: misc_feature
<223> OTHER INFORMATION: 23S RRNA; CHAIN: X

<400> SEQUENCE: 1

```
gauuaaguua uuaagggcgc acgguggaug ccuuggcacu agaagccaau gaaggacguu      60
acuaacgacg auaugcuuug gggagcugua aguaagcuuu gauccagaga uuuccgaaug     120
gggaaaccca gcaugaguua ugucauguua ucgauaugug aauacauagc auaucagaag     180
gcacacccgg agaacugaaa caucuuagua cccggaggaa gagaaagaaa auucgauucc     240
cuuaguagcg gcgagcgaaa cgggaagagc ccaaaccaac aagcuugcuu guuggguug     300 uaggacacuc uauacggagu uacaaaggac gacauuagac gaaucaucug gaaagaugaa     360
ucaaagaagg uaauaauccu guagucgaaa auguugcuc ucuugagugg auccugagua     420
cgacggagca cgugaaauuc cgucggaauc ugggaggacc aucccuaag gcuaaauacu     480 cucuagugac cgauagugaa ccaguaccgu gagggaaagg ugaaaagcac cccggaaggg     540
gagugaaaua gaaccugaaa ccgugugcuu acaaguaguc agagcccguu aaugggugau     600
ggcgugccuu uuguagaaug aaccggcgag uuacgauuug augcaagguu aagcaguaaa     660
uguggagccg uagcgaaagc gagucugaau aggcguuua guauugguc guagacccga     720 aaccagguga ucuaccuug gucagguuga aguucaggua acacugaaug gaggaccgaa     780
ccgacuuacg uugaaaagug agcggaugaa cugagguag cggagaaauu ccaaucgaac     840
cuggagauag cugguucucu ccgaaauagc uuuagggcua ccucaagug augauuauug     900 gagguagagc acuguuugga cgaggggccc cucucgggu accgaauuca dacaaacucc     960
gaaugccaau uaauuaacu ugggagucag aacaugggug auaaggugcg uguucgaaag    1020
ggaaacagcc cagaccacca gcuaaggucc caaauauau guuaagugga aaggaugug    1080 gcguugccca gacaacuagg auguuggcuu agaagcagcc aucauuuaaa gagugcguaa    1140
uagcucacua gucgagugac acugcgccga aaauguaccg gggcuaaaca uauuaccgaa    1200
gcuguggauu guccuuugga caauggguagg agagcguucu aagggcguug aagcaugauc    1260
guaaggacau guggagcgcu agaagugag aauggccggug ugaguagcga agacggguug    1320
agaaucccgu ccaccgauug acuaagguu ccagaggaag gcucguccgc ucuggguuag    1380
ucggguccua agcugaggcc gacaggcgua ggcgauggau aacaguugga uauccugua    1440 ccaccuauaa ucguuuuaau cgauggggg acgcaguagg auaggcgaag cgugcgauug    1500
gauugcacgu cuaagcagua aggcugagua uuaggcaaau ccggacucg uuaggcuga    1560 gcugugaugg ggagaagaca uugagucuuc gagucguuga uuucacacug ccagaaaag    1620 ccucuagaua gaaaauaggu gcccguaccg caaaccgaca cagguaguca agaugagaau    1680
ucuaagguga gcgagcgaac ucucguuaag gaacucggca aaaugacccc guaacuucgg    1740 gagaagggu gcucuuuagg guuaacgccc agaagagccg caguaauag gcccaagcga    1800 cuguuuauca aaaacacagg ucucugcuaa accguaaggu gauguauagg ggcugacgcc    1860
```

-continued

```
ugcccggugc uggaagguua agaggagugg uuagcuucug cgaagcuacg aaucgaagcc    1920
ccaguaaacg gcggccguaa cuauaacggu ccuaagguag cgaaauuccu ugucggguaa    1980
guuccgaccc gcacgaaagg cguaacgauu ugggcacugu cucaacgaga gacucgguga    2040
aaucauagua ccugugaaga ugcagguuac ccgcgacagg acggaaagac cccgugGagc    2100
uuuacuguag ccugauauug aaauucggca cagcuuguac aggauaggua ggagccuuug    2160
aaacgugagc gcuagcuuac guggaggcgc uggugggaua cacccuagc uguguuggcu     2220 uucuaacccg caccacuuau cguggUggga gacaguguca agcgggcagu ugacugggg     2280 cggucgccuc cuaaaaggua acggaggcgc ucaaaaguuc ccucagaaug guuggaaauc    2340
auucauagag uguaaaggca uaagggagcu ugacugcgag accacaagu cgagcagggu     2400 cgaaagacgg acuuagugau ccggugguuc cgcauggaag ggccaucgcu caacggauaa    2460
aagcuacccc ggggauaaca ggcuuaucuc ccccaagagu ucacaucgac ggggaggaggyuu 2520 ggcaccucga gucggcuca ucgcauccug gggcuguagu cggucccaag gguugggcug     2580
uucgcccauu aaagcgguac gcgagcuggg uucagaacgu cgugagacag uucggucccu    2640
auccgucgug ggcguaggaa auuugagagg agcugucuu aguacgagag gaccgggaug    2700
gacauaccuc uggugacc guugucgugc caacggcaua gcugggguagc uaugugugga     2760 cgggauaagu gcugaaagca ucuaagcaug aagcccccu caagaugaga uuuccсcaацu    2820 ucgguuauaa gaucccucaa agaugaugag guuaauaggu ucgaggugga agcaugguga    2880 caugguggagc ugacgaauac uaaucgaucg aagacuuaau caa                      2923
```

<210> SEQ ID NO 2
<211> LENGTH: 114
<212> TYPE: RNA
<213> ORGANISM: STAPHYLOCOCCUS AUREUS
<220> FEATURE:
<221> NAME/KEY: misc_feature
<223> OTHER INFORMATION: 5S RRNA; CHAIN: Y

<400> SEQUENCE: 2

```
ucuggugacu auagcaagga ggucacaccu guucccaugc cgaacacaga aguuaagguc    60
uuuagcgacg augguagcca acuuacguuc cgcuagagua gaacguugcc aggc         114
```

<210> SEQ ID NO 3
<211> LENGTH: 277
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L2; CHAIN: A

<400> SEQUENCE: 3

```
Met Ala Ile Lys Lys Tyr Lys Pro Ile Thr Asn Gly Arg Arg Asn Met
1               5                   10                  15

Thr Ser Leu Asp Phe Ala Glu Ile Thr Lys Thr Thr Pro Glu Lys Ser
            20                  25                  30

Leu Leu Lys Pro Leu Pro Lys Lys Ala Gly Arg Asn Asn Gln Gly Lys
        35                  40                  45

Leu Thr Val Arg His His Gly Gly Gly His Lys Arg Gln Tyr Arg Val
    50                  55                  60

Ile Asp Phe Lys Arg Asn Lys Asp Gly Ile Asn Ala Lys Val Asp Ser
65                  70                  75                  80

Ile Gln Tyr Asp Pro Asn Arg Ser Ala Asn Ile Ala Leu Val Val Tyr
```

```
                        85                  90                  95
Ala Asp Gly Glu Lys Arg Tyr Ile Ile Ala Pro Lys Gly Leu Glu Val
                100                 105                 110

Gly Gln Ile Val Glu Ser Gly Ala Glu Ala Asp Ile Lys Val Gly Asn
            115                 120                 125

Ala Leu Pro Leu Gln Asn Ile Pro Val Gly Thr Val Val His Asn Ile
        130                 135                 140

Glu Leu Lys Pro Gly Lys Gly Gln Ile Ala Arg Ser Ala Gly Ala
145                 150                 155                 160

Ser Ala Gln Val Leu Gly Lys Glu Gly Lys Tyr Val Leu Ile Arg Leu
                165                 170                 175

Arg Ser Gly Glu Val Arg Met Ile Leu Ser Thr Cys Arg Ala Thr Ile
                180                 185                 190

Gly Gln Val Gly Asn Leu Gln His Glu Leu Val Asn Val Gly Lys Ala
            195                 200                 205

Gly Arg Ser Arg Trp Lys Gly Ile Arg Pro Thr Val Arg Gly Ser Val
        210                 215                 220

Met Asn Pro Asn Asp His Pro His Gly Gly Gly Glu Gly Arg Ala Pro
225                 230                 235                 240

Ile Gly Arg Pro Ser Pro Met Ser Pro Trp Gly Lys Pro Thr Leu Gly
                245                 250                 255

Lys Lys Thr Arg Arg Gly Lys Lys Ser Ser Asp Lys Leu Ile Val Arg
                260                 265                 270

Gly Arg Lys Lys Lys
            275

<210> SEQ ID NO 4
<211> LENGTH: 220
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L3; CHAIN: B

<400> SEQUENCE: 4

Met Thr Lys Gly Ile Leu Gly Arg Lys Ile Gly Met Thr Gln Val Phe
1               5                   10                  15

Gly Glu Asn Gly Glu Leu Ile Pro Val Thr Val Glu Ala Lys Glu
            20                  25                  30

Asn Val Val Leu Gln Lys Lys Thr Val Glu Val Asp Gly Tyr Asn Ala
            35                  40                  45

Ile Gln Val Gly Phe Glu Asp Lys Lys Ala Tyr Lys Lys Asp Ala Lys
        50                  55                  60

Ser Asn Lys Tyr Ala Asn Lys Pro Ala Glu Gly His Ala Lys Lys Ala
65                  70                  75                  80

Asp Ala Ala Pro Lys Arg Phe Ile Arg Glu Phe Arg Asn Val Asp Val
                85                  90                  95

Asp Ala Tyr Glu Val Gly Gln Glu Val Ser Val Asp Thr Phe Val Ala
                100                 105                 110

Gly Asp Val Ile Asp Val Thr Gly Val Ser Lys Gly Lys Gly Phe Gln
            115                 120                 125

Gly Ala Ile Lys Arg His Gly Gln Ser Arg Gly Pro Met Ser His Gly
        130                 135                 140

Ser His Phe His Arg Ala Pro Gly Ser Val Gly Met Ala Ser Asp Ala
145                 150                 155                 160
```

```
Ser Arg Val Phe Lys Gly Gln Lys Met Pro Gly Arg Met Gly Gly Asn
                165                 170                 175

Thr Val Thr Val Gln Asn Leu Glu Val Val Gln Val Asp Thr Glu Asn
            180                 185                 190

Lys Val Ile Leu Val Lys Gly Asn Val Pro Gly Pro Lys Lys Gly Leu
        195                 200                 205

Val Glu Ile Arg Thr Ser Ile Lys Lys Gly Asn Lys
    210                 215                 220

<210> SEQ ID NO 5
<211> LENGTH: 207
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L4; CHAIN: C

<400> SEQUENCE: 5

Met Ala Asn Tyr Asp Val Leu Lys Leu Asp Gly Thr Lys Ser Gly Ser
1               5                   10                  15

Ile Glu Leu Ser Asp Ala Val Phe Gly Ile Glu Pro Asn Asn Ser Val
            20                  25                  30

Leu Phe Glu Ala Ile Asn Leu Gln Arg Ala Ser Leu Arg Gln Gly Thr
        35                  40                  45

His Ala Val Lys Asn Arg Ser Ala Val Ser Gly Gly Arg Lys Pro
    50                  55                  60

Trp Lys Gln Lys Gly Thr Gly Arg Ala Arg Gln Gly Thr Ile Arg Ala
65                  70                  75                  80

Pro Gln Trp Arg Gly Gly Ile Val Phe Gly Pro Thr Pro Arg Ser
                85                  90                  95

Tyr Ala Tyr Lys Met Pro Lys Lys Met Arg Arg Leu Ala Leu Arg Ser
                100                 105                 110

Ala Leu Ser Phe Lys Ala Gln Glu Asn Gly Leu Thr Val Val Asp Ala
            115                 120                 125

Phe Asn Phe Glu Ala Pro Lys Thr Lys Glu Phe Lys Asn Val Leu Ser
130                 135                 140

Thr Leu Glu Gln Pro Lys Lys Val Leu Val Val Thr Glu Asn Glu Asp
145                 150                 155                 160

Val Asn Val Glu Leu Ser Ala Arg Asn Ile Pro Gly Val Gln Val Thr
                165                 170                 175

Thr Ala Gln Gly Leu Asn Val Leu Asp Ile Thr Asn Ala Asp Ser Leu
            180                 185                 190

Val Ile Thr Glu Ala Ala Ala Lys Lys Val Glu Glu Val Leu Gly
        195                 200                 205

<210> SEQ ID NO 6
<211> LENGTH: 179
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L5; CHAIN: D

<400> SEQUENCE: 6

Met Asn Arg Leu Lys Glu Lys Phe Asn Thr Glu Val Thr Glu Asn Leu
1               5                   10                  15

Met Lys Lys Phe Asn Tyr Ser Ser Val Met Glu Val Pro Lys Ile Asp
            20                  25                  30
```

```
Lys Ile Val Val Asn Met Gly Val Gly Asp Ala Val Gln Asn Ser Lys
             35                  40                  45

Val Leu Asp Asn Ala Val Glu Glu Leu Glu Leu Ile Thr Gly Gln Lys
 50                  55                  60

Pro Leu Val Thr Lys Ala Lys Lys Ser Ile Ala Thr Phe Arg Leu Arg
 65                  70                  75                  80

Glu Gly Met Pro Ile Gly Ala Lys Val Thr Leu Arg Gly Glu Arg Met
                 85                  90                  95

Tyr Glu Phe Leu Asp Lys Leu Ile Ser Val Ser Leu Pro Arg Val Arg
                100                 105                 110

Asp Phe Gln Gly Val Ser Lys Lys Ala Phe Asp Gly Arg Gly Asn Tyr
                115                 120                 125

Thr Leu Gly Val Lys Glu Gln Leu Ile Phe Pro Glu Ile Asp Tyr Asp
            130                 135                 140

Lys Val Ser Lys Val Arg Gly Met Asp Ile Val Ile Val Thr Thr Ala
145                 150                 155                 160

Asn Thr Asp Glu Glu Ala Arg Glu Leu Leu Ala Asn Phe Gly Met Pro
                    165                 170                 175

Phe Arg Lys

<210> SEQ ID NO 7
<211> LENGTH: 178
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L6; CHAIN: E

<400> SEQUENCE: 7

Met Ser Arg Val Gly Lys Lys Ile Ile Asp Ile Pro Ser Asp Val Thr
 1               5                  10                  15

Val Thr Phe Asp Gly Asn His Val Thr Val Lys Gly Pro Lys Gly Glu
             20                  25                  30

Leu Ser Arg Thr Leu Asn Glu Arg Met Thr Phe Lys Gln Glu Glu Asn
             35                  40                  45

Thr Ile Glu Val Val Arg Pro Ser Asp Ser Lys Glu Asp Arg Thr Asn
 50                  55                  60

His Gly Thr Thr Arg Ala Leu Leu Asn Asn Met Val Gln Gly Val Ser
 65                  70                  75                  80

Gln Gly Tyr Val Lys Val Leu Glu Leu Val Gly Val Gly Tyr Arg Ala
                 85                  90                  95

Gln Met Gln Gly Lys Asp Leu Ile Leu Asn Val Gly Tyr Ser His Pro
                100                 105                 110

Val Glu Ile Lys Ala Glu Glu Asn Ile Thr Phe Ser Val Glu Lys Asn
                115                 120                 125

Thr Val Val Lys Val Glu Gly Ile Ser Lys Glu Gln Val Gly Ala Leu
            130                 135                 140

Ala Ser Asn Ile Arg Ser Val Arg Pro Pro Glu Pro Tyr Lys Gly Lys
145                 150                 155                 160

Gly Ile Arg Tyr Gln Gly Glu Tyr Val Arg Arg Lys Glu Gly Lys Thr
                    165                 170                 175

Gly Lys

<210> SEQ ID NO 8
<211> LENGTH: 145
<212> TYPE: PRT
```

<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L13; CHAIN: G

<400> SEQUENCE: 8

Met Arg Gln Thr Phe Met Ala Asn Glu Ser Asn Ile Glu Arg Lys Trp
1               5                   10                  15

Tyr Val Ile Asp Ala Glu Gly Gln Thr Leu Gly Arg Leu Ser Ser Glu
            20                  25                  30

Val Ala Ser Ile Leu Arg Gly Lys Asn Lys Val Thr Tyr Thr Pro His
        35                  40                  45

Val Asp Thr Gly Asp Tyr Val Ile Val Ile Asn Ala Ser Lys Ile Glu
    50                  55                  60

Phe Thr Gly Asn Lys Glu Thr Asp Lys Val Tyr Tyr Arg His Ser Asn
65                  70                  75                  80

His Pro Gly Gly Ile Lys Ser Ile Thr Ala Gly Glu Leu Arg Arg Thr
                85                  90                  95

Asn Pro Glu Arg Leu Ile Glu Asn Ser Ile Lys Gly Met Leu Pro Ser
            100                 105                 110

Thr Arg Leu Gly Glu Lys Gln Gly Lys Lys Leu Phe Val Tyr Gly Gly
        115                 120                 125

Ala Glu His Pro His Ala Ala Gln Gln Pro Glu Asn Tyr Glu Leu Arg
    130                 135                 140

Gly
145

<210> SEQ ID NO 9
<211> LENGTH: 122
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L14; CHAIN: H

<400> SEQUENCE: 9

Met Ile Gln Gln Glu Thr Arg Leu Lys Val Ala Asp Asn Ser Gly Ala
1               5                   10                  15

Arg Glu Val Leu Thr Ile Lys Val Leu Gly Gly Ser Gly Arg Lys Thr
            20                  25                  30

Ala Asn Ile Gly Asp Val Ile Val Cys Thr Val Lys Asn Ala Thr Pro
        35                  40                  45

Gly Gly Val Val Lys Lys Gly Asp Val Val Lys Ala Val Ile Val Arg
    50                  55                  60

Thr Lys Ser Gly Val Arg Arg Asn Asp Gly Ser Tyr Ile Lys Phe Asp
65                  70                  75                  80

Glu Asn Ala Cys Val Ile Ile Arg Asp Asp Lys Gly Pro Arg Gly Thr
                85                  90                  95

Arg Ile Phe Gly Pro Val Ala Arg Glu Leu Arg Glu Gly Asn Phe Met
            100                 105                 110

Lys Ile Val Ser Leu Ala Pro Glu Val Leu
        115                 120

<210> SEQ ID NO 10
<211> LENGTH: 146
<212> TYPE: PRT
<213> ORGANISM: STAPHYLOCOCCUS AUREUS
<220> FEATURE:
<221> NAME/KEY: MISC_FEATURE

<223> OTHER INFORMATION: 50S RIBOSOMAL PROTEIN L15; CHAIN: I

<400> SEQUENCE: 10

```
Met Lys Leu His Glu Leu Lys Pro Ala Glu Gly Ser Arg Lys Glu Arg
1               5                   10                  15

Asn Arg Val Gly Arg Gly Val Ala Thr Gly Asn Gly Lys Thr Ser Gly
            20                  25                  30

Arg Gly His Lys Gly Gln Lys Ala Arg Ser Gly Gly Gly Val Arg Pro
        35                  40                  45

Gly Phe Glu Gly Gly Gln Leu Pro Leu Phe Arg Arg Leu Pro Lys Arg
    50                  55                  60

Gly Phe Thr Asn Ile Asn Arg Lys Glu Tyr Ala Ile Val Asn Leu Asp
65                  70                  75                  80

Gln Leu Asn Lys Phe Glu Asp Gly Thr Glu Val Thr Pro Ala Leu Leu
                85                  90                  95

Val Glu Ser Gly Val Val Lys Asn Glu Lys Ser Gly Ile Lys Ile Leu
            100                 105                 110

Gly Asn Gly Ser Leu Asp Lys Lys Leu Thr Val Lys Ala His Lys Phe
        115                 120                 125

Ser Ala Ser Ala Ala Glu Ala Ile Asp Ala Lys Gly Gly Ala His Glu
    130                 135                 140

Val Ile
145
```

<210> SEQ ID NO 11
<211> LENGTH: 144
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L16; CHAIN: J

<400> SEQUENCE: 11

```
Met Leu Leu Pro Lys Arg Val Lys Tyr Arg Arg Gln His Arg Pro Lys
1               5                   10                  15

Thr Thr Gly Arg Ser Lys Gly Gly Asn Tyr Val Thr Phe Gly Glu Phe
            20                  25                  30

Gly Leu Gln Ala Thr Thr Thr Ser Trp Ile Thr Ser Arg Gln Ile Glu
        35                  40                  45

Ser Ala Arg Ile Ala Met Thr Arg Tyr Met Lys Arg Gly Gly Lys Val
    50                  55                  60

Trp Ile Lys Ile Phe Pro His Thr Pro Tyr Thr Lys Lys Pro Leu Glu
65                  70                  75                  80

Val Arg Met Gly Ala Gly Lys Gly Ala Val Glu Gly Trp Ile Ala Val
                85                  90                  95

Val Lys Pro Gly Arg Ile Leu Phe Glu Val Ala Gly Val Ser Glu Glu
            100                 105                 110

Val Ala Arg Glu Ala Leu Arg Leu Ala Ser His Lys Leu Pro Val Lys
        115                 120                 125

Thr Lys Phe Val Lys Arg Glu Glu Leu Gly Gly Glu Thr Asn Glu Ser
    130                 135                 140
```

<210> SEQ ID NO 12
<211> LENGTH: 122
<212> TYPE: PRT
<213> ORGANISM: STAPHYLOCOCCUS AUREUS
<220> FEATURE:
<221> NAME/KEY: MISC_FEATURE

<223> OTHER INFORMATION: 50S RIBOSOMAL PROTEIN L17; CHAIN: K

<400> SEQUENCE: 12

```
Met Gly Tyr Arg Lys Leu Gly Arg Thr Ser Asp Gln Arg Lys Ala Met
1               5                   10                  15
Leu Arg Asp Leu Ala Thr Ser Leu Ile Ile Ser Glu Arg Ile Glu Thr
            20                  25                  30
Thr Glu Ala Arg Ala Lys Glu Val Arg Ser Val Val Glu Lys Leu Ile
        35                  40                  45
Thr Leu Gly Lys Lys Gly Asp Leu Ala Ser Arg Arg Asn Ala Ala Lys
    50                  55                  60
Thr Leu Arg Asn Val Glu Ile Leu Asn Glu Asp Glu Thr Thr Gln Thr
65                  70                  75                  80
Ala Leu Gln Lys Leu Phe Gly Glu Ile Ala Glu Arg Tyr Thr Glu Arg
                85                  90                  95
Gln Gly Gly Tyr Thr Arg Ile Leu Lys Gln Gly Pro Arg Arg Gly Asp
            100                 105                 110
Gly Ala Glu Ser Val Ile Ile Glu Leu Val
            115                 120
```

<210> SEQ ID NO 13
<211> LENGTH: 119
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L18; CHAIN: L

<400> SEQUENCE: 13

```
Met Ile Ser Lys Ile Asp Lys Asn Lys Val Arg Leu Lys Arg His Ala
1               5                   10                  15
Arg Val Arg Thr Asn Leu Ser Gly Thr Ala Glu Lys Pro Arg Leu Asn
            20                  25                  30
Val Tyr Arg Ser Asn Lys His Ile Tyr Ala Gln Ile Ile Asp Asp Asn
        35                  40                  45
Lys Gly Val Thr Leu Ala Gln Ala Ser Ser Lys Asp Ser Asp Ile Ala
    50                  55                  60
Thr Thr Ala Thr Lys Val Glu Leu Ala Thr Lys Val Gly Glu Ala Ile
65                  70                  75                  80
Ala Lys Lys Ala Ala Asp Lys Gly Ile Lys Glu Ile Val Phe Asp Arg
                85                  90                  95
Gly Gly Tyr Leu Tyr His Gly Arg Val Lys Ala Leu Ala Glu Ala Ala
            100                 105                 110
Arg Glu Ser Gly Leu Glu Phe
            115
```

<210> SEQ ID NO 14
<211> LENGTH: 116
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L19; CHAIN: M

<400> SEQUENCE: 14

```
Met Thr Asn His Lys Leu Ile Glu Ala Val Thr Lys Ser Gln Leu Arg
1               5                   10                  15
Thr Asp Leu Pro Ser Phe Arg Pro Gly Asp Thr Leu Arg Val His Val
            20                  25                  30
```

```
Arg Ile Ile Glu Gly Thr Arg Glu Arg Ile Gln Val Phe Glu Gly Val
            35                  40                  45

Val Ile Lys Arg Arg Gly Gly Val Ser Glu Thr Phe Thr Val Arg
 50                  55                  60

Lys Ile Ser Ser Gly Val Gly Val Glu Arg Thr Phe Pro Leu His Thr
 65                  70                  75                  80

Pro Lys Ile Glu Lys Ile Glu Val Lys Arg Gly Lys Val Arg Arg
                85                  90                  95

Ala Lys Leu Tyr Tyr Leu Arg Ser Leu Arg Gly Lys Ala Ala Arg Ile
                100                 105                 110

Gln Glu Ile Arg
        115
```

```
<210> SEQ ID NO 15
<211> LENGTH: 118
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L20; CHAIN: N

<400> SEQUENCE: 15

Met Pro Arg Val Lys Gly Gly Thr Val Thr Arg Ala Arg Arg Lys Lys
 1               5                   10                  15

Thr Ile Lys Leu Ala Lys Gly Tyr Phe Gly Ser Lys His Thr Leu Tyr
                20                  25                  30

Lys Val Ala Lys Gln Gln Val Met Lys Ser Gly Gln Tyr Ala Phe Arg
                35                  40                  45

Asp Arg Arg Gln Arg Lys Arg Asp Phe Arg Lys Leu Trp Ile Thr Arg
 50                  55                  60

Ile Asn Ala Ala Ala Arg Gln His Glu Met Ser Tyr Ser Arg Leu Met
 65                  70                  75                  80

Asn Gly Leu Lys Lys Ala Gly Ile Asp Ile Asn Arg Lys Met Leu Ser
                85                  90                  95

Glu Ile Ala Ile Ser Asp Glu Lys Ala Phe Ala Gln Leu Val Thr Lys
                100                 105                 110

Ala Lys Asp Ala Leu Lys
        115
```

```
<210> SEQ ID NO 16
<211> LENGTH: 102
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L21; CHAIN: O

<400> SEQUENCE: 16

Met Phe Ala Ile Ile Glu Thr Gly Gly Lys Gln Ile Lys Val Glu Glu
 1               5                   10                  15

Gly Gln Glu Ile Phe Val Glu Lys Leu Asp Val Asn Glu Gly Asp Thr
                20                  25                  30

Phe Thr Phe Asp Lys Val Leu Phe Val Gly Gly Asp Ser Val Lys Val
                35                  40                  45

Gly Ala Pro Thr Val Glu Gly Ala Thr Val Ala Thr Val Asn Lys
 50                  55                  60

Gln Gly Arg Gly Lys Lys Ile Thr Val Phe Thr Tyr Lys Arg Arg Lys
 65                  70                  75                  80
```

-continued

```
Asn Ser Lys Arg Lys Lys Gly His Arg Gln Pro Tyr Thr Lys Leu Thr
                85                  90                  95

Ile Asp Lys Ile Asn Ala
            100

<210> SEQ ID NO 17
<211> LENGTH: 117
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L22; CHAIN: P

<400> SEQUENCE: 17

Met Glu Ala Lys Ala Val Ala Arg Thr Ile Arg Ile Ala Pro Arg Lys
1               5                   10                  15

Val Arg Leu Val Leu Asp Leu Ile Arg Gly Lys Asn Ala Ala Glu Ala
            20                  25                  30

Ile Ala Ile Leu Lys Leu Thr Asn Lys Ala Ser Ser Pro Val Ile Glu
        35                  40                  45

Lys Val Leu Met Ser Ala Leu Ala Asn Ala Glu His Asn Tyr Asp Met
    50                  55                  60

Asn Thr Asp Glu Leu Val Val Lys Glu Ala Tyr Ala Asn Glu Gly Pro
65                  70                  75                  80

Thr Leu Lys Arg Phe Arg Pro Arg Ala Gln Gly Arg Ala Ser Ala Ile
                85                  90                  95

Asn Lys Arg Thr Ser His Ile Thr Ile Val Val Ser Asp Gly Lys Glu
            100                 105                 110

Glu Ala Lys Glu Ala
        115

<210> SEQ ID NO 18
<211> LENGTH: 91
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L23; CHAIN: Q

<400> SEQUENCE: 18

Met Glu Ala Arg Asp Ile Leu Lys Arg Pro Val Ile Thr Glu Lys Ser
1               5                   10                  15

Ser Glu Ala Met Ala Glu Asp Lys Tyr Thr Phe Asp Val Asp Thr Arg
            20                  25                  30

Val Asn Lys Thr Gln Val Lys Met Ala Val Glu Glu Ile Phe Asn Val
        35                  40                  45

Lys Val Ala Ser Val Asn Ile Met Asn Tyr Lys Pro Lys Lys Lys Arg
    50                  55                  60

Met Gly Arg Tyr Gln Gly Tyr Thr Asn Lys Arg Arg Lys Ala Ile Val
65                  70                  75                  80

Thr Leu Lys Glu Gly Ser Ile Asp Leu Phe Asn
                85                  90

<210> SEQ ID NO 19
<211> LENGTH: 105
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L24; CHAIN: R
```

<400> SEQUENCE: 19

Met His Ile Lys Lys Gly Asp Asn Val Lys Val Ile Ala Gly Lys Asp
1               5                   10                  15

Lys Gly Lys Glu Gly Lys Val Ile Ala Thr Leu Pro Lys Lys Asp Arg
            20                  25                  30

Val Val Val Glu Gly Val Asn Ile Met Lys Lys His Gln Lys Pro Thr
        35                  40                  45

Gln Leu Asn Pro Glu Gly Gly Ile Leu Glu Thr Glu Ala Ala Ile His
    50                  55                  60

Val Ser Asn Val Gln Leu Leu Asp Pro Lys Thr Asn Glu Pro Thr Arg
65                  70                  75                  80

Val Gly Tyr Lys Phe Val Asp Gly Lys Lys Val Arg Ile Ala Lys Lys
                85                  90                  95

Ser Gly Glu Glu Ile Lys Ser Asn Asn
            100                 105

<210> SEQ ID NO 20
<211> LENGTH: 217
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L25; CHAIN: S

<400> SEQUENCE: 20

Met Ala Ser Leu Lys Ser Ile Ile Arg Gln Gly Lys Gln Thr Arg Ser
1               5                   10                  15

Asp Leu Lys Gln Leu Arg Lys Ser Gly Lys Val Pro Ala Val Val Tyr
            20                  25                  30

Gly Tyr Gly Thr Lys Asn Val Ser Lys Val Asp Gly Val Glu Phe
        35                  40                  45

Ile Lys Val Ile Arg Glu Val Gly Arg Asn Gly Val Ile Glu Leu Gly
    50                  55                  60

Val Gly Ser Lys Thr Ile Lys Val Met Val Ala Asp Tyr Gln Phe Asp
65                  70                  75                  80

Pro Leu Lys Asn Gln Ile Thr His Ile Asp Phe Leu Ala Ile Asn Met
                85                  90                  95

Ser Glu Glu Arg Thr Val Glu Val Pro Val Gln Leu Val Gly Glu Ala
            100                 105                 110

Val Gly Ala Lys Glu Gly Gly Val Val Glu Gln Pro Leu Phe Asn Leu
            115                 120                 125

Glu Val Thr Ala Thr Pro Asp Asn Ile Pro Glu Ala Ile Glu Val Asp
            130                 135                 140

Ile Thr Glu Leu Asn Ile Asn Asp Ser Leu Thr Val Ala Asp Val Lys
145                 150                 155                 160

Val Thr Gly Asp Phe Lys Ile Glu Asn Asp Ser Ala Glu Ser Val Val
                165                 170                 175

Thr Val Val Ala Pro Thr Glu Glu Pro Thr Glu Glu Ile Glu Ala
            180                 185                 190

Met Glu Gly Glu Gln Gln Thr Glu Glu Pro Val Val Gly Glu Ser
            195                 200                 205

Lys Glu Asp Glu Glu Lys Thr Glu Glu
            210                 215

<210> SEQ ID NO 21

```
<211> LENGTH: 94
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L27; CHAIN: T

<400> SEQUENCE: 21
```

| Met | Leu | Lys | Leu | Asn | Leu | Gln | Phe | Phe | Ala | Ser | Lys | Lys | Gly | Val | Ser |
|---|---|---|---|---|---|---|---|---|---|---|---|---|---|---|---|
| 1 | | | | 5 | | | | | 10 | | | | | 15 | |

| Ser | Thr | Lys | Asn | Gly | Arg | Asp | Ser | Glu | Ser | Lys | Arg | Leu | Gly | Ala | Lys |
|---|---|---|---|---|---|---|---|---|---|---|---|---|---|---|---|
| | | | 20 | | | | | 25 | | | | | 30 | | |

| Arg | Ala | Asp | Gly | Gln | Phe | Val | Thr | Gly | Gly | Ser | Ile | Leu | Tyr | Arg | Gln |
|---|---|---|---|---|---|---|---|---|---|---|---|---|---|---|---|
| | | | 35 | | | | | 40 | | | | | 45 | | |

| Arg | Gly | Thr | Lys | Ile | Tyr | Pro | Gly | Glu | Asn | Val | Gly | Arg | Gly | Gly | Asp |
|---|---|---|---|---|---|---|---|---|---|---|---|---|---|---|---|
| | | 50 | | | | | 55 | | | | | 60 | | | |

| Asp | Thr | Leu | Phe | Ala | Lys | Ile | Asp | Gly | Val | Val | Lys | Phe | Glu | Arg | Lys |
|---|---|---|---|---|---|---|---|---|---|---|---|---|---|---|---|
| 65 | | | | | 70 | | | | | 75 | | | | | 80 |

| Gly | Arg | Asp | Lys | Lys | Gln | Val | Ser | Val | Tyr | Ala | Val | Ala | Glu |
|---|---|---|---|---|---|---|---|---|---|---|---|---|---|
| | | | | 85 | | | | | 90 | | | | |

```
<210> SEQ ID NO 22
<211> LENGTH: 62
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L28; CHAIN: U

<400> SEQUENCE: 22
```

| Met | Gly | Lys | Gln | Cys | Phe | Val | Thr | Gly | Arg | Lys | Ala | Ser | Thr | Gly | Asn |
|---|---|---|---|---|---|---|---|---|---|---|---|---|---|---|---|
| 1 | | | | 5 | | | | | 10 | | | | | 15 | |

| Arg | Arg | Ser | His | Ala | Leu | Asn | Ser | Thr | Lys | Arg | Arg | Trp | Asn | Ala | Asn |
|---|---|---|---|---|---|---|---|---|---|---|---|---|---|---|---|
| | | | 20 | | | | | 25 | | | | | 30 | | |

| Leu | Gln | Lys | Val | Arg | Ile | Leu | Val | Asp | Gly | Lys | Pro | Lys | Lys | Val | Trp |
|---|---|---|---|---|---|---|---|---|---|---|---|---|---|---|---|
| | | | 35 | | | | | 40 | | | | | 45 | | |

| Val | Ser | Ala | Arg | Ala | Leu | Lys | Ser | Gly | Lys | Val | Thr | Arg | Val |
|---|---|---|---|---|---|---|---|---|---|---|---|---|---|
| | 50 | | | | | 55 | | | | | 60 | | |

```
<210> SEQ ID NO 23
<211> LENGTH: 69
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L29; CHAIN: V

<400> SEQUENCE: 23
```

| Met | Lys | Ala | Lys | Glu | Ile | Arg | Asp | Leu | Thr | Thr | Ser | Glu | Ile | Glu | Glu |
|---|---|---|---|---|---|---|---|---|---|---|---|---|---|---|---|
| 1 | | | | 5 | | | | | 10 | | | | | 15 | |

| Gln | Ile | Lys | Ser | Ser | Lys | Glu | Glu | Leu | Phe | Asn | Leu | Arg | Phe | Gln | Leu |
|---|---|---|---|---|---|---|---|---|---|---|---|---|---|---|---|
| | | | 20 | | | | | 25 | | | | | 30 | | |

| Ala | Thr | Gly | Gln | Leu | Glu | Glu | Thr | Ala | Arg | Ile | Arg | Thr | Val | Arg | Lys |
|---|---|---|---|---|---|---|---|---|---|---|---|---|---|---|---|
| | | | 35 | | | | | 40 | | | | | 45 | | |

| Thr | Ile | Ala | Arg | Leu | Lys | Thr | Val | Ala | Arg | Glu | Arg | Glu | Ile | Glu | Gln |
|---|---|---|---|---|---|---|---|---|---|---|---|---|---|---|---|
| | | 50 | | | | | 55 | | | | | 60 | | | |

| Ser | Lys | Ala | Asn | Gln |
|---|---|---|---|---|
| 65 | | | | |

```
<210> SEQ ID NO 24
<211> LENGTH: 59
```

```
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L30; CHAIN: W

<400> SEQUENCE: 24

Met Ala Lys Leu Gln Ile Thr Leu Thr Arg Ser Val Ile Gly Arg Pro
1               5                   10                  15

Glu Thr Gln Arg Lys Thr Val Glu Ala Leu Gly Leu Lys Lys Thr Asn
            20                  25                  30

Ser Ser Val Val Val Glu Asp Asn Pro Ala Ile Arg Gly Gln Ile Asn
        35                  40                  45

Lys Val Lys His Leu Val Thr Val Glu Glu Lys
    50                  55

<210> SEQ ID NO 25
<211> LENGTH: 58
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L32; CHAIN: Z

<400> SEQUENCE: 25

Met Ala Val Pro Lys Arg Arg Thr Ser Lys Thr Arg Lys Asn Lys Arg
1               5                   10                  15

Arg Thr His Phe Lys Ile Ser Val Pro Gly Met Thr Glu Cys Pro Asn
            20                  25                  30

Cys Gly Arg Glu Tyr Lys Leu Ser His Arg Val Cys Lys Asn Cys Gly
        35                  40                  45

Ser Tyr Asn Gly Glu Glu Val Ala Ala Lys
    50                  55

<210> SEQ ID NO 26
<211> LENGTH: 45
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L34; CHAIN: 2

<400> SEQUENCE: 26

Met Val Lys Arg Thr Tyr Gln Pro Asn Lys Arg Lys His Ser Lys Val
1               5                   10                  15

His Gly Phe Arg Lys Arg Met Ser Thr Lys Asn Gly Arg Lys Val Leu
            20                  25                  30

Ala Arg Arg Arg Arg Lys Gly Arg Lys Val Leu Ser Ala
        35                  40                  45

<210> SEQ ID NO 27
<211> LENGTH: 66
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L35; CHAIN: 3

<400> SEQUENCE: 27

Met Pro Lys Met Lys Thr His Arg Gly Ala Ala Lys Arg Val Lys Arg
1               5                   10                  15

Thr Ala Ser Gly Gln Leu Lys Arg Ser Arg Ala Phe Thr Ser His Leu
            20                  25                  30
```

```
Phe Ala Asn Lys Ser Thr Lys Gln Lys Arg Gln Leu Arg Lys Ala Arg
        35                  40                  45

Leu Val Ser Lys Ser Asp Met Lys Arg Val Lys Gln Leu Leu Ala Tyr
 50                  55                  60

Lys Lys
65

<210> SEQ ID NO 28
<211> LENGTH: 37
<212> TYPE: PRT
<213> ORGANISM: STAPHYLOCOCCUS AUREUS
<220> FEATURE:
<221> NAME/KEY: MISC_FEATURE
<223> OTHER INFORMATION: 50S RIBOSOMAL PROTEIN L36; CHAIN: 4

<400> SEQUENCE: 28

Met Lys Val Arg Pro Ser Val Lys Pro Ile Cys Glu Lys Cys Lys Val
 1               5                  10                  15

Ile Lys Arg Lys Gly Lys Val Met Val Ile Cys Glu Asn Pro Lys His
             20                  25                  30

Lys Gln Arg Gln Gly
             35
```